(12) United States Patent
Jinno

(10) Patent No.: US 8,277,443 B2
(45) Date of Patent: Oct. 2, 2012

(54) MANIPULATOR

(75) Inventor: Makoto Jinno, Ashigarakami-gun (JP)

(73) Assignees: Kabushiki Kaisha Toshiba, Tokyo (JP); Terumo Kabushiki Kaisha, Tokyo (JP)

( * ) Notice: Subject to any disclaimer, the term of this patent is extended or adjusted under 35 U.S.C. 154(b) by 658 days.

(21) Appl. No.: 12/261,829

(22) Filed: Oct. 30, 2008

(65) Prior Publication Data
US 2009/0112230 A1 Apr. 30, 2009

(30) Foreign Application Priority Data

Oct. 31, 2007 (JP) ................................. 2007-283323

(51) Int. Cl.
*A61B 17/00* (2006.01)

(52) U.S. Cl. .................... 606/1; 901/7; 901/14; 901/36; 606/130; 606/205; 81/300; 81/342

(58) Field of Classification Search ........ 433/4; 30/221; 81/300, 342
See application file for complete search history.

(56) References Cited

U.S. PATENT DOCUMENTS

| | | | |
|---|---|---|---|
| 4,782,833 A | 11/1988 | Einhorn et al. | |
| 5,649,955 A | 7/1997 | Hashimoto et al. | |
| 5,792,165 A | 8/1998 | Klieman et al. | |
| 6,077,287 A | 6/2000 | Taylor et al. | |
| 6,889,116 B2 | 5/2005 | Jinno | |
| 7,300,373 B2 | 11/2007 | Jinno et al. | |
| 7,608,083 B2 * | 10/2009 | Lee et al. | 606/130 |
| 2005/0090809 A1 | 4/2005 | Cooper et al. | |
| 2007/0208375 A1* | 9/2007 | Nishizawa et al. | 606/205 |
| 2009/0112229 A1 | 4/2009 | Omori et al. | |

FOREIGN PATENT DOCUMENTS

| | | |
|---|---|---|
| DE | 41 36 861 A1 | 5/1993 |
| EP | 0 677 275 A2 | 10/1995 |
| EP | 1 707 153 A1 | 10/2006 |
| JP | 63-176092 U | 11/1988 |
| JP | 63-288147 | 11/1988 |
| JP | 8-33628 | 2/1996 |
| JP | 10-179601 | 7/1998 |

(Continued)

OTHER PUBLICATIONS

Japanese Office Action issued Apr. 24, 2012, in Patent Application No. 2007-283323 (with Partial English-language translation).

*Primary Examiner* — Gary Jackson
*Assistant Examiner* — Kevin Everage
(74) *Attorney, Agent, or Firm* — Oblon, Spivak, McClelland, Maier & Neustadt, L.L.P.

(57) ABSTRACT

A manipulator includes a wire which is movable back and forth, a driven wire both ends of which are connected to the wire, an idle pulley, a guide pulley, a driven pulley which is movable back and forth, and an end effector coupled to the driven pulley. The driven wire passes from a terminal along a first side on the idle pulley and extends to a second side opposite to the first side, and then passes along the second side on the driven pulley. The driven wire is then wound around the driven pulley and passes along the first side on the driven pulley and then the second side on the idle pulley, and finally returns to the terminal, thereby making up an 8-shaped configuration path. The driven wire is crossed between the idle pulley and the guide pulley.

7 Claims, 43 Drawing Sheets

FOREIGN PATENT DOCUMENTS

| | | |
|---|---|---|
| JP | 2002-102248 | 4/2002 |
| JP | 2002-282257 | 10/2002 |
| JP | 2003-61969 | 3/2003 |
| JP | 2003-111765 | 4/2003 |
| JP | 3421117 | 4/2003 |
| JP | 2004-122286 | 4/2004 |
| JP | 2004-301275 | 10/2004 |
| JP | 2006-247804 | 9/2006 |

* cited by examiner

MANIPULATOR

BACKGROUND OF THE INVENTION

1. Field of the Invention

The present invention relates to a manipulator having a distal end working unit which includes an end effector.

2. Description of the Related Art

According to a laparoscopic surgical operation process, some small holes are opened in the abdominal region, for example, of a patient and an endoscope and manipulators or forceps are inserted into the holes. The surgeon performs a surgical operation on the patient with the manipulators or forceps while watching an image captured by the endoscope and displayed on a display monitor. Since the laparoscopic surgical operation process does not require a laparotomy, it is less burdensome on the patient and greatly reduces the number of days required for the patient to spend before recovering from the operation or being released from the hospital, it is expected to increase a range of surgical operations to which it is applicable.

Manipulators for laparoscopic surgical operations are required to allow the operator, i.e., the surgeon, to perform various appropriate techniques quickly depending on the position and size of the affected part, for removing, suturing, and ligating the affected part. The applicants have proposed manipulators which can be manipulated simply with a high degree of freedom (see, for example, JP 2002-102248 A and JP 2004-301275 A).

When the surgeon uses forceps of the general nature in a flexible scope surgery or a laparoscopic surgery, external forces applied to the distal end working unit of the forceps and gripping forces applied by the distal end working unit are transmitted, not directly, but as reactive forces, to the hand of the surgeon. Therefore, the surgeon can feel those forces to a certain extent and can operate the forceps based on the reactive forces. The forceps that have been available heretofore, however, have few degrees of freedom, e.g., one degree of freedom, are difficult to handle because they are movable only in limited directions to grip and cut tissues and also to insert suture needles, and require surgeons to be skilled in using them.

To achieve higher degrees of freedom, one option is to use a master-slave remote control surgical robot, for example. The master-slave remote control surgical robot is advantageous in that it has high degrees of freedom, can approach the affected part of a patient from various desired directions, and can be operated effectively and efficiently. However, external forces applied to the distal end working unit and gripping forces applied by the distal end working unit are not transmitted to the master side of the master-slave remote control surgical robot.

If a force feeling is to be available on the master side of the master-slave remote control surgical robot, then the surgical robot will need to be an expensive and complex system as it needs a highly sophisticated bilateral control architecture based on a highly sensitive force sensing system and a computer system having high-speed sampling times. In addition, the bilateral control architecture has not yet reached a practically sufficient performance level at present.

The applicants have already proposed multiple-degree-of-freedom forceps including a distal end working unit having joints that can be actuated by motors based on commands from an operating unit. Since the operating unit, i.e., an operating handle, and the working unit, i.e., distal end joints, are integrally coupled to each other, external forces applied to the distal end working unit and gripping forces applied by the distal end working unit are transmitted, not directly, but via the multiple-degree-of-freedom forceps, to the operating unit. Therefore, the operator of the multiple-degree-of-freedom forceps can feel those forces to a certain extent. Nevertheless, there are demands for multiple-degree-of-freedom forceps which allow the operator to feel stronger forces, in particular, multiple-degree-of-freedom forceps which allow the operator to feel stronger gripping forces.

SUMMARY OF THE INVENTION

It is one of the objects of the present invention to provide a manipulator that has high degrees of freedom and allows an operator to feel the external and other forces applied to a distal end working unit more reliably and easily.

It is one of the objects of the present invention to provide a manipulator that can reduce the number of gears used and is made up of a simple structure.

According to one aspect of the present invention, there is provided a manipulator having a distal end side and a proximal end side thereof. The manipulator comprises a drive member disposed on the proximal end side and being movable back and forth, a ring-like flexible member, part of which is connected to the drive member, an idle cylindrical member disposed closer to the distal end side than the drive member, a driven cylindrical member disposed closer to the distal end side than the idle cylindrical member, and being movable back and forth, a guide cylindrical member disposed between the idle cylindrical member and the driven cylindrical member, and an end effector being coupled to the driven cylindrical member. The flexible member passes along both sides of the idle cylindrical member and is wound around the driven cylindrical member, and the flexible member crosses between the idle cylindrical member and the guide cylindrical member.

Further, according to another aspect of the present invention, there is provided a manipulator having a distal end side and a proximal end side thereof. The manipulator comprises a drive member disposed on the proximal end side and being movable back and forth, a ring-like flexible member, part of which is connected to the drive member, a guide cylindrical member disposed closer to the distal end side than the drive member, a driven cylindrical member disposed closer to the distal end side than the guide cylindrical member, and being movable back and forth, and an end effector being coupled to the driven cylindrical member. The flexible member is wound in one turn or more around the guide cylindrical member and the driven cylindrical member, respectively.

With such a manipulator, its structure is kept out of interference with the other operating axes, thereby making it possible to easily construct the distal end working unit with high degrees of freedom.

The drive members, which are mechanically connected to the manually operable input unit, allow the operator to feel the external forces etc. that are applied to the distal end working unit more reliably and easily. Moreover, the end effector driving mechanism is made up of a simple structure that is free of gears.

Still further, according to another aspect of the present invention, there is provided a manipulator comprising an operating unit including a manually operable input unit, a distal end working unit including an end effector axis and at least one attitude axis for changing orientation of the end effector axis, a coupling unit for coupling the operating unit and the distal end working unit to each other, an attitude axis actuator for actuating the attitude axis, and an operation transmitting unit for mechanically transmitting a manual operation applied to the input unit to actuate the end effector axis.

The operation transmitting unit allows the end effector axis to be directly actuated manually by an operator. The operator can feel the external and other forces that are applied to the distal end working unit more reliably and easily. Also, the orientation of the end effector axis can be changed through the attitude axis, and thus high degrees of freedom can be obtained.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENT

Preferred embodiments of manipulators according to the present invention will be described in detail below with reference to FIGS. 1 through 43.

Figure 1:
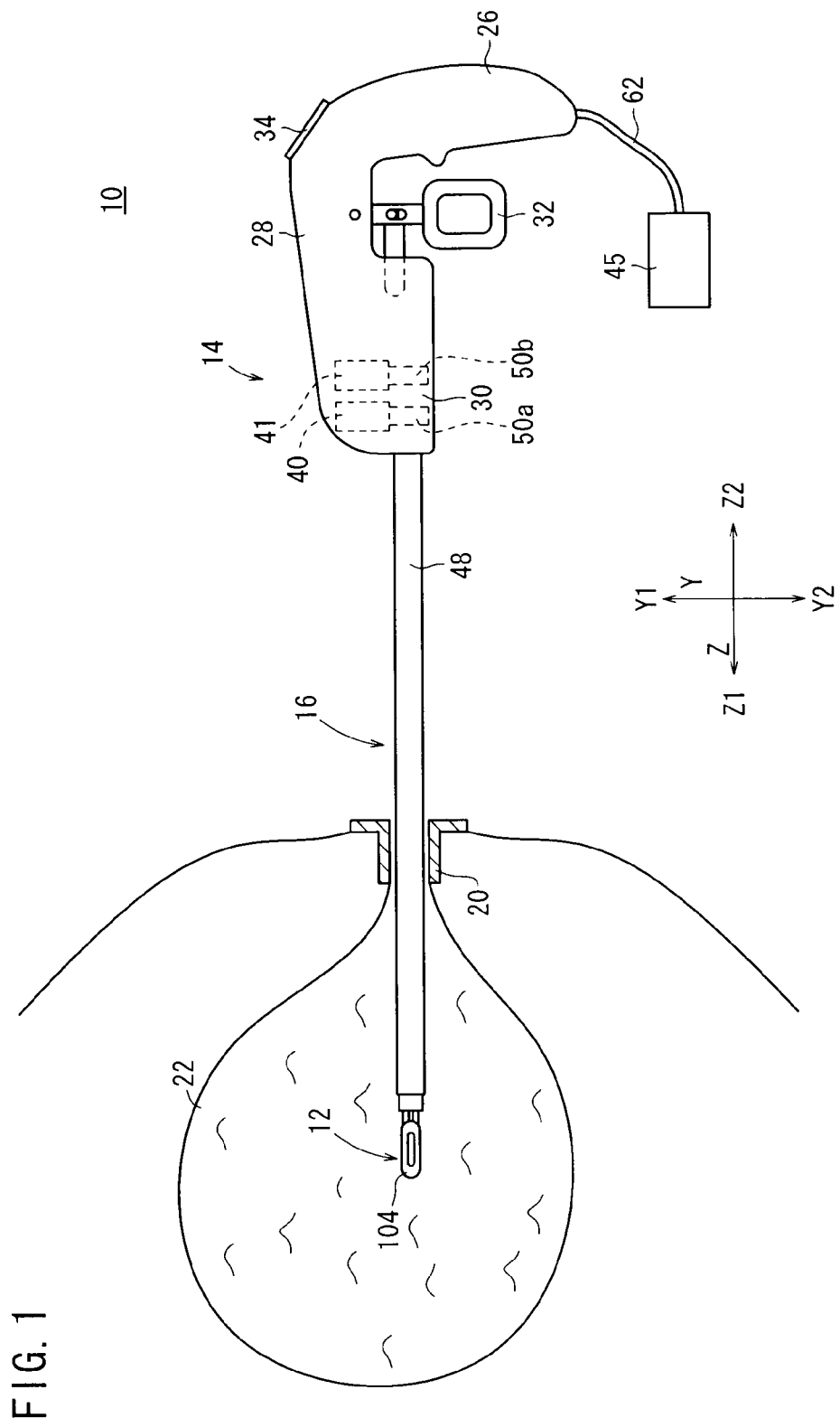
FIG. 1 is a side elevational view of a manipulator.

As shown in FIG. 1, the manipulator 10 according to the present embodiment makes up part of a medical manipulator system, and is connected to a controller 45.

The controller 45, which serves to control the manipulator 10 electrically, is connected via a connector to a cable 62 extending from a lower end of a grip handle 26. The controller 45 can control a plurality of manipulators 10 independently of each other. Of course, a controller for controlling a single manipulator 10 may also be used.

The manipulator 10 includes a distal end working unit 12 for gripping a portion of a living tissue, and a curved needle, or the like for performing a given treatment. The manipulator 10 usually is referred to as a gripping forceps or a needle driver (needle holder).

Figure 2:
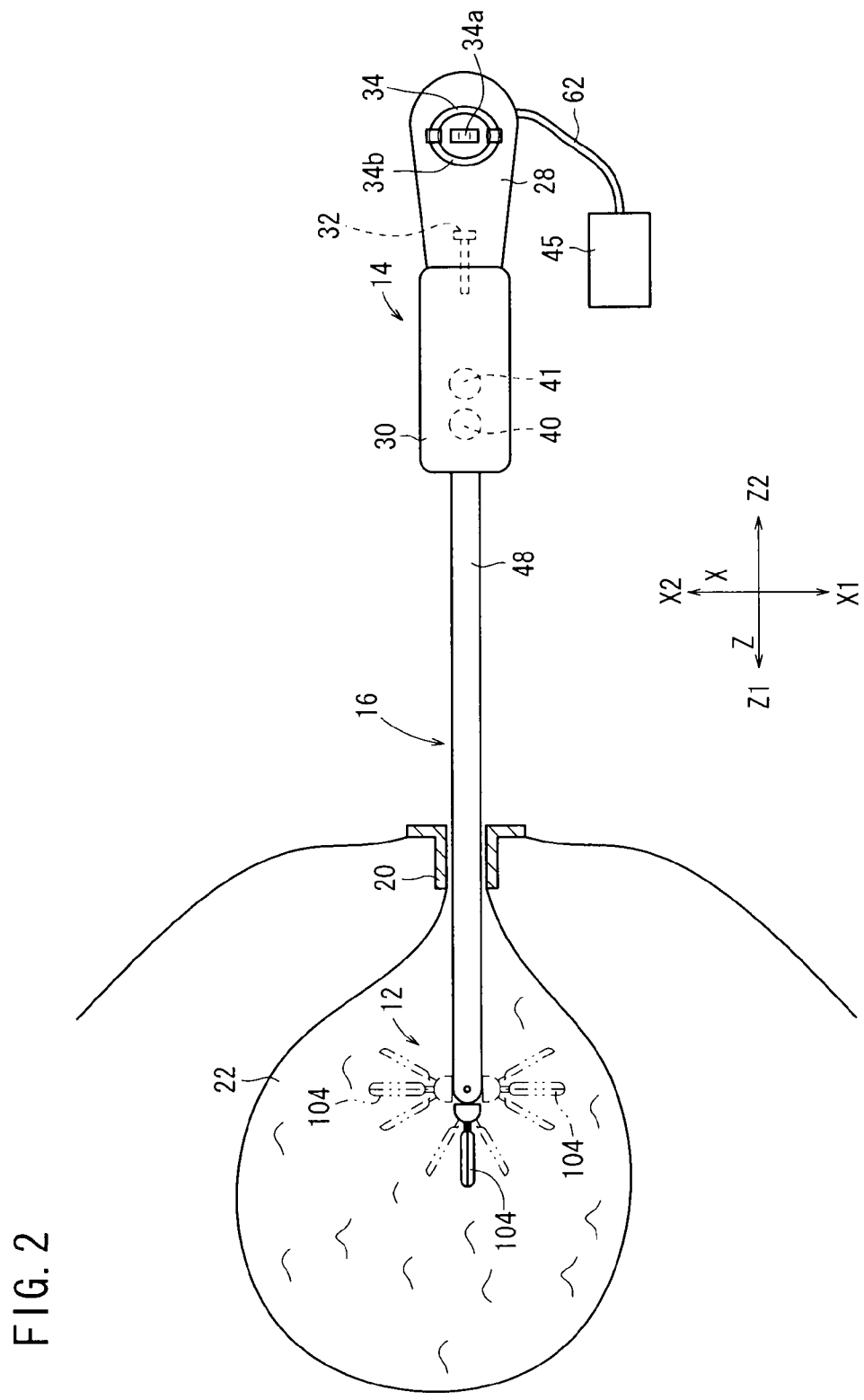
FIG. 2 is a plan view of the manipulator.
Figure 3:
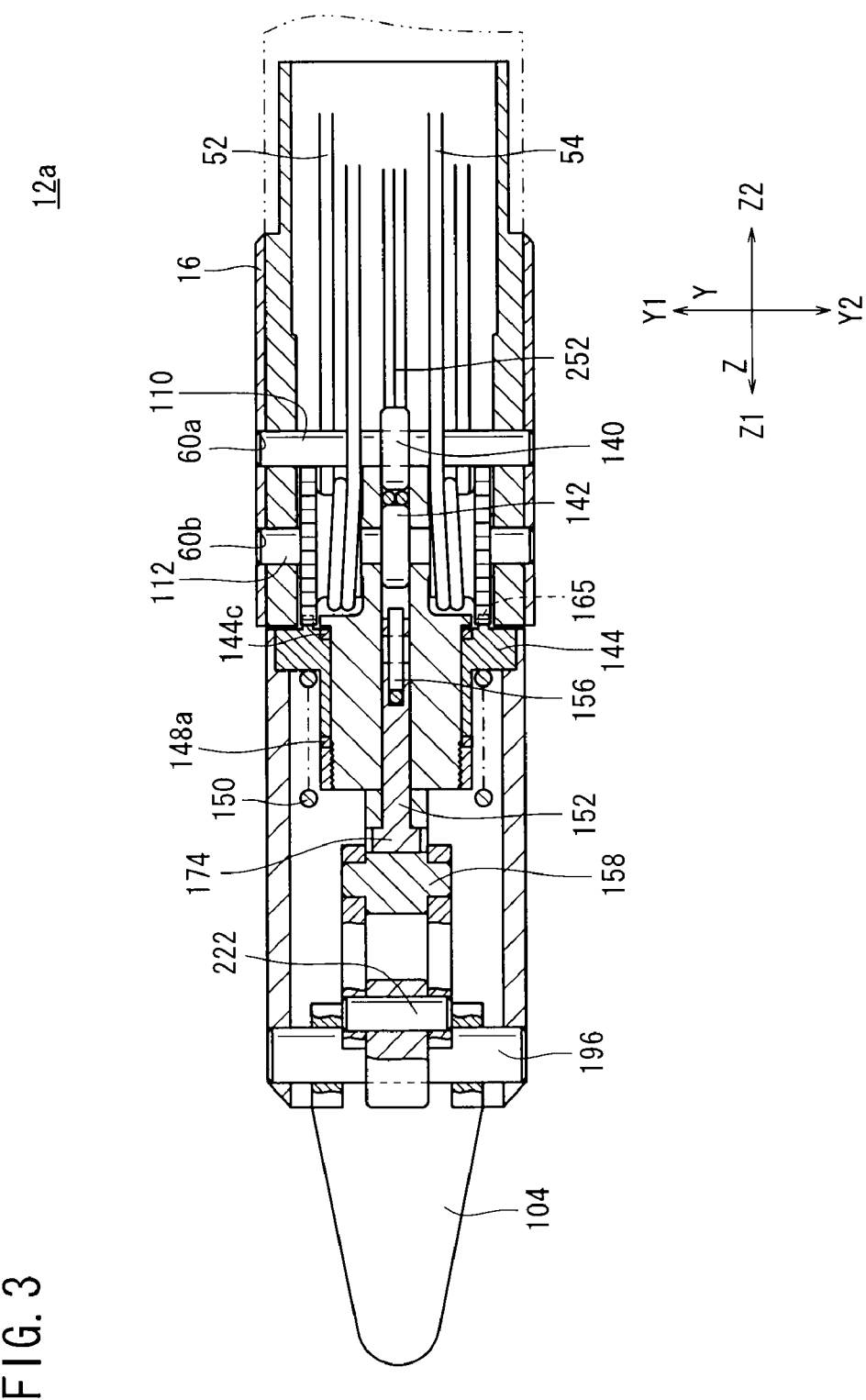
FIG. 3 is a sectional side elevational view of a distal end working unit according to a first embodiment.
Figure 4:
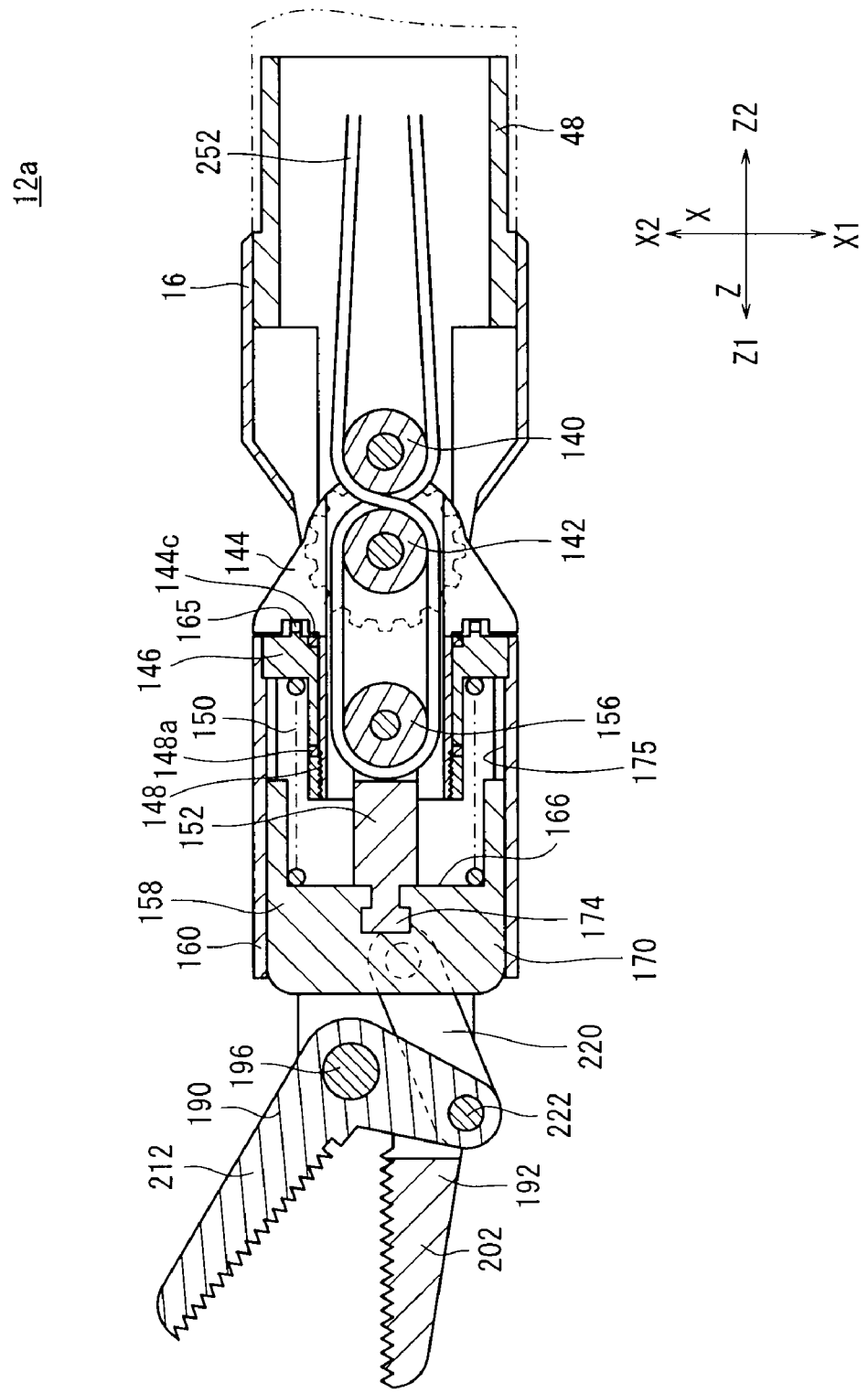
FIG. 4 is a sectional plan view of the distal end working unit according to the first embodiment.

As shown in FIGS. 1 and 2, the manipulator 10 comprises an operating unit 14, which is held and operated by the hand, and a working unit 16 fixed to the operating unit 14. The operating unit 14 and the working unit 16 are integrally combined with each other. However, depending on conditions, the operating unit 14 and the working unit 16 may be separable from each other.

In the following description, it shall be assumed that transverse directions in FIGS. 1 and 2 are referred to as X directions, vertical directions as Y directions, and longitudinal directions of a connector shaft 48 as Z directions. Among the X directions, the rightward direction as viewed from the distal end is referred to as an X1 direction, and the leftward direction as an X2 direction. Among the Y directions, the upward direction is referred to as a Y1 direction, and the downward direction as a Y2 direction. Among the Z directions, the forward direction is referred to as a Z1 direction, and the rearward direction as a Z2 direction. Unless otherwise noted, these directions represent directions of the manipulator 10 when it is in a neutral posture. The above definitions of directions are for illustrative purposes only. The manipulator 10 can be used in any of various orientations, e.g., it may be used upside down.

The working unit 16 comprises a distal end working unit 12 for performing working operations, and an elongate hollow connector shaft (coupling unit) 48 coupling the distal end working unit 12 and the operating unit 14 to each other. The distal end working unit 12 and the connector shaft 48 have a small diameter, and can be inserted into a body cavity 22 through a trocar 20 in the form of a hollow cylinder mounted inside an abdominal region or the like of the patient. The distal end working unit 12 is actuated by a composite input unit 34 in order to perform various techniques to grip, remove, suture, or tie-knot an affected part of the patient's body within the body cavity 22.

The operating unit 14 includes a grip handle 26, which is gripped by the hand, a bridge 28 extending from an upper portion of the grip handle 26, and an actuator block 30 and a trigger lever (input unit) 32, which are connected to a distal end of the bridge 28.

As shown in FIG. 1, the grip handle 26 of the operating unit 14 extends in the Y2 direction from the end of the bridge 28, and has a length suitable for being gripped by the hand. The composite input unit 34 is disposed on the grip handle 26.

The cable 62 connected to the controller 45 is disposed on a lower end of the grip handle 26 while being integrally connected to the grip handle 26. The grip handle 26 and the cable 62 may be connected to each other by a connector.

The composite input unit 34 makes up a composite input means for imparting rotational commands in rolling (shaft rotating) and yawing (left and right) directions to the distal end working unit 12. For example, commands in the yawing direction are given by a first input means 34a, which operate in the lateral direction, whereas commands in the rolling direction are given by a second input means 34b, which operate in the shaft rotating direction. The trigger lever 32 comprises an input means for imparting opening and closing commands for an end effector 104 (see FIG. 1) of the distal end working unit 12. Although the end effector 104 is available in various forms, the manipulator 10 employs an openable and closable gripper.

The composite input unit 34 includes an input sensor for detecting a control variable, and supplies a detection operation signal (e.g., an analog signal) to the controller 45.

The trigger lever 32 comprises a lever disposed below the bridge 28 and is disposed at a position where it can easily be operated by the index finger. The trigger lever 32 is connected to the actuator block 30 by a first link 64 and a second link 66, and is movable toward and away from the grip handle 26. The first link 64 pivots swingably about a portion of the bridge 28, and the trigger lever 32 is mounted on the end of the first link 64 in the Y2 direction. The second link 66 projects in the Z2 direction from the actuator block 30 and engages in an oblong hole 64a formed in the first link 64. The second link 66 is movable back and forth in the longitudinal direction in the oblong hole 64a when the trigger lever 32 is moved.

The second link 66 is connected to an end of a wire (drive member) 56. When the trigger lever 32 is pulled, the wire 56 also is pulled in unison therewith. Since the wire 56 is used as a drive member (transmitting member) connected to the second link 66, the number of parts used can be reduced, and the manipulator 10 is reduced in weight.

The drive member connected to the second link 66 may comprise a rigid linearly movable rod (or link), for example, rather than the wire 56. Since a rod is generally more rigid than the wire, the rod may be used as a linearly movable member for producing large gripping forces. The rod and the second link 66 may be combined integrally with each other.

Links, gears, etc., may be operatively disposed between the second link 66 and the wire 56, for adjusting the operating forces and strokes of the operator.

The actuator block 30 houses motors (attitude axis actuators) 40, 41 therein corresponding to the respective mechanisms of two out of three degrees of freedom, which are incorporated in the distal end working unit 12. The motors 40, 41 are arrayed in parallel with each other in the longitudinal direction of the connector shaft 48. The motors 40, 41 correspond to movements in both rolling and yawing directions of the distal end working unit 12. The motors 40, 41 are small in size and diameter, thus enabling the actuator block 30 to be compact and flat in shape. The motors 40, 41 can be energized to rotate the drive shafts under the control of the controller 45, based on operation of the operating unit 14. The motors 40, 41 are combined with angle sensors, for detecting rotational angles and supplying the detected angle signals to the controller 45. The angle sensors may comprise rotary encoders, for example.

The actuator block 30 houses pulleys 50a, 50b therein, which are connected, respectively, to the drive shafts of the motors 40, 41.

Figure 6:
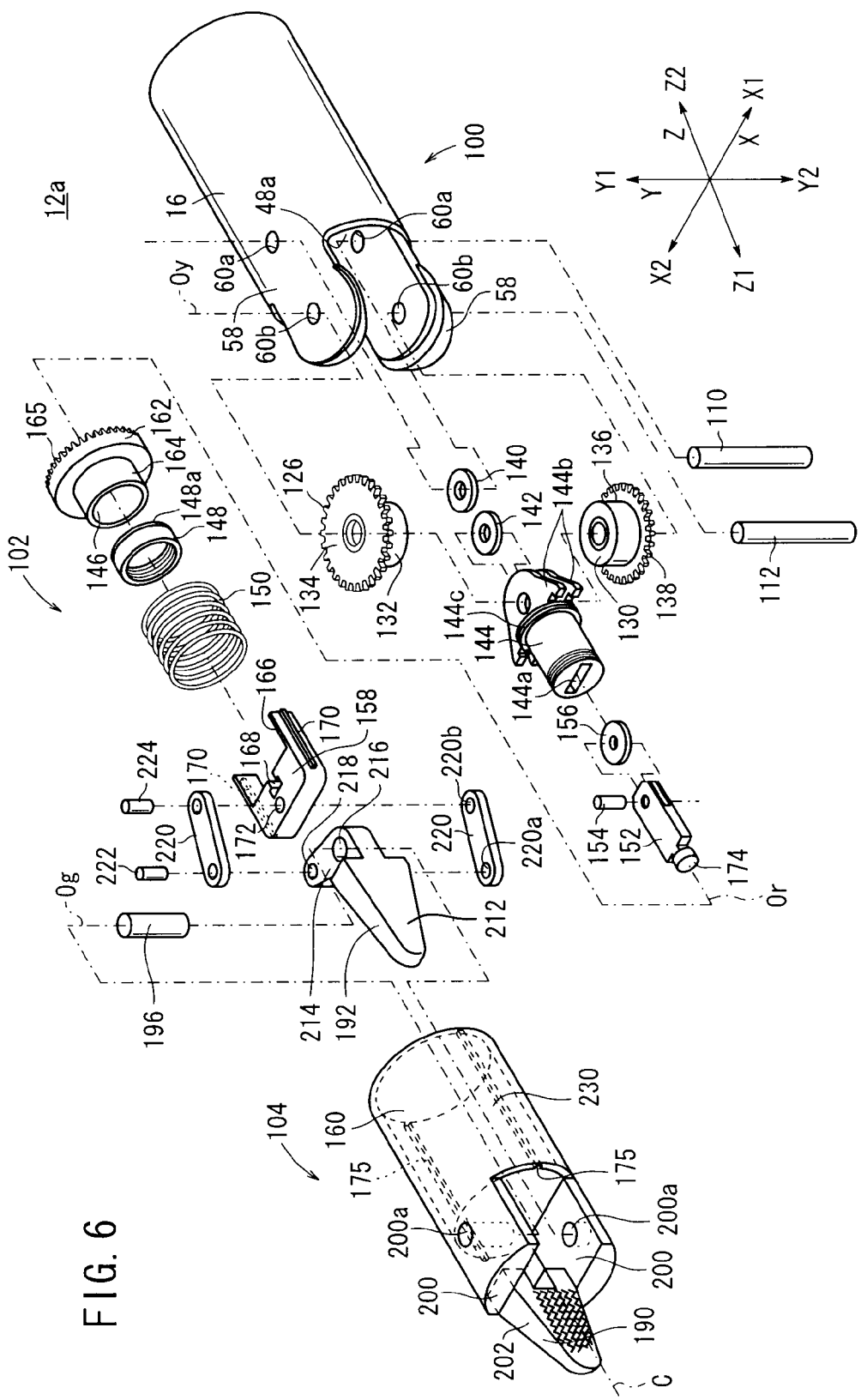
FIG. 6 is an exploded perspective view of the distal end working unit according to the first embodiment.

Wires 52, 54 are wound respectively around the pulleys 50a, 50b, and extend through a hollow region 48a (see FIG. 6)

in the connector shaft 48 toward the distal end working unit 12. The wires 52, 54 may both be of the same type and have the same diameter.

The composite input unit 34 and the trigger lever 32 of the operating unit 14 are not limited to the above-described and illustrated positions, forms, and operating methods. For example, the composite input unit 34 may be replaced with operating rollers, buttons, or a joystick. Further, other positions and methods, which allow the manipulator to be easily operated, may be selected and designed.

A manual operation applied to the trigger lever 32 is mechanically transmitted to open and close the end effector 104. The first link 64, the second link 66, the wire 56, and an end effector driving mechanism 260, to be described later, serve as a means for mechanically transmitting a manual action between the trigger lever 32 and the end effector 104, and make up an operation transmitting unit.

The term "mechanically" refers to a system for transmitting manual operations via a wire, a chain, a timing belt, a link, a rod, a gear, or the like, which is mainly actuated in the power transmitting direction by a mechanical component in the form of a nonelastic solid body. Although a wire, a chain, or the like, is slightly elongatable inevitably under tension, it is still regarded as a mechanical component in the form of a nonelastic solid body.

First through fifth embodiments 12a through 12e, and a modification 12f of the distal end working unit 12, shall be described below.

As shown in FIGS. 3, 4, 5, 6, and 7, the distal end working unit 12a according to the first embodiment comprises a wire-driven mechanism 100, a composite mechanism 102, and an end effector 104. The distal end working unit 12 incorporates therein mechanisms providing three degrees of freedom. These mechanisms include a mechanism having a first degree of freedom for angularly moving a portion of the distal end working unit 12 that is positioned ahead of a first rotational axis Oy extending along the Y direction, in a yawing direction about the first rotational axis Oy, a mechanism having a second degree of freedom for angularly moving the portion of the distal end working unit 12 in a rolling direction about a second rotational axis Or, and a mechanism having a third degree of freedom for opening and closing the end effector 104 on the distal end of the distal end working unit 12 about a third rotational axis Og.

The first rotational axis Oy of the mechanism having the first degree of freedom may be angularly movable out of parallelism with an axis C, which extends from the proximal end to the distal end of the connector shaft 48. The second rotational axis Or of the mechanism having the second degree of freedom may be angularly movable, about an axis along the direction in which the distal end (the end effector 104) of the distal end working unit 12 extends, with the distal end portion thereof being rotatable in the rolling direction.

The mechanism having the first degree of freedom (i.e., which is movable in the yawing direction) has an operable range of ±90° or greater, for example. The mechanism having the second degree of freedom (i.e., which is movable in the rolling direction) has an operable range of ±180° or greater, for example. The mechanism having the third degree of freedom (i.e., the end effector 104) may be opened through 40° or greater, for example.

The end effector 104 comprises a member for performing actual work during an operation. The first rotational axis Oy and the second rotational axis Or are axes for changing the attitude of the end effector 104 for facilitating the work. Generally, the mechanism having the third degree of freedom for opening and closing the end effector 104 is referred to as a gripper (or a gripper axis). The mechanism having the first degree of freedom for turning in a yawing direction is referred to as a yaw axis, and the mechanism having the second degree of freedom for turning in a rolling direction is referred to as a roll axis.

The wire-driven mechanism 100 is disposed between a pair of tongue pieces 58 and serves to convert reciprocating movement of the respective wires 52, 54 into rotational movement, and to transmit such rotational movement to a composite mechanism 102. The wire-driven mechanism 100 includes a shaft 110, which is inserted into shaft holes 60a, 60a, and a shaft 112, which is inserted into shaft holes 60b, 60b. The shafts 110, 112 are press-fitted or welded securely to the shaft holes 60a, 60b. The shaft 112 is aligned axially with the first rotational axis Oy.

Gear bodies 126, 130, which are symmetrically shaped in the Y direction, are mounted respectively on both ends of the shaft 112, respectively, in the Y direction. The gear body 126 comprises a tubular member 132 and a first gear 134 disposed concentrically on an upper portion of the tubular member 132. The gear body 130 is essentially identical in shape to the gear body 126, and is aligned with the gear body 126 in the Y direction. The gear body 130 comprises a tubular member 136 and a second gear 138 disposed concentrically on a lower portion of the tubular member 136. The gears 134, 138 are held in mesh with upper and lower ends of the face gear 165 of a gear body 146, to be described later.

The tubular member 136 is substantially identical in diameter and shape to the tubular member 132. Wires 52, 54 are wound around the tubular members 132, 136 and have portions fastened thereto by a securing means. The wires 52, 54 are wound 1.5 turns (540°) around the tubular members 132, 136.

When the wires 52, 54 are rotated, the gear bodies 126, 130 are rotated about the shaft 112. When the gear bodies 126, 130 are rotated at the same speed and in the same direction, the gear body 146 swings with respect to the shaft 112 and moves in a yawing direction. When the gear bodies 126, 130 are rotated at the same speed and in the opposite direction, the gear body 146 is rotated about the second rotational axis Or and moves in a rolling direction. When the gear bodies 126, 130 are rotated at different speeds, the gear body 146 undergoes a composite motion in both yawing and rolling directions. The gear body 126, the gear body 130, and the gear body 146 collectively make up a differential mechanism.

An idle pulley (an idle cylindrical member) 140 is rotatably supported substantially centrally on the shaft 110. A guide pulley (a guide cylindrical member) 142 is rotatably supported substantially centrally on the shaft 112. The idle pulley 140 serves to keep a driven wire 252 wound around the guide pulley 142 through a constant angle (about 180° on both sides) at all times. Instead of using the idle pulley 140, the driven wire 252 may also be wound one or more turns around the guide pulley 142. The idle pulley 140 and the guide pulley 142 may have a smooth surface, and may be made of a material having a small coefficient of friction, in order to reduce slippage and frictional wear on the driven wire 252 (see FIG. 8).

A main shaft 144 is rotatably supported on the shaft 112 between the gear body 126 and the guide pulley 142, as well as between the guide pulley 142 and the gear body 130. The main shaft 144 has a sleeve projecting toward the composite mechanism 102. The main shaft 144 has a square hole 144a formed axially therein. The main shaft 144 includes two auxiliary plates 144b disposed on one end in the Z2 direction for holding both surfaces of the guide pulley 142 in the Y direction. The auxiliary plates 144b have respective holes through which the shaft 112 extends. The auxiliary plates 144b have chevron shapes, which become progressively wider in the Z1 direction, for preventing foreign matter such as threads from entering therein.

The composite mechanism 102 includes an opening/closing mechanism for opening and closing the end effector 104, and a mechanism for changing the attitude of the end effector 104.

The composite mechanism 102 comprises a gear body 146 rotatably fitted over the circumferential surface of the sleeve of the main shaft 144, a nut 148 mounted on the distal end of the main shaft 144, a spring 150, a rod 152 with a square cross-sectional shape and having an end in the Z2 direction, which is inserted into the hole 144a, a driven pulley (a driven cylindrical member) 156 rotatably supported on the end in the Z2 direction of the rod 152 by a pin 154, a driven plate 158, and a hollow cylindrical cover 160. The spring 150 comprises a compression spring. The end in the Z2 direction of the rod 152 is channel-shaped for improving slidability thereof with respect to the driven pulley 156, and the end of the rod 152 projects largely in the Z2 direction.

A thrust bearing 144c made of resin is disposed on the portion of the main shaft 144 that abuts against the gear body 146. A further thrust bearing 148a made of resin is disposed on the portion of the nut 148 that abuts against the gear body 146. The thrust bearings 144c and 148a have a low coefficient of friction, for reducing wear and torque on the abutting portions, and for preventing loads from being applied directly to the face gear 165. The thrust bearings 144c, 148a comprise slide bearings, for example, but may comprise rolling bearings, thereby allowing the manipulator to operate smoothly about the roll axis even when the end effector 104 is strongly closed or opened, i.e., even when the gear body 146 abuts firmly against the main shaft 144.

The gear body 146 is of a stepped shape, comprising a large-diameter portion 162 in the Z2 direction, a small-diameter portion 164 in the Z1 direction, and a face gear 165 on the end of the large-diameter portion 162 in the Z2 direction. The face gear 165 is held in mesh with the gears 134, 138. The gear body 146 prevents the nut 148 from becoming dislodged from the main shaft 144. The large-diameter portion 162 has an externally threaded outer circumferential surface.

The driven plate 158 has a recess 166 in the Z2 direction, an engaging cavity 168 formed in the bottom of the recess 166, axial ribs 170 disposed respectively on both surfaces in the Y direction, and a link hole 172. The engaging cavity 168 has a shape that is engageable with a mushroom-shaped knob 174 on the distal end of the rod 152. When the mushroom-shaped knob 174 engages in the engaging cavity 168, the driven plate 158 and the rod 152 are capable of rotating relatively with respect to each other about the roll axis. The driven plate 158 has a width that is substantially equal to the inside diameter of the cover 160.

The cover 160 has a size that is large enough to cover the composite mechanism 102 substantially in its entirety, and serves to prevent foreign matter (living tissue, medications, threads, etc.) from entering into the composite mechanism 102 and the end effector 104. The cover 160 has two axial grooves 175 formed in an inner circumferential surface thereof in diametrically confronting relation to each other. The ribs 170 of the driven plate 158 are fitted respectively in the grooves 175 for axially guiding the driven plate 158. Since the knob 174 engages in the engaging cavity 168 of the driven plate 158, the driven pulley 156 is axially movable back and forth within the hole 144a, in unison with the driven plate 158 and the rod 152, and can roll about the rod 152. The cover 160 is fixed to the large-diameter portion 162 of the gear body 146 by threaded engagement therewith, or by a press-fitted engagement, or the like.

The spring 150 is fitted between the step of the gear body 146 and the recess 166 of the driven plate 158, for normally biasing the driven plate 158 to move in the Z1 direction into abutment against a stopper.

The end effector 104 comprises a first end effector member 190, a second end effector member 192, and a pin 196. The pin 196 is disposed on the third rotational axis Og.

The first end effector member 190 has a pair of side walls 200 facing each other laterally, holes 200a formed respectively in the distal ends of the side walls 200, and a first gripper 202 projecting in the Z1 direction from the distal ends of the side walls 200. The hole 200a has a diameter such that the pin 196 can be press-fitted into the hole 200a. The first gripper 202 becomes progressively narrower in the Z1 direction and includes an arcuate distal end portion. The first gripper 202 has a number of conical teeth disposed closely together over the entire surface thereof, which faces in the Y1 direction. The first end effector member 190 is coupled to the cover 160 by a given coupling means. For example, the first end effector member 190 and the cover 160 may be of an integral structure, providing a composite tubular body 230.

The cover 160 is coupled at a proximal portion to the gear body 146 (by threaded engagement, press-fitted engagement, welding, or the like). When the gear body 146 is rotated, the cover 160 and the first end effector member 190 operate about the roll axis.

The second end effector member 192 is L-shaped, comprising a second gripper 212 extending in the Z direction, and a lever 214 bent about 60° with respect to the second gripper 212. The second end effector member 192 has a hole 216 formed in the L-shaped bent corner, and the lever 214 has a hole 218 formed therein near to the end portion thereof. When the pin 196 is inserted into the hole 216, the second end effector member 192 is swingable about the third rotational axis Og. The second gripper 212 has a shape that is identical to the first gripper 202, yet is disposed in an inverted fashion. When the second end effector member 192 is angularly moved about the third rotational axis Og, the second end effector member 192 abuts against the first gripper 202 for gripping a curved needle or the like.

The lever 214 and the driven plate 158 are joined to each other by two parallel gripper links 220. Specifically, a pin 222 is inserted into holes 220a formed in respective ends of the gripper links 220 and the hole 218, whereas a pin 224 is inserted into holes 220b formed respectively in other ends of the gripper links 220 and the hole 172.

Figure 5:
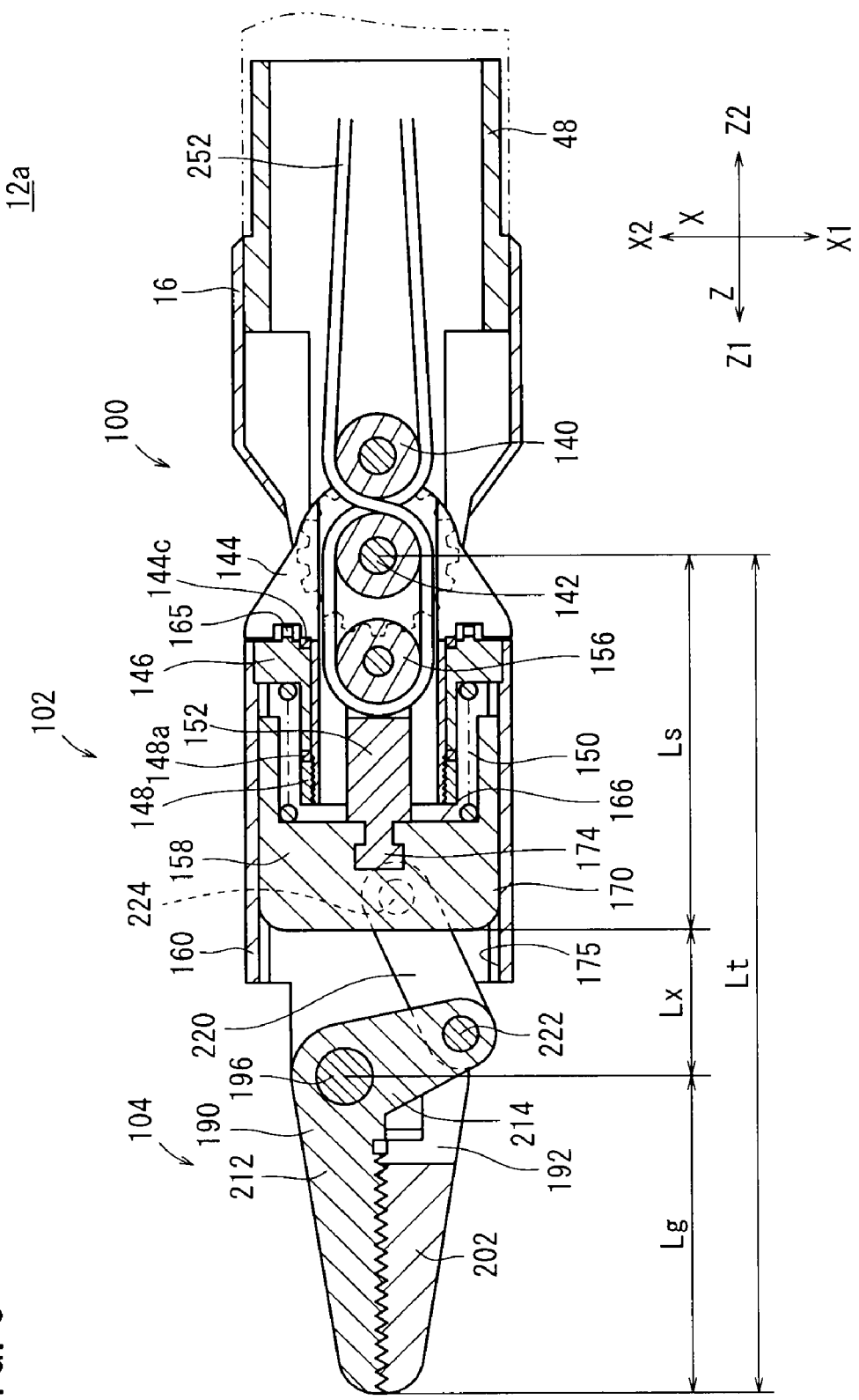
FIG. 5 is a sectional plan view of the distal end working unit according to the first embodiment, with a gripper being closed.

The position of the pin 224, by which the gripper links 220 are pivotally supported, is slightly offset from the central axis in FIG. 5 (as viewed in plan). However, the pin 224 may be positioned on the central axis as viewed in plan. The position of the pin 224 may be determined in view of the balance of acting forces, the space, and the ease with which to assemble the parts. The pins may be integrally combined with the gripper links 220.

Two gripper links 220 are disposed in parallel to each other, for adequately balancing the forces, and for preventing the application of inadvertent moment loads. Depending on design conditions, only one gripper link may be employed.

When the driven pulley 156, the rod 152, and the driven plate 158 are moved in the Z2 direction, the lever 214 also is pulled in the Z2 direction, causing the second gripper 212 to move toward the first gripper 202 so as to grip an object therebetween. Conversely, when the driven pulley 156, the rod 152, and the driven plate 158 are moved in the Z1 direction by action of the spring 150, the lever 214 also is pushed in the Z1 direction, causing the second gripper 212 to move away from the first gripper 202 and open the end effector 104. Since the driven plate 158 is normally biased by the spring 150 to move in the Z1 direction, when the manipulator is not manually operated, the second gripper 212 is spaced from the first gripper 202 thereby opening the end effector 104. The spring 150 is effective to keep the wire 56 and the driven wire 252 under a suitable tension and prevent them from sagging. Therefore, play between the various parts is prevented and the manipulator is capable of gripping objects with high responsiveness.

For the sake of brevity, the term "end effector 104" will hereinafter be used to refer to the first gripper 202 and the second gripper 212.

Figure 7:
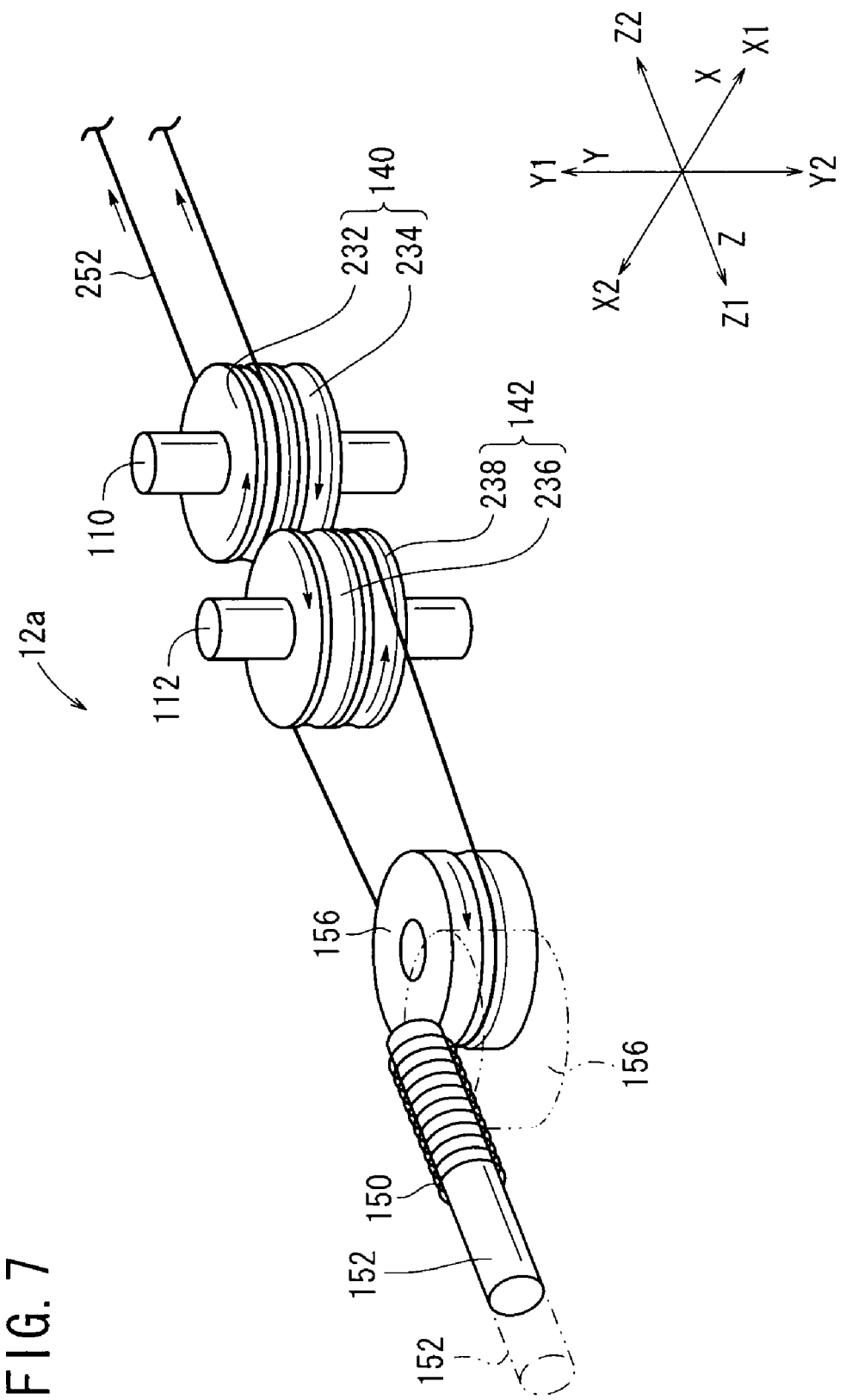
FIG. 7 is a schematic structural view of the distal end working unit according to the first embodiment.

As shown in FIG. 7, the idle pulley 140 comprises two parallel pulleys, i.e., a first layer idle pulley (first layer idle cylindrical body) 232 and a second layer idle pulley (second layer idle cylindrical body) 234, which are aligned coaxially with each other. The guide pulley 142 comprises two parallel pulleys, i.e., a first layer guide pulley (first layer guide cylindrical body) 236 and a second layer guide pulley (second layer guide cylindrical body) 238, which are aligned coaxially with each other.

At the end in the Z2 direction in FIG. 7, one of the stretches of the driven wire 252 is held against surfaces of the first layer idle pulley 232 in the X1 and Z1 directions, and also is held against surfaces of the first layer guide pulley 236 in the Z2 and X2 directions, while extending to the driven pulley 156.

At the end in the Z2 direction in FIG. 7, the other stretch of the driven wire 252 is held against surfaces of the second layer idle pulley 234 in the X2 and Z1 directions, and also is held against surfaces of the second layer guide pulley 238 in the Z2 and X1 directions, while extending to the driven pulley 156.

When the wire 56 (see FIG. 8) is pulled in the Z2 direction, for example, the first layer idle pulley 232 and the second layer guide pulley 238 are rotated counterclockwise as viewed in plan, whereas the second layer idle pulley 234 and the first layer guide pulley 236 are rotated clockwise as viewed in plan. Since each of the idle pulley 140 and the guide pulley 142 comprises two parallel coaxial pulleys, the pulleys are rotatable in opposite directions when the driven wire 252 held thereagainst is moved, and hence the pulleys operate smoothly.

Figure 8:
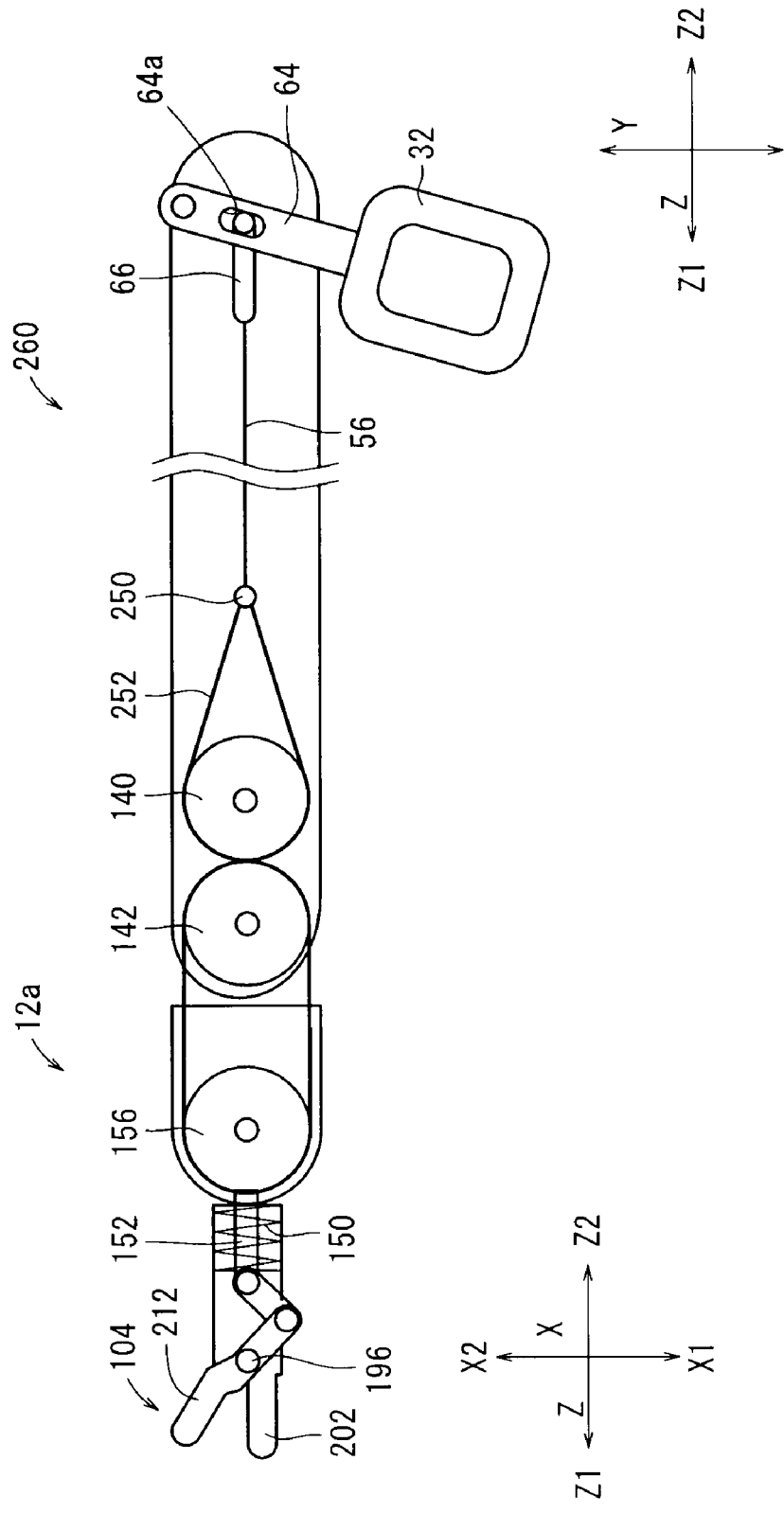
FIG. 8 is a schematic side elevational view of the distal end working unit according to the first embodiment, with a trigger lever being in a non-operated state.

As shown in FIG. 8, the end of the wire 56 in the Z1 direction is connected to both ends of the driven wire (a flexible member) 252 by a terminal 250 (or welding, through hole, etc.). The driven wire 252 is in the form of a ring-like flexible member, having a portion thereof connected to the wire 56, and may alternatively comprise a rope, a resin wire, a piano wire, a chain, or the like. The term "ring-shaped" should be interpreted in a broad sense. The flexible member does not necessarily need to be applied to the entire length. That is, at least the portion of the driven wire 252, which is wound around each of the pulleys, may be a flexible member with the linear portion thereof being connected by a rigid member. The driven wire 252 may make up part of the wire 56.

The driven wire 252 passes from the wire 56, serving as a drive member, along the idle pulley 140 in the X1 direction (first side) and extends to the X2 direction (second side), and then passes along the guide pulley 142 in the X2 direction and extends to the surface of the driven pulley 156 in the X2 direction. The driven wire 252 is then wound in a half turn around the surface of the driven pulley 156 in the Z1 direction and extends to the surface thereof in the X1 direction, and while oriented in the X2 direction, the driven wire 252 passes along the idle pulley 140 in the X2 direction and extends to the terminal 250.

The driven wire 252 thus passes through a circulatory path, having its starting and ending points at the terminal 250. The driven wire 252 passes along both sides of the idle pulley 140 and is wound around the driven pulley 156, while crossing over itself between the idle pulley 140 and the guide pulley 142, thereby making up a substantially 8-shaped configuration. The terminal 250 and the driven wire 252 are mechanically connected to the trigger lever 32 by the wire 56.

The term "mechanically" refers to a system for actuating members via a mechanical component, in the form of a solid body that is nonelastic in the power transmitting direction. Although the wire 56 is a flexible member, it is appropriately tensioned by the spring 150. For closing the end effector 104, the wire 56 is pulled in the Z2 direction by the trigger lever 32 and essentially is not elastically deformed, or inevitably is elastically deformed only to an extent that is trouble-free in operation, thereby providing a mechanical connecting means. The driven wire 252 crosses over itself as viewed in plan.

The idle pulley 140, the guide pulley 142, and the driven pulley 156 have substantially the same diameter, which is a sufficiently large diameter, to the extent possible by the layout, such that the driven wire 252 will not become bent. The terminal 250 is disposed in a position appropriately spaced from the idle pulley 140, so that the driven wire 252 will not be bent excessively. Both ends of the driven wire 252 form an acute angle at the terminal 250. Since the spring 150 (see FIG. 4) biases the driven plate 158 to move in the Z1 direction, the driven pulley 156 and the driven plate 158 undergo forces in the Z1 direction. The driven wire 252 and the wire 56 are thus placed appropriately in a state of tension, and are not slackened. The gap between the idle pulley 140 and the guide pulley 142 is small, e.g., substantially the same as the width of the driven wire 252.

The idle pulley 140, the guide pulley 142, and the driven pulley 156 may have flanges on upper and lower surfaces thereof, or may have concave side surfaces for preventing the driven wire 252 from dropping off.

For illustrative purposes, the wire 56, the driven wire 252, the idle pulley 140, the guide pulley 142, the driven pulley 156, and the end effector 104, shall be referred to collectively as an end effector driving mechanism 260. In the end effector driving mechanism 260, as shown in FIG. 8, the driven wire 252, the idle pulley 140, the guide pulley 142, and the driven pulley 156 are arranged along the central line from a proximal end to a distal end. The end effector 104 is coupled to the driven pulley 156 by the rod 152.

Operation of the manipulator 10 thus constructed shall be described below.

As shown in FIG. 8, when the trigger lever 32 is not touched, the end effector 104 is opened under the resiliency of the spring 150. The X direction in FIGS. 8, 9, 10, 11, 22, 23, 38, 39, and 41 is indicated with respect to the distal end working unit 12a, and the vertical direction of the trigger lever 32 corresponds to the Y directions.

Figure 9:
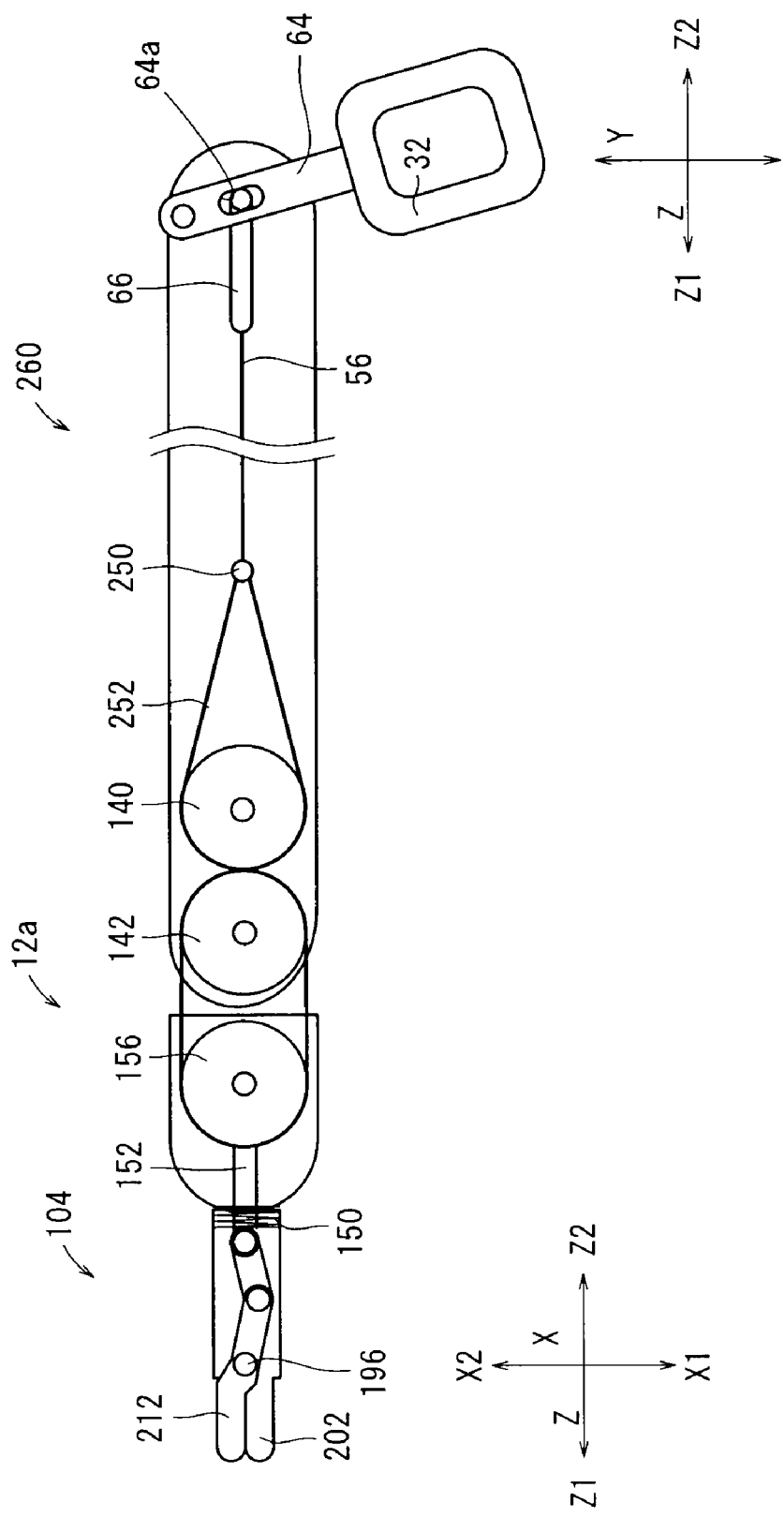
FIG. 9 is a schematic side elevational view of the distal end working unit according to the first embodiment, with the trigger lever being fully pulled.

As shown in FIG. 9, when the trigger lever 32 is fully pulled by hand, the wire 56 pulls the driven wire 252, moving the driven pulley 156 and the rod 152 in the Z2 direction while compressing the spring 150, thereby closing the end effector 104. At this time, the trigger lever 32 requires forces for compressing the spring 150. For opening the end effector 104, the force applied to the trigger lever 32 is released, thereby allowing the rod 152 to be pushed toward the distal end under the restorative force of the spring 150, and returning the end effector 104 to the open state.

Since the driven wire 252 is ring-shaped, it provides two left and right stretches. Therefore, the forces applied to close the end effector 104 are divided into substantially equal forces, which act as tensile forces on respective stretches of the driven wire 252. Therefore, the driven wire 252 may have a diameter that is smaller than the wire 56, and may be sufficiently flexible.

Figure 10:
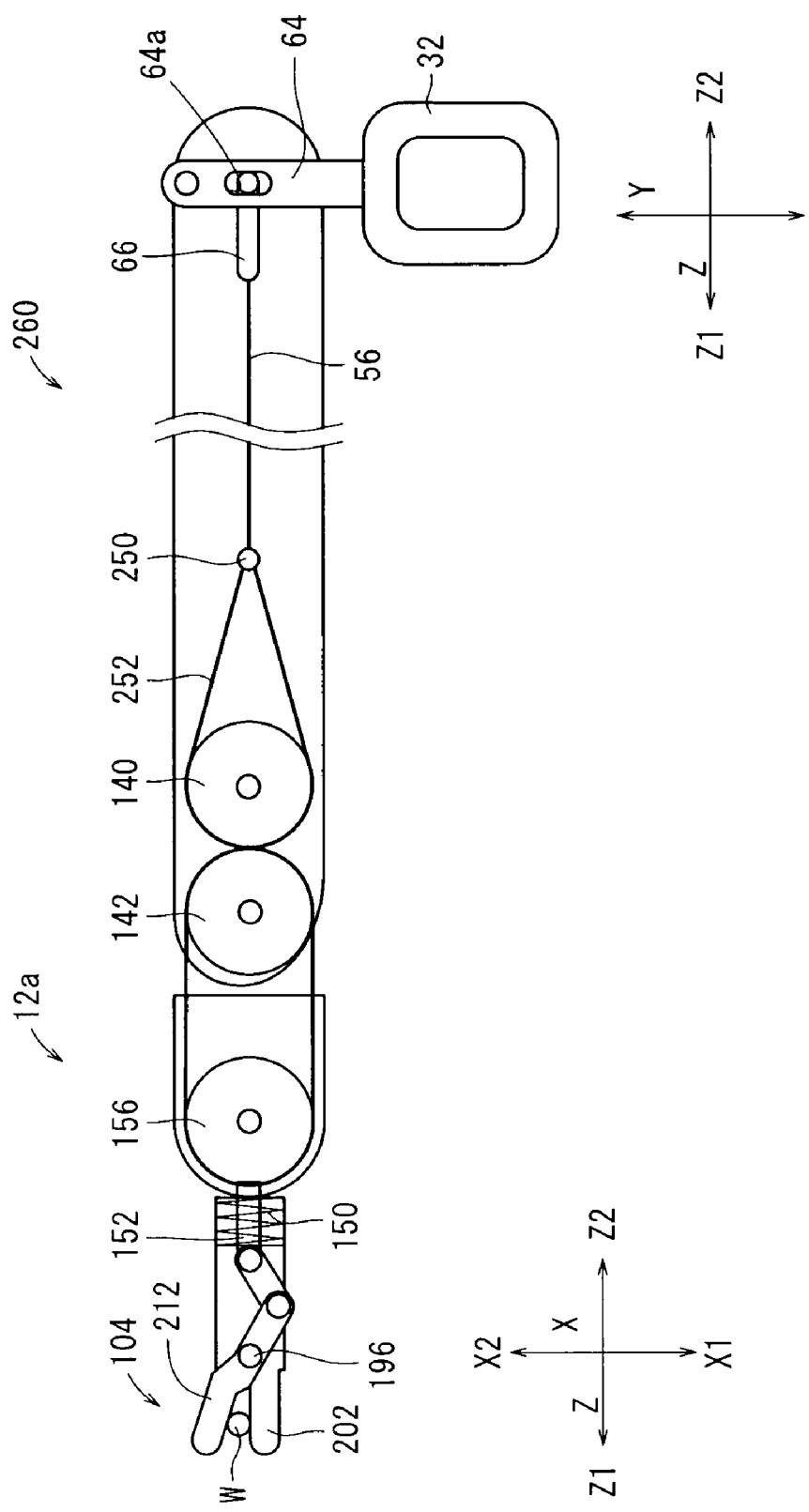
FIG. 10 is a schematic side elevational view of the distal end working unit according to the first embodiment, with the trigger lever being pulled to an intermediate position.

As shown in FIG. 10, when the end effector 104 grips an object (a surgical instrument, a living tissue, or the like) W at the time the trigger lever 32 is pulled to a certain extent by the hand, the end effector 104, the driven plate 158, the rod 152, and the driven pulley 156 are essentially no longer moved further, or are moved only a distance corresponding to the elastic deformation of the driven wire 252 and other components and the elastic deformation of the object W. The driven wire 252, the wire 56, and the trigger lever 32 are not moved further in the Z2 direction, thereby allowing the operator to feel, with the fingertip, that the end effector 104 has gripped the object W.

If the object W is a hard object such as a surgical instrument or the like, then the trigger lever 32 is essentially unable to move in the Z2 direction. The operator can thus feel that the end effector 104 has gripped something hard, and the end effector 104 can reliably grip the object W with strong forces, because the operator can transmit manual forces mechanically and directly to the end effector 104, rather than via electromagnetic means. If gripping forces equivalent to such manual forces were to be generated by a motor, then the motor would need to be considerably large and heavy, and could not be housed readily inside the actuator block 30, and further, would make the manipulator 10 heavier.

If the object W is a soft object such as a living tissue or the like, then the trigger lever 32 is slightly displaceable in the Z2 direction depending on the resiliency of the object W. The operator can thus feel that the end effector 104 has gripped something soft, and can recognize how soft the object W is as well as adjust the forces with which the object W is gripped.

When the wires, etc., are worn or become degraded, friction increases and is transmitted to the trigger lever 32, allowing the operator to sense a change in state, or an abnormal state, of the drive system. Hence, the operator can judge the timing of maintenance more appropriately.

Figure 11:
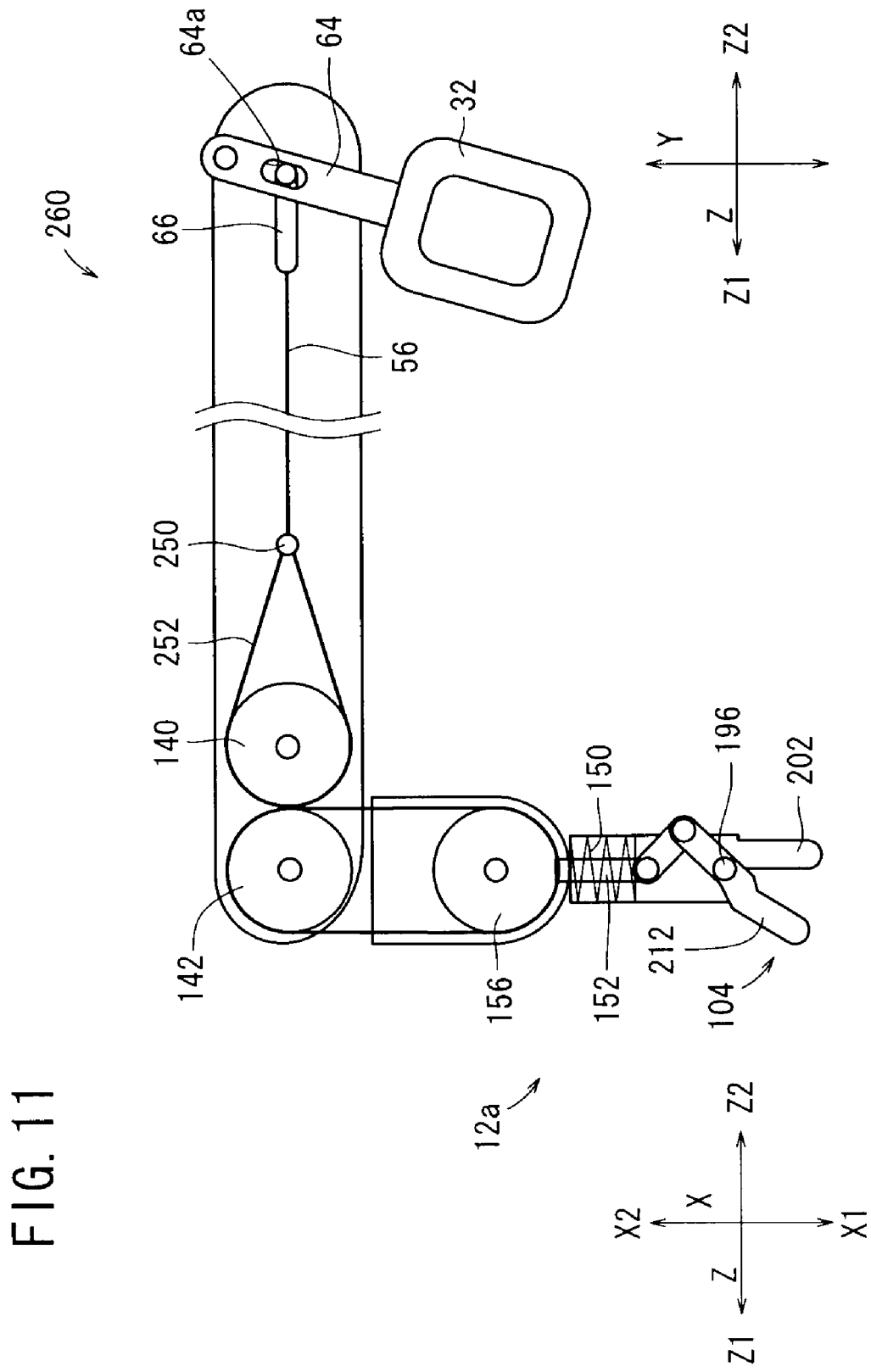
FIG. 11 is a schematic side elevational view of the distal end working unit according to the first embodiment, with a roll axis being operated in one direction.

As shown in FIG. 11, when the end effector 104 is operated about the yaw axis, the driven pulley 156 rotates about itself, while revolving around the guide pulley 142. Since the distance between the driven pulley 156 and the guide pulley 142 remains unchanged, the rod 152 is not relatively actuated and there is no mechanical interference. When the end effector 104 is operated about the roll axis, since the rod 152 is disposed so as to pass through the center of the roll axis, the rod 152 is not actuated and there is no mechanical interference. In other words, the end effector driving mechanism 260 provides a non-interfering construction.

Since the idle pulley 140 and the guide pulley 142 are sufficiently close to each other, even when the end effector 104 is actuated 90° about the yaw axis, the angle through which the driven wire 252 is wound around the driven pulley 156 remains essentially unchanged, and substantially no torque that interferes with the yaw and roll axes is generated in response to the gripping action.

If the idle pulley 140 and the guide pulley 142 are spaced from each other by a certain distance, then when the end effector 104 is operated significantly about the roll axis, the driven wire 252 is spaced from one of the surfaces of the guide pulley 142. The driven wire 252 is thus brought out of balance in the X direction (reference state) about the yaw axis, producing an interference torque about the yaw axis. For maximizing the operating range about the yaw axis, it is desirable to position the idle pulley 140 and the guide pulley 142 sufficiently close to each other. Actually, inasmuch as the driven wire 252 passes between the idle pulley 140 and the guide pulley 142, a certain gap is needed therebetween. Also, the gap between portions of those pulleys (except for the flanges on the upper and lower surfaces) around which the driven wire 252 is wound may be of a size that is 1 to 2 times the thickness of the driven wire 252.

If the operating range about the yaw axis does not need to be increased, then the idle pulley 140 and the guide pulley 142 may be appropriately spaced from each other. Even if the yaw axis is bent, the end effector 104 can be opened and closed by operating the trigger lever 32, so as to cause the driven wire 252 to actuate the driven pulley 156.

As the yaw-axis operation and the roll-axis operation do not cause mechanical interference with opening and closing operations of the end effector 104, the drive mechanism of the distal end working unit 12a for actuating the end effector 104 does not require any correcting means for compensating for interference, or any other type of correcting means (e.g., corrective actuators and assisting mechanisms) including mechanisms and actuators. Therefore, the manipulator 10 is simple and lightweight in structure. Operating forces applied to the trigger lever 32 can efficiently be transmitted to the end effector 104 without affecting other drive systems. Consequently, the end effector 104 can exert strong gripping (or peeling) forces. Inasmuch as the manipulator 10 is lightweight, the operator can reduce the forces needed to support the manipulator 10. As a result, the manipulator 10 enables the operator to perform techniques suitably over a long period of time, and also to better feel the forces at which tissue is pierced with a suture needle, along with reactive forces from the tissue.

The manipulator 10 is an energy saver because the end effector 104 can be opened and closed manually by the trigger lever 32.

A link mechanism, which is a reversal of the above link mechanism, may be used, such that the end effector 104 is closed when it is not operated on by the hand. In this case, the end effector 104 can be opened when the trigger lever 32 is pulled. The reversal link mechanism may be such that the closed state of the end effector 104, i.e., the state in which the second gripper 212 is superposed on the first gripper 202, as shown in FIG. 8 for example, is an initial state. When the trigger lever 32 is pulled in the initial state, the second gripper 212 is turned counterclockwise and spaced from the first gripper 202, thereby opening the end effector 104.

During surgical operations, a large peeling force may be required in a direction (peeling direction) to open the end effector 104, for the purpose of peeling off tissue. If the pulling action of the trigger lever 32 is directly transmitted to the end effector 104 through the reversal link structure, then a large peeling force can be produced.

In this case, with the manipulator 10, the forces in the opening direction of the end effector 104 are transmitted to the trigger lever 32. In other words, when the end effector 104 is opened and abuts against living tissue, a surgical instrument, or the like, in the opening direction, the trigger lever 32 is unable to move in the Z1 direction. The operator thus can sense that the end effector 104 abuts against something.

Since the difference between the yaw axis and the pitch axis of the distal end working unit 12 represents an initial attitude or a relative attitude with respect to the operating unit, the yaw axis may be replaced with the pitch axis. Therefore, the distal end working unit 12 may have the yaw axis and the pitch axis. The attitude axes (corresponding to the yaw axis and the roll axis on the distal end working unit 12) may be actuated by rods, links, torque tubes, or the like, for example, or any combination thereof, rather than by means of wires (flexible members) and gears.

The idle pulley 140, the guide pulley 142, and the driven pulley 156 may not necessarily be pulleys, but may comprise cylindrical bodies around which wires can be wound, if they allow the flexible member to slip thereon. The cylindrical bodies are to be interpreted in a broad sense, and include hollow cylindrical bodies and arcuate columnar bodies. If the angle of the operational range of a pulley is small according to design conditions, then the wire may be wound in less than one turn around the pulley. In this case, the pulley may be an arcuate columnar body.

If the driven pulley 156 is nonrotatable with respect to the pin 154 (the driven pulley 156 is fixed to the rod 152), then since the driven wire 252 is not held in abutment against a semiarcuate portion of the driven pulley 156 that is closer to the guide pulley (in the Z2 direction), the semiarcuate portion of the driven pulley 156 is not required, and hence the driven pulley 156 may be in the form of a cylindrical body, having only a semiarcuate portion closer to the distal end thereof. If a return pulley 350, similarly, has a portion held out of abutment against the driven wire 252, then the return pulley 350 may be a partly arcuate cylindrical body, thereby enabling the composite mechanism 102 to be reduced in length.

Modifications of the junction at the end of the driven wire 252, which correspond to the terminal 250, shall be described below with reference to FIGS. 12 to 17.

Figure 12:
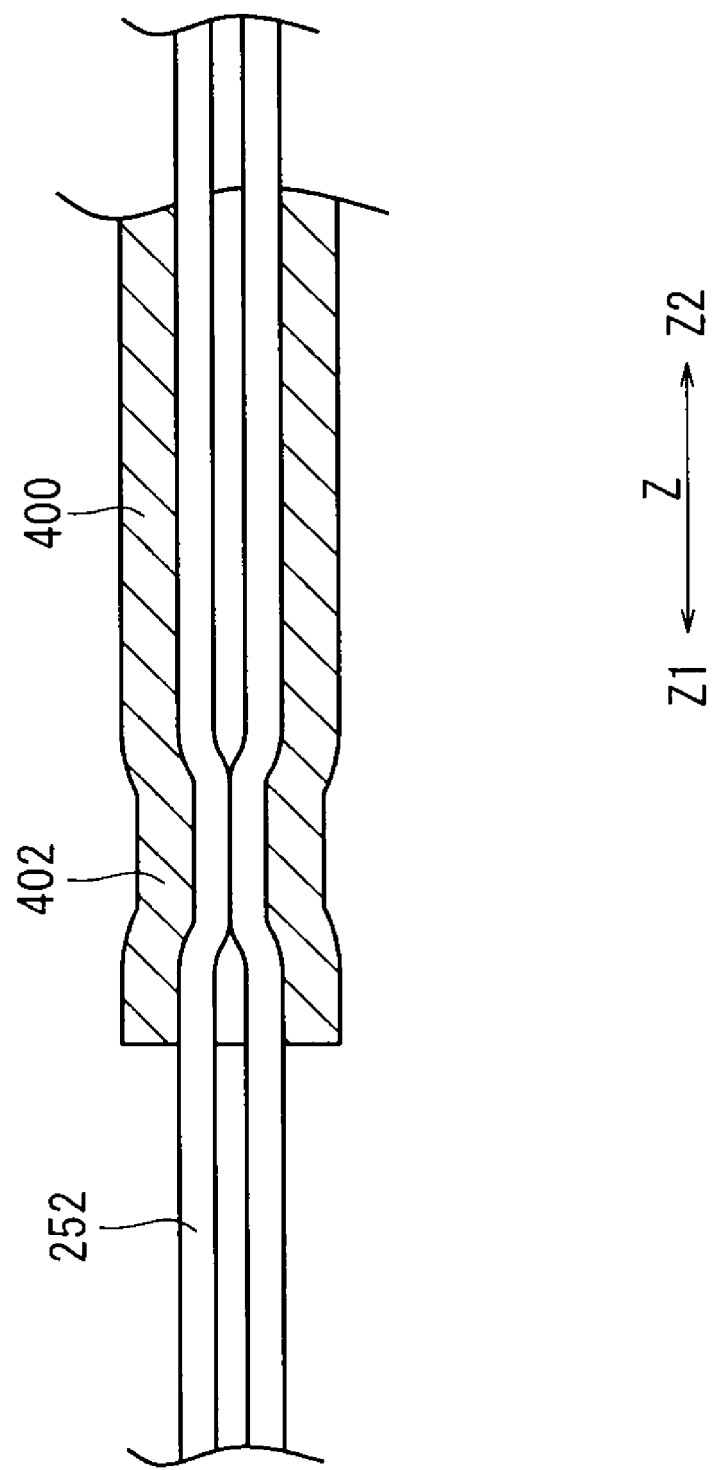
FIG. 12 is a schematic view of a connected portion of an end of a passive wire according to a first modification.

According to a first modification of the function at the end of the driven wire 252, as shown in FIG. 12, both ends of the driven wire 252 are inserted into the opening at the distal end of a pipe (drive member) 400, and a portion 402 proximate the opening at the distal end is pressed so as to compress the inserted ends. The driven wire 252 can thus be secured in place easily.

Figure 13:
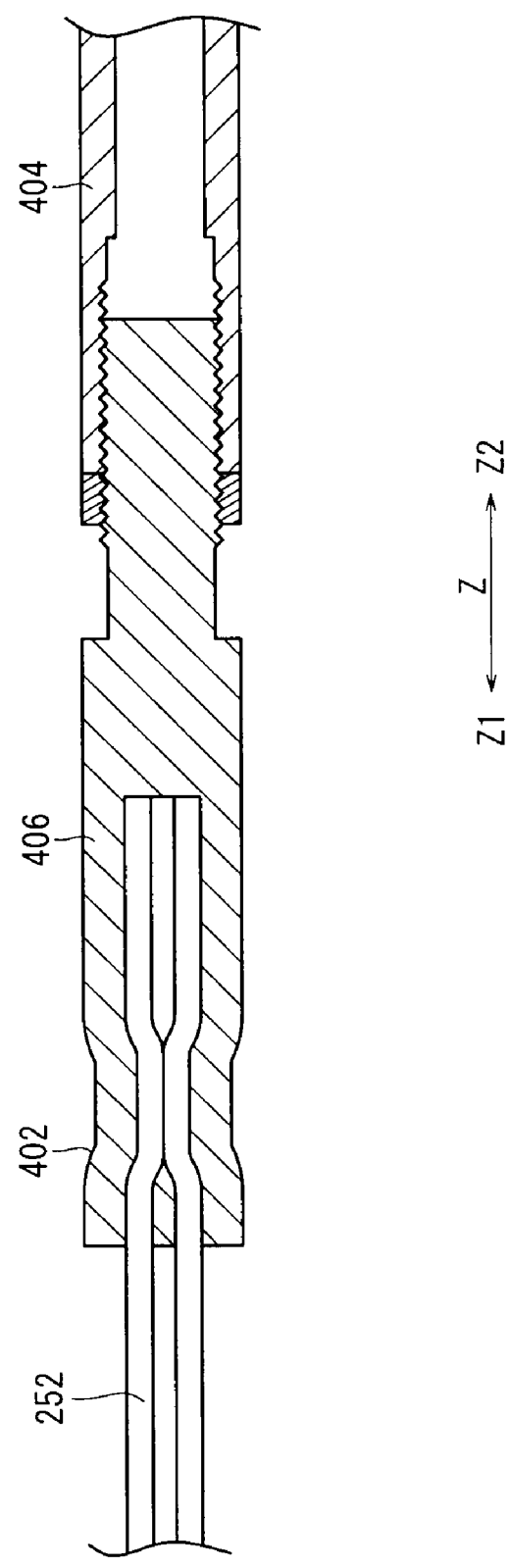
FIG. 13 is a schematic view of a connected portion of an end of a passive wire according to a second modification.

According to a second modification of the function at the end of the driven wire 252, as shown in FIG. 13, a pipe 406 is threaded into the distal end of a rod (drive member) 404. Similar to the pipe 400 shown in FIG. 12, the pipe 406 compresses both ends of the driven wire 252. Thus, with this arrangement, the rod 404 and the pipe 406 are detachably connected to each other, for facilitating assembly and maintenance. Such threaded engagement allows the pipe 406 to project adjustably from the rod 404, for adjusting the length and tension of the driven wire 252. The pipe 406 may further be secured by a double-nut structure.

Figure 14:
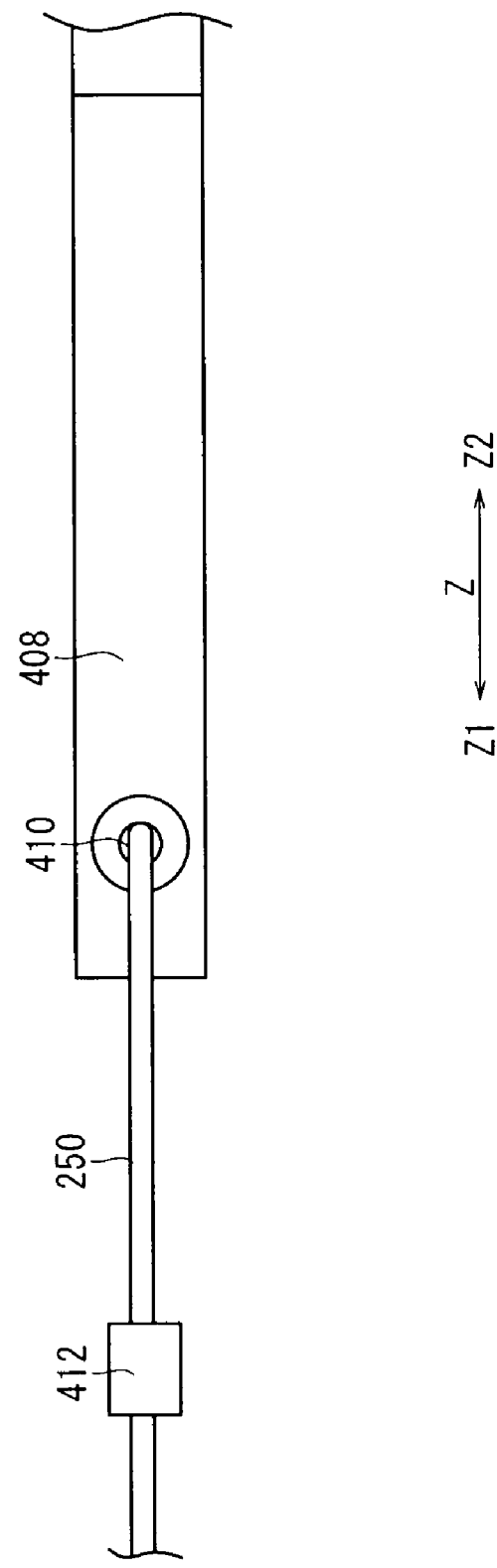
FIG. 14 is a schematic plan view of a connected portion of an end of a passive wire according to a third modification.
Figure 15:
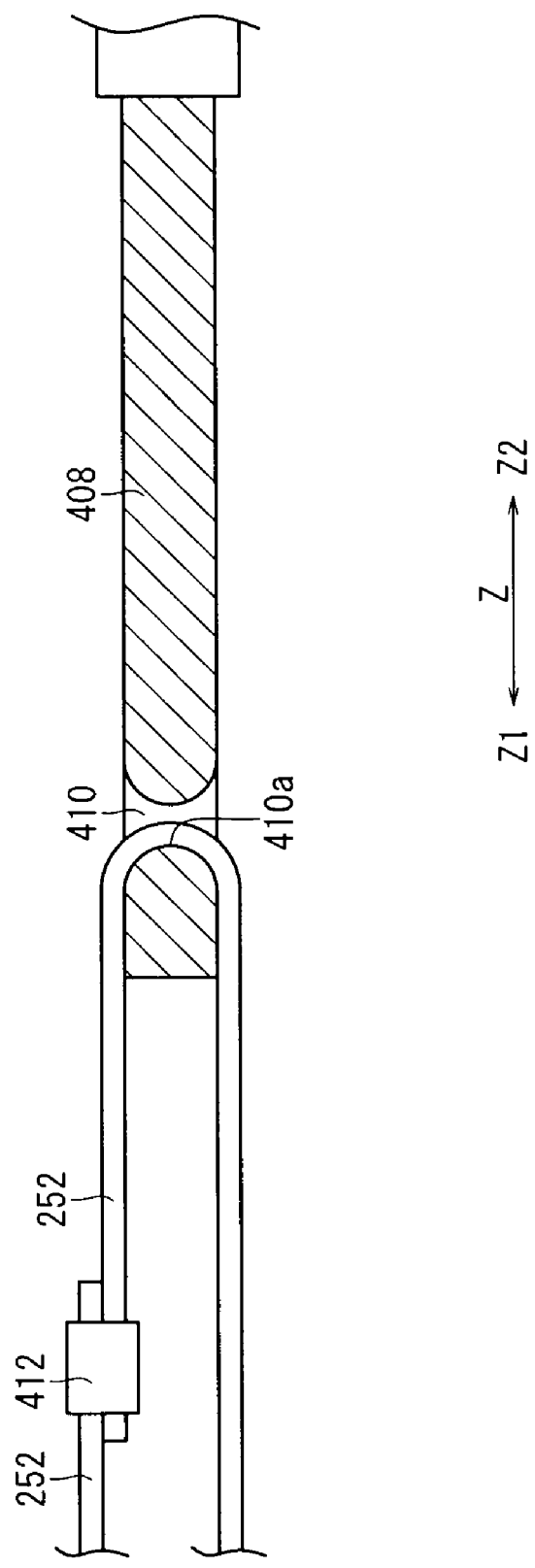
FIG. 15 is a schematic sectional side elevational view of the connected portion of the end of the passive wire according to the third modification.

According to a third modification of the function at the end of the driven wire 252, as shown in FIGS. 14 and 15, the driven wire 252 is inserted through a hole 410 formed in the distal end of a rod (drive member) 408. The hole 410 has an arcuate wall 410a facing in the Z2 direction, which is engaged by the driven wire 252. The driven wire 252 slides against the arcuate wall 410a. When the rod 408 is pulled in the Z2 direction, the driven wire 252 can be pulled in the X direction with good balance.

The driven wire 252, which comprises a single wire, has both ends thereof fixed to a securing member 412, and hence is of a ring shape. The securing member 412 is disposed in a location other than the junction to the rod 408 as a drive member, and allows the length and tension of the driven wire 252 to be adjusted. Hence, the third modification is simple in structure.

Figure 16:
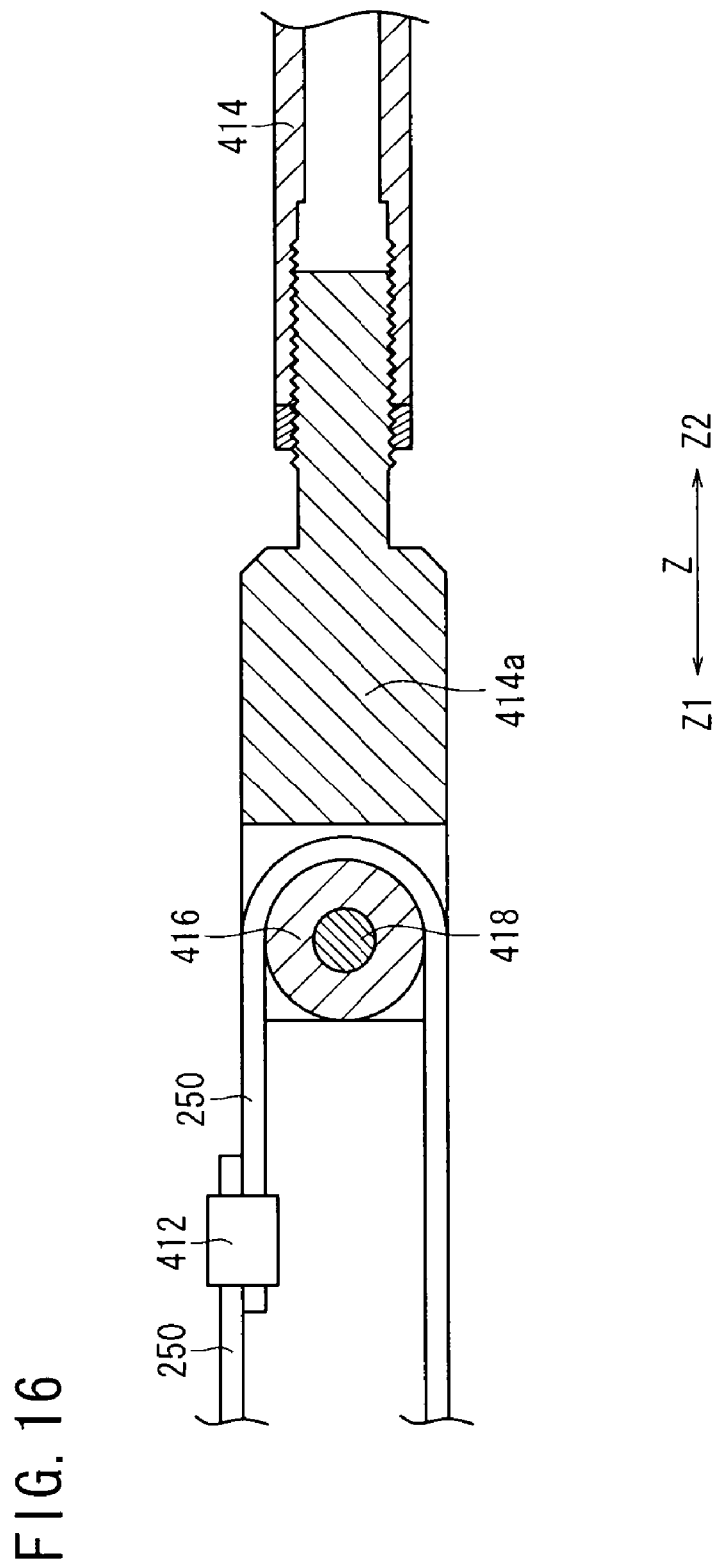
FIG. 16 is a schematic sectional plan view of a connected portion of an end of a passive wire according to a fourth modification.
Figure 17:
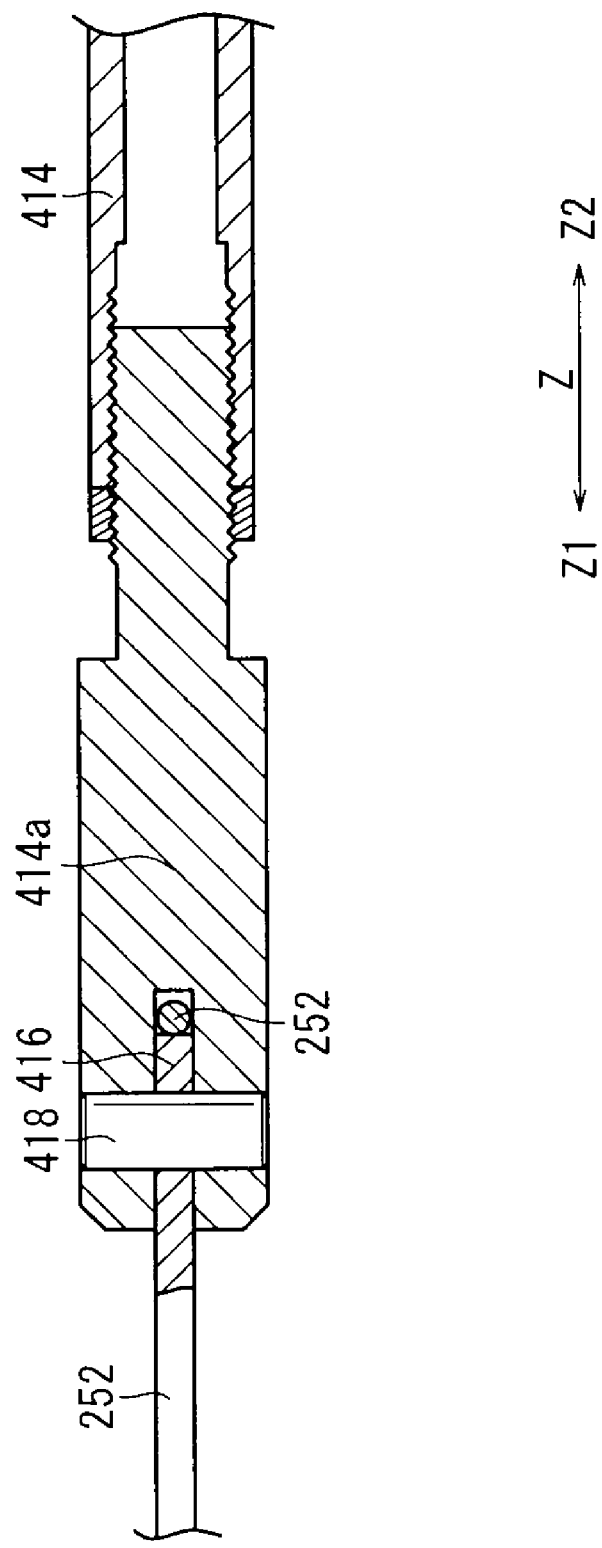
FIG. 17 is a schematic sectional side elevational view of the connected portion of the end of the passive wire according to the fourth modification.

According to a fourth modification of the function at the end of the driven wire 252, as shown in FIGS. 16 and 17, a roller 416 is mounted at a distal end portion 414a of a rod (drive member) 414, and the driven wire 252 is wound around the roller 416. The roller 416 is rotatably supported on a pin 418. The driven wire 252, as it is wound around the roller 416, is movable back and forth. When the rod 414 is pulled in the Z2 direction, the driven wire 252 can be pulled in the X direction with good balance, even if the yaw axis is not bent. The distal end portion 414a is threaded into the rod 414. According to the fourth modification, the paired stretches of the driven wire 252, which are spaced in the Y direction, are tensioned uniformly so as to lengthen the service life of the driven wire 252 and to make the paired stretches of the driven wire 252 parallel to each other.

Since the paired stretches of the driven wire 252, which are spaced in the Y direction, are parallel to each other, the rod 414 may be disposed in a position close to the distal end working unit 12a, thereby shortening the driven wire 252 and reducing elongation of the driven wire 252, so as to increase the responsiveness thereof.

A distal end working unit 12b according to a second embodiment will be described below. Those parts of the distal end working unit 12b (as well as the distal end working units 12c through 12f) that are identical to those of the distal end working unit 12a shall be denoted by identical reference characters, and these features will not be described in detail below.

Figure 18:
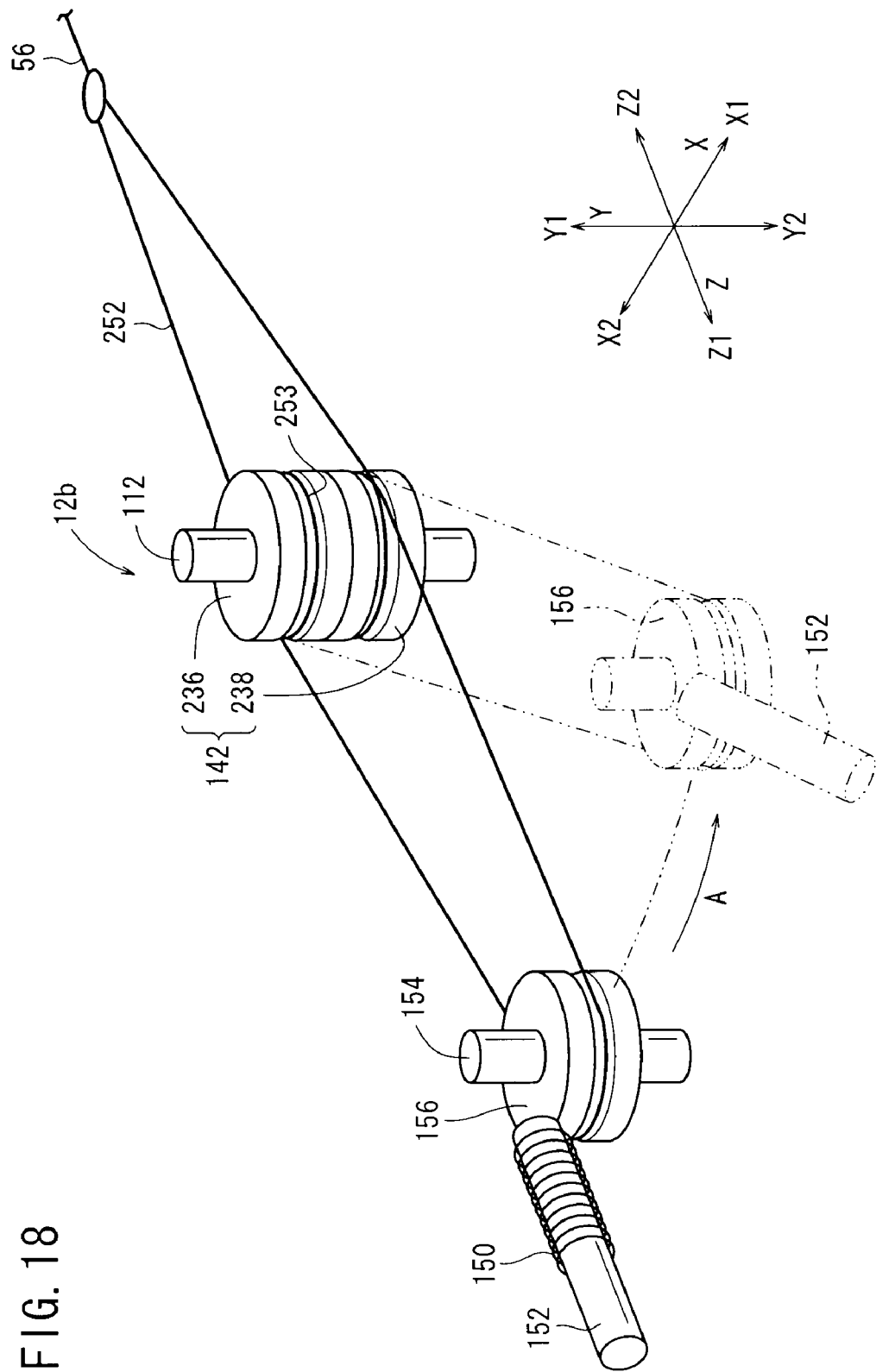
FIG. 18 is a schematic structural view of a distal end working unit according to a second embodiment.

As shown in FIG. 18, the distal end working unit 12b is of a structure that is similar to the distal end working unit 12a, except that the idle pulley 140 (see FIG. 7) is dispensed with. In the distal end working unit 12b, the driven wire 252 is wound in one turn or more around the guide pulley 142 from two directions. Specifically, the driven wire 252 is wound around the first layer guide pulley 236 from the X2 direction, and is wound around the second layer guide pulley 238 from the X1 direction. The distal end working unit 12b operates in the same manner as the distal end working unit 12a. When the driven wire 252 is pulled in the Z2 direction, the guide pulley 142 and the driven pulley 156 are pulled to operate the end effector 104, and also to operate the end effector 104 in the yawing directions, about the shaft 112 (see the imaginary lines in FIG. 18). If the operation range about the yaw axis is one-sided (0° to 90°), then only one stretch of the driven wire 252 may be wound in one turn or more around the guide pulley 142. For example, in FIG. 18, in order to operate the end effector 104 only in one direction, as indicated by the arrow A, about the yaw axis, the turn 253 of the driven wire 252, which is wound around the first layer guide pulley 236 in the X1 direction, is not required. The driven wire 252 may be held only against the surface of the first layer guide pulley 236, which faces in the X2 direction.

The distal end working unit 12b is simpler in structure than the distal end working unit 12a, because it does not require the idle pulley 140. On the other hand, with the distal end working unit 12a, the length of the driven wire 252, which is wound around the guide pulley 142, is shorter for providing less friction, and the overall length of the driven wire 252 is shorter than in the case of the distal end working unit 12b. Since the number of turns around the guide pulley 142 is smaller, the guide pulley 142 may be thinner. Whether the distal end working unit 12a or the distal end working unit 12b is to be employed may be determined depending on design conditions.

The structures shown in FIGS. 12 to 18 are also applicable to the distal end working units 12c through 12f, to be described below.

The distal end working unit 12c according to a third embodiment will be described below.

Figure 19:
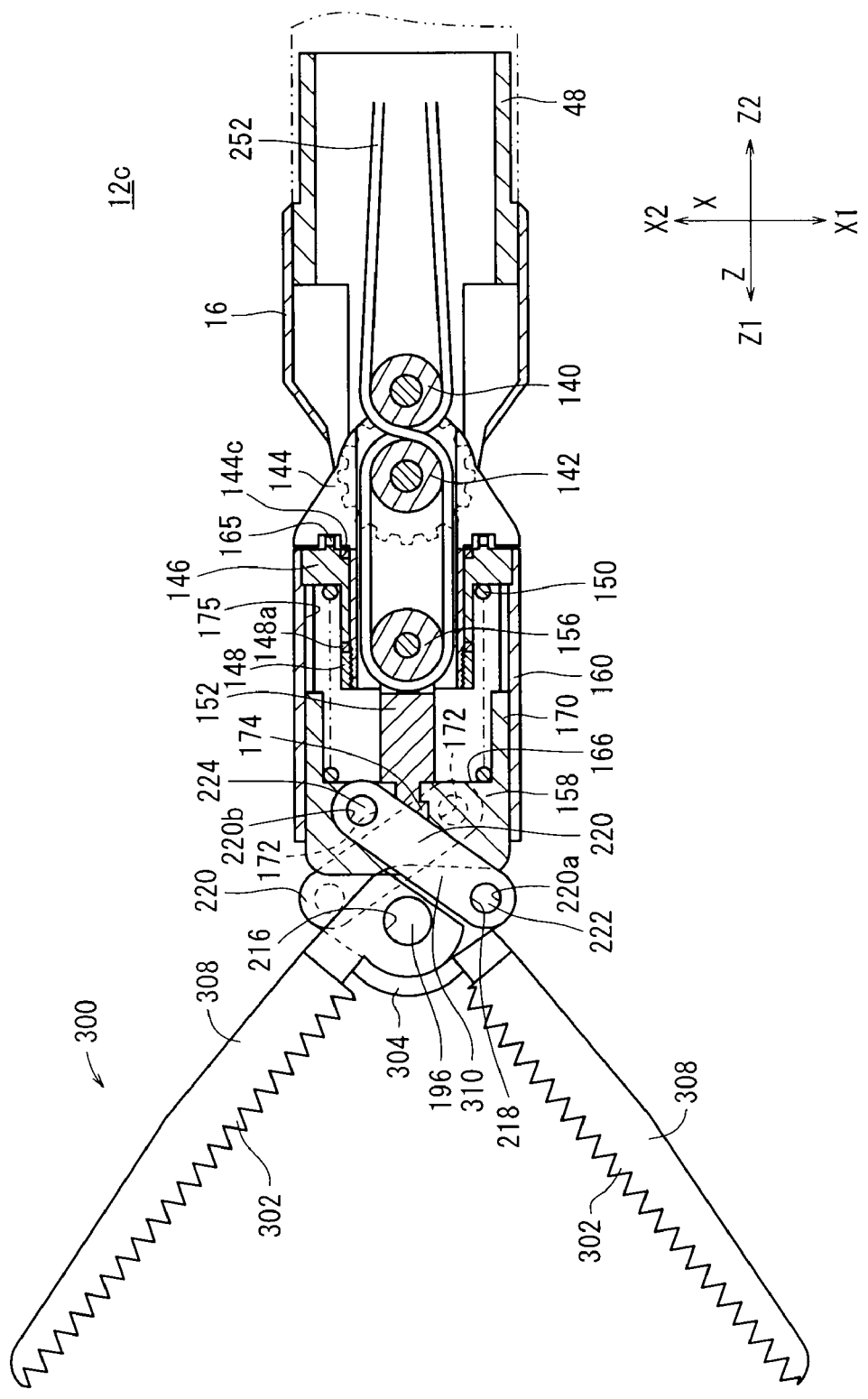
FIG. 19 is a sectional plan view of a distal end working unit according to a third embodiment.

As shown in FIG. 19, the distal end working unit 12c is different from the distal end working unit 12a in terms of the structure of the end effector 104.

The distal end working unit 12c includes an end effector 300 having a double-sided-open type structure, with a pair of grippers 302 being movable thereon. The end effector 300 comprises a gripper base 304 integrally combined with the cover 160, a pair of end effector members 308 movable about a pin 196 mounted on the gripper base 304, and a pair of gripper links 220.

Each of the end effector members 308 has an L shape, similar to the second end effector member 192, and comprises a gripper 302 extending in the Z1 direction and a lever 310 bent about 35° and extending from the gripper 302. The L-shaped bent corner includes a hole 216 formed therein, and the pin 196 is inserted into the hole 216, so that the end effector members 308 are swingable about the third rotational axis Og. The lever 310 has a hole 218 formed therein near to the end portion thereof.

Each of the end effector members 308 is coupled to a pin 224 on the driven plate 158 by a single side gripper link 220. The driven plate 158 has two link holes 172 disposed in symmetrical positions with respect to the X direction in FIG. 19. The gripper links 220 cross each other, as viewed in plan.

The wire-driven mechanism 100 and the composite mechanism 102, other than the end effector 300 of the distal end working unit 12c, are identical in structure to those of the distal end working unit 12a described above.

Since the grippers 302 are disposed in confronting positions, the distal end working unit 12c is capable of exerting well-balanced forces, without imposing inadvertent moment loads.

Figure 20:
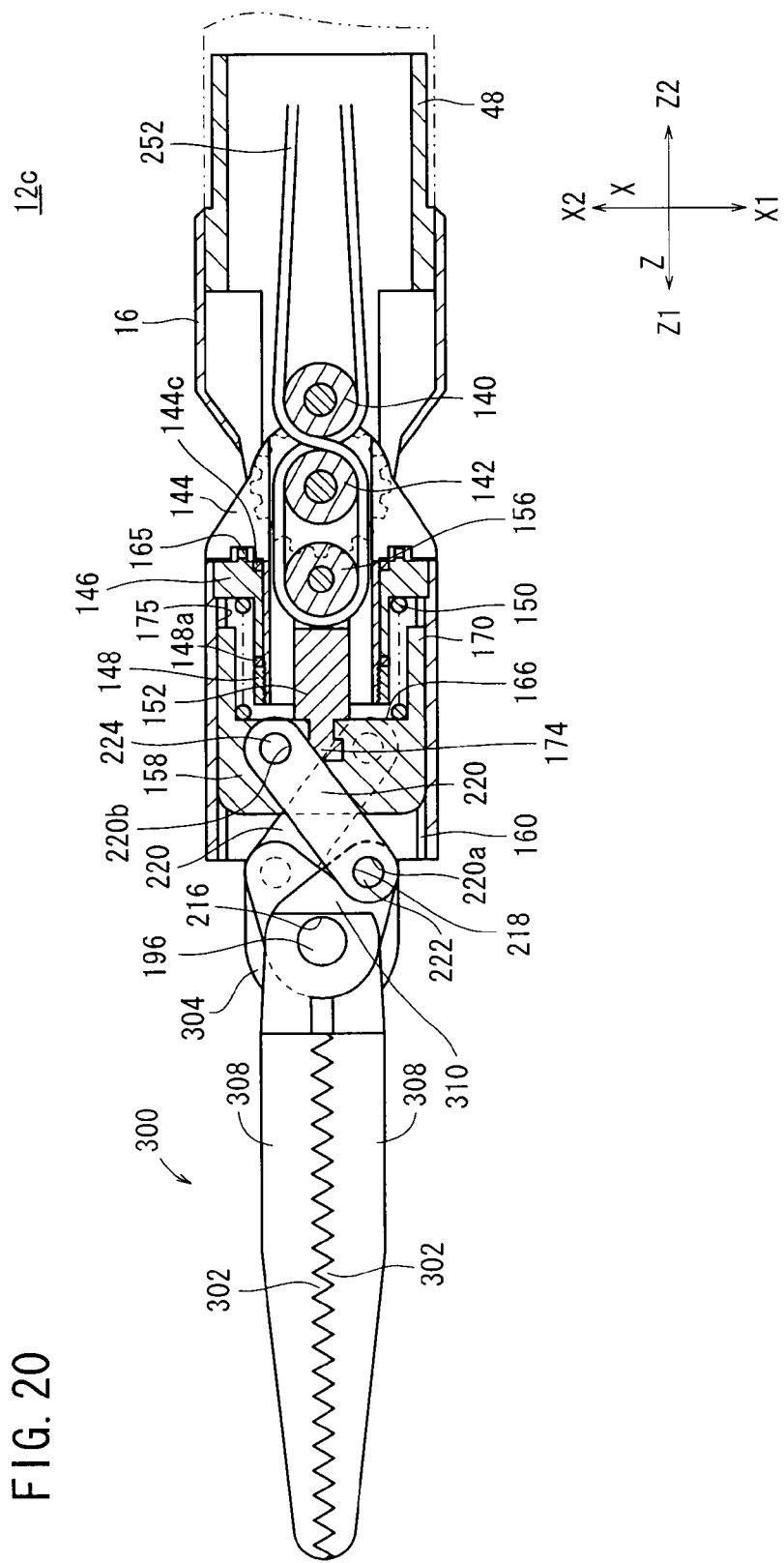
FIG. 20 is a sectional plan view of the distal end working unit according to the third embodiment, with a gripper being closed.

As shown in FIGS. 19 and 20, the end effector members 308 are basically actuated in synchronism in response to operation of the rod 152. Therefore, the end effector members 308 are openable and closable symmetrically with respect to the central axis.

Figure 21:
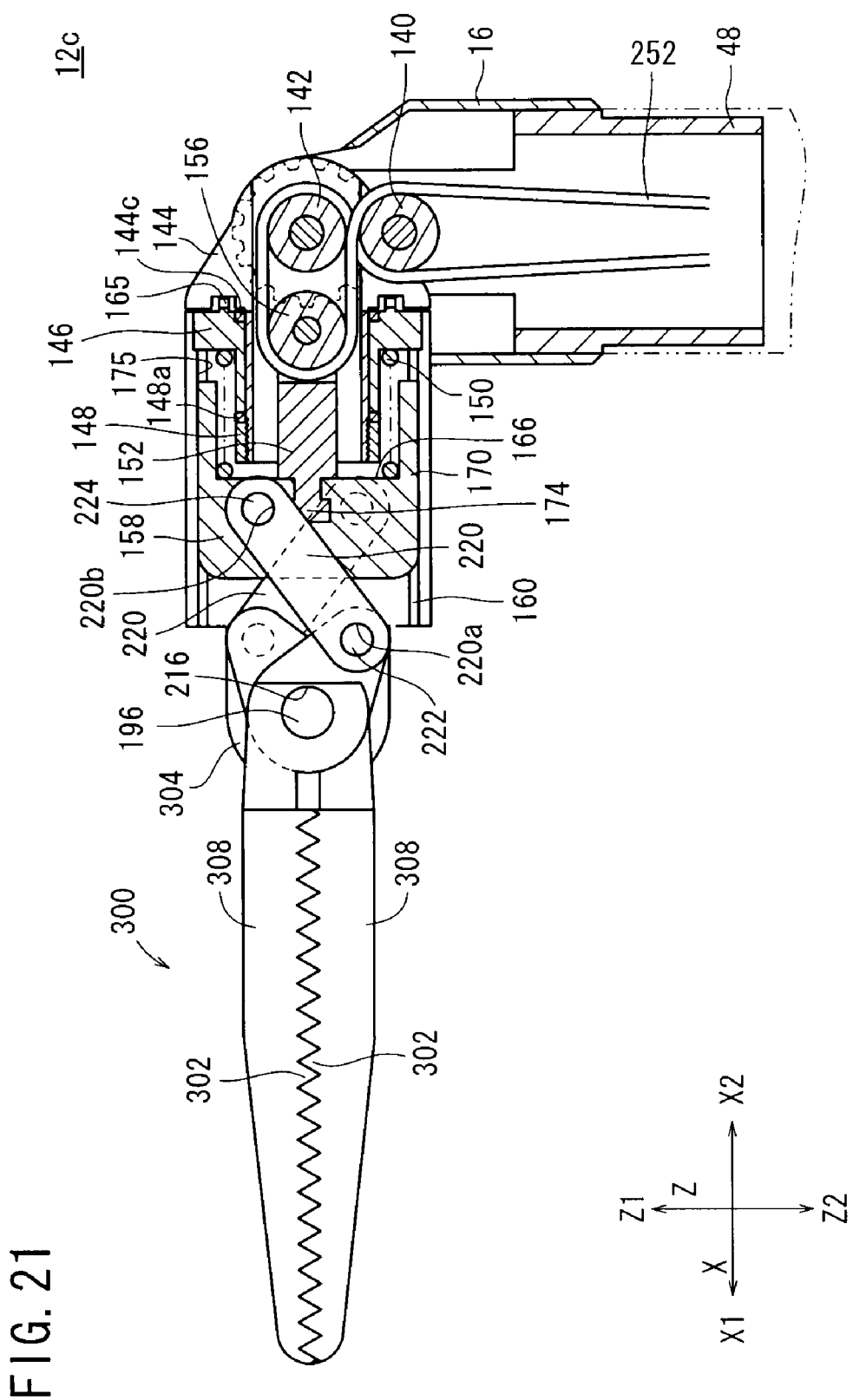
FIG. 21 is a schematic side elevational view of the distal end working unit according to a fourth embodiment, with a roll axis being operated in one direction.

As shown in FIG. 21, when the end effector 300 moves about the yaw axis, since the yaw-axis mechanism and the mechanism for actuating the end effector 300 are held out of interference with each other, the degree of opening of the end effector 300 does not change. Conversely, when the end effector 300 is opened and closed, the end effector 300 does not move about the yaw axis or the roll axis.

Since the end effector 300 is mechanically connected directly to the trigger lever 32, the end effector 300 produces strong gripping forces, wherein the forces applied to the end effector 300 are transmitted to the trigger lever 32.

The distal end working unit 12d according to a fourth embodiment will be described below. With the distal end working units 12a through 12c described above, the trigger lever 32 is pulled actively (i.e., the grippers are closed/opened) by a manual force, and the trigger lever 32 is passively returned by the force of the spring 150, so that the force is applied in one direction only for opening/closing the grippers. With the distal end working unit 12d according to the fourth structural example (as well as with the distal end working unit 12e), a manual force is applied actively to pull and return the trigger lever 32, whereby a force is applied in both directions. The spring 150 for generating forces is dispensed with. The distal end working unit 12d may be used as a gripping forceps as well as a peeling forceps.

Figure 22:
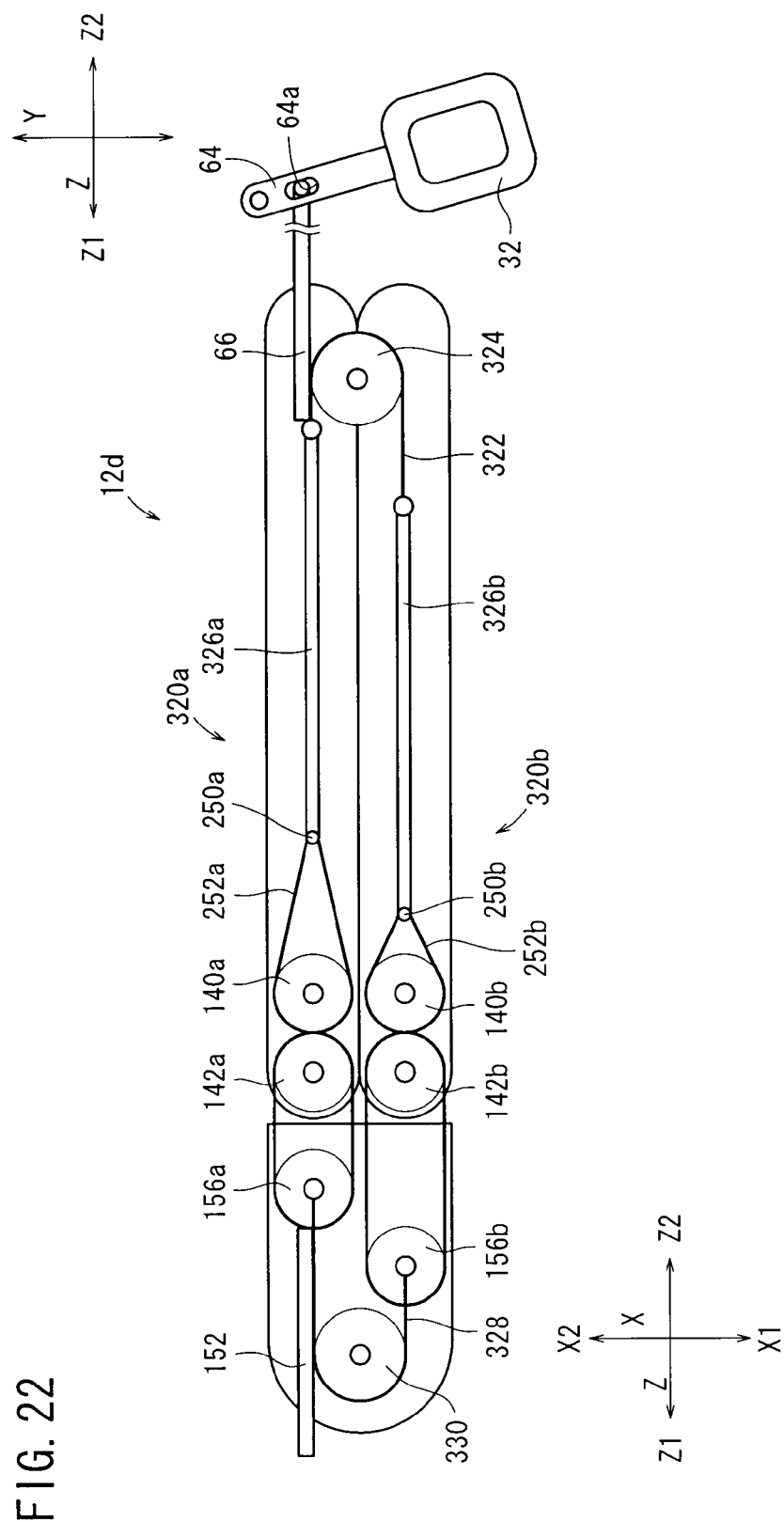
FIG. 22 is a schematic side elevational view of a distal end working unit according to the fourth embodiment, with a trigger lever being pushed out.
Figure 23:
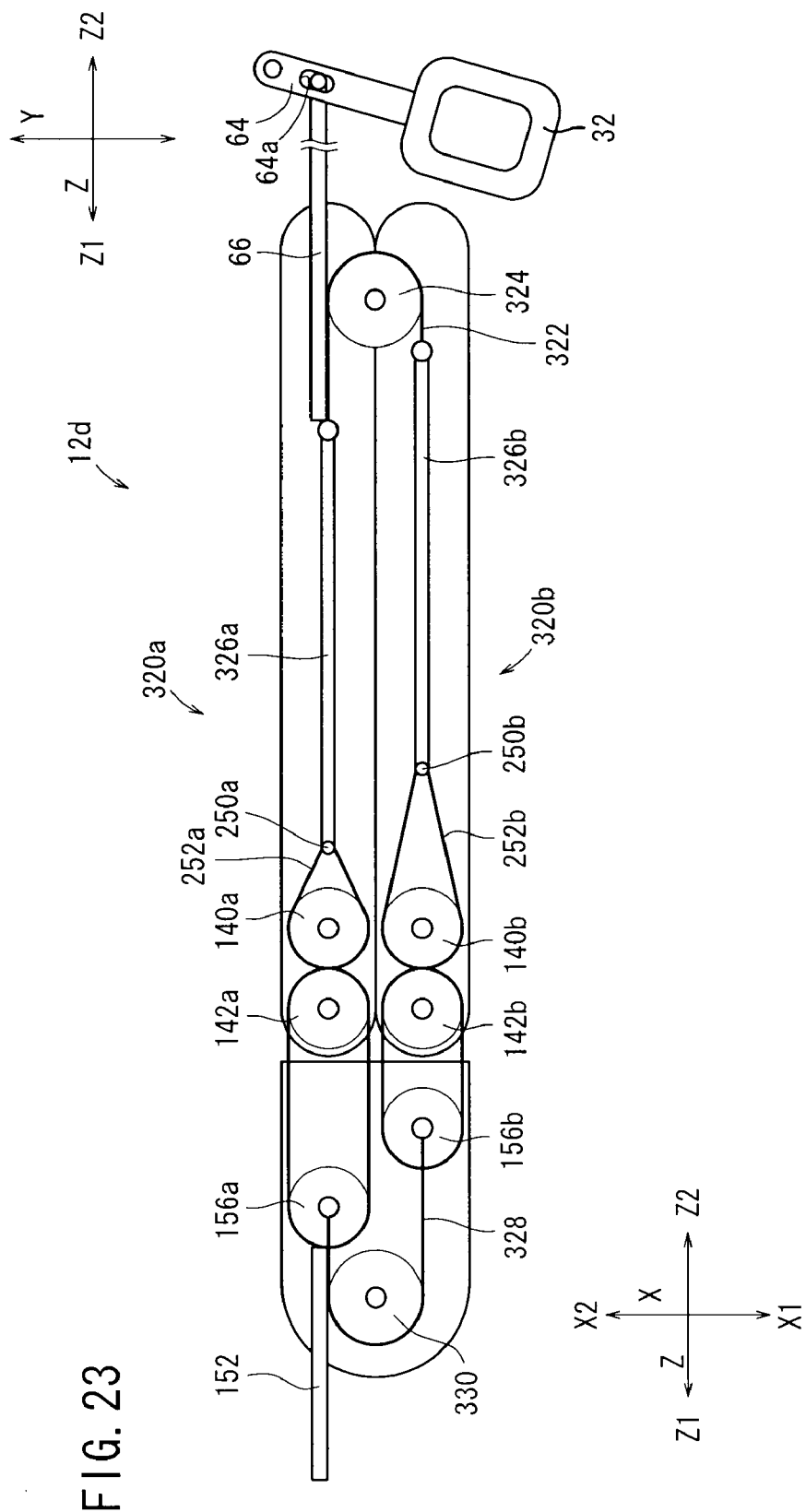
FIG. 23 is a schematic side elevational view of the distal end working unit according to the fourth embodiment, with the trigger lever being fully pulled.
Figure 24:
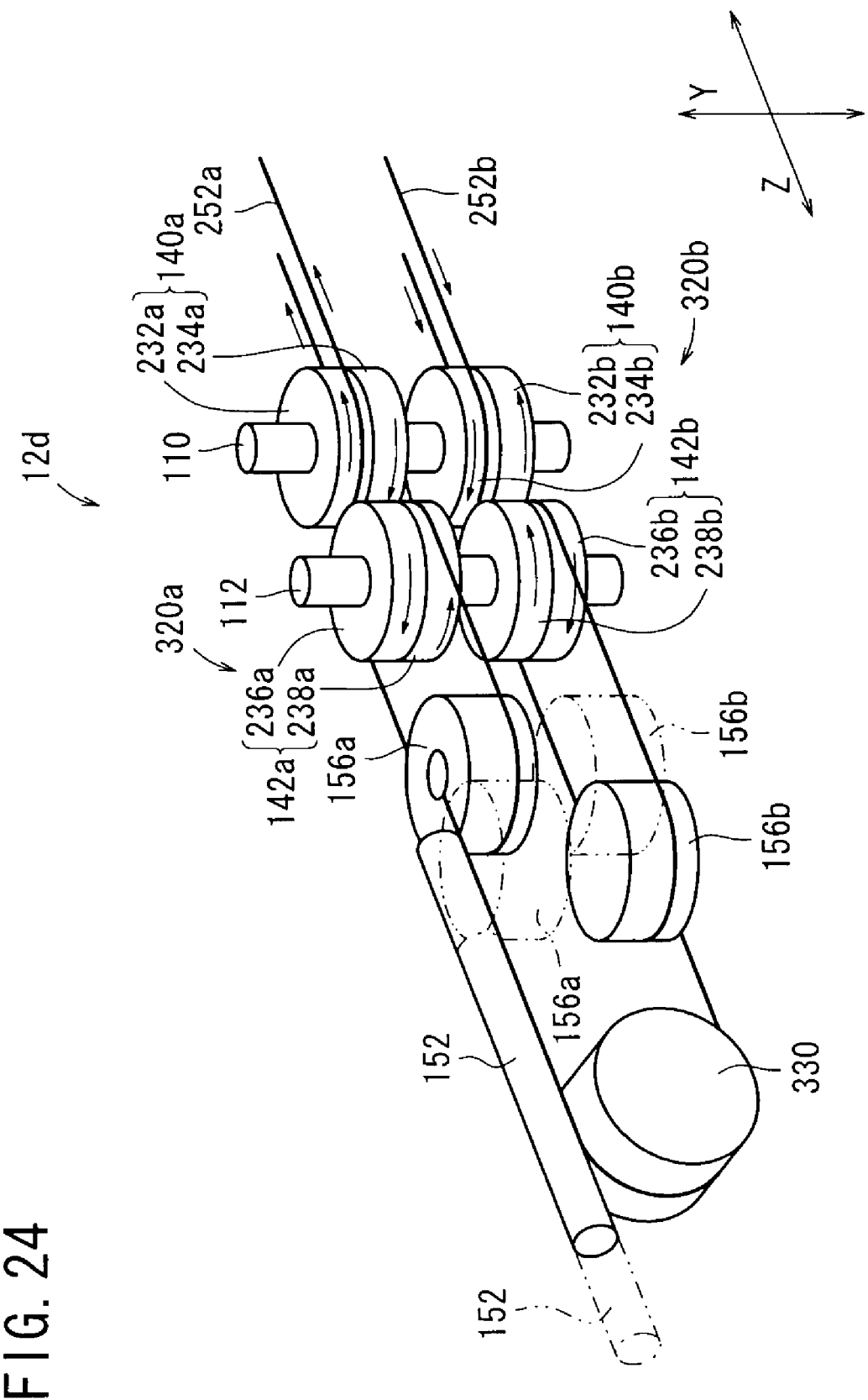
FIG. 24 is a schematic structural view of a distal end working unit according to the fourth embodiment.

As shown in FIG. 22, the distal end working unit 12d includes two mechanisms, i.e., a first end effector driving mechanism 320a and a second end effector driving mechanism 320b, corresponding to the end effector driving mechanism 260 (see FIG. 8). Components of the first end effector driving mechanism 320a are denoted by reference characters with an "a" appended thereto, and components of the second end effector driving mechanism 320b are denoted by reference characters with a "b" appended thereto, so that they can be distinguished from each other. In FIGS. 22 and 23 (as well as FIGS. 38 and 39), the first end effector driving mechanism 320a and the second end effector driving mechanism 320b are shown in parallel with each other on the sheets, for facilitating understanding. If the distal end working unit 12d is incorporated in an actual manipulator 10, then, as shown in FIG. 24 (and FIG. 37), the pulleys are juxtaposed axially (i.e., in the Y direction) such that the rotational shafts of the idle pulleys 140a, 140b are disposed coaxially with each other, and the rotational shafts of the guide pulleys 142a, 142b also are disposed coaxially with each other. In other words, the idle pulleys 140a, 140b are supported commonly on the shaft 110 (see FIG. 24), whereas the guide pulleys 142a, 142b are supported commonly on the shaft 112. The guide pulleys 142a, 142b, which are coaxial with each other, simplify the yaw axis operating mechanism.

The distal end working unit 12d comprises a first end effector driving mechanism 320a, a second end effector driving mechanism 320b, a drive coupling wire (a drive coupling flexible member) 322, and a drive coupling pulley (a rotary operating member) 324, around which the drive coupling wire 322 is wound. With this arrangement, the first end effector driving mechanism 320a and the second end effector driving mechanism 320b can be operated in opposite phase, so as to move a drive link 326a and a drive link 326b easily in opposite directions.

Although not illustrated, the distal end working unit 12d includes a wire-driven mechanism 100, a composite mechanism 102, and an end effector 104, which are identical to those of the distal end working unit 12a.

The drive coupling wire 322 has one end thereof connected to the proximal end of the drive link (drive member) 326a of the first end effector driving mechanism 320a, and the other end thereof connected to the proximal end of the drive link (drive member) 326b of the second end effector driving mechanism 320b. The drive links 326a, 326b correspond to the wire 56, and are connected to terminals 250a, 250b at respective ends of driven wires 252a, 252b. In the distal end working unit 12d, the drive links 326a, 326b may be replaced with wires. In such a case, the drive coupling wire 322 may have both ends thereof directly connected to the terminals 250a, 250b.

The second link 66 (see FIG. 8) has one end connected to the drive link 326a, which can be moved back and forth by the trigger lever 32. Since the drive coupling wire 322 and the drive link 326b are connected to the drive link 326a around the drive coupling pulley 324, the drive link 326a and the drive link 326b are moved back and forth in opposite directions when the second link 66 is moved back and forth.

The trigger lever 32 can actuate the drive link 326a and the drive link 326b through a rack and pinion mechanism, which includes a rack mounted on the second link 66, and a pinion mounted on the drive coupling pulley 324. The drive coupling pulley 324 may be disposed in the distal end working unit 12d (i.e., on a distal end of the connector shaft 48), or may be disposed in the operating unit 14.

The distal end working unit 12d also includes a driven coupling wire (a driven coupling flexible member) 328, having one end connected to a driven pulley 156a of the first end effector driving mechanism 320a and another end connected to a driven pulley 156b of the second end effector driving mechanism 320b, and a driven coupling pulley (a driven coupling cylindrical member) 330 around which the driven coupling wire 328 is wound. In this arrangement, the first end effector driving mechanism 320a and the second end effector driving mechanism 320b can be operated in opposite phase so as to move the rod 152 back and forth.

Either one of the driven pulley 156a and the driven pulley 156b is rotatably held by the rod 152. The rod 152 may be fixed to a linear portion of the driven coupling wire 328. The rod 152 may also be connected to the driven coupling pulley 330 by a rack and pinion mechanism. In other words, the rod 152 may bring about back-and-forth movement of the driven pulleys 156a, 156b or the driven coupling wire 328.

If the drive coupling wire 322 and the driven coupling wire 328 are placed under an initial tension of 0N or higher, and are made free from sagging, various parts of the distal end working unit are prevented from having play, and the distal end working unit can grip the object with high responsiveness.

As shown in FIG. 22, when the trigger lever 32 is fully pulled by the hand, the drive link 326a pulls the driven wire 252a in order to move the driven pulley 156a and the rod 152 in the Z2 direction, thereby closing the end effector 104.

In the second end effective driving mechanism 320b, since the drive link 326b is disposed such that it is pushed outward, the drive link 326b does not obstruct the operation of the rod 152. Since the driven wire 252b produces only tensile forces (i.e., the driven wire 252b does not transmit compressive forces), the driven wire 252b basically does not contribute to the transmission of power.

At this time, when the end effector 104 grips the object W, the driven wire 252, the drive link 326, and the trigger lever 32 are unable to move further in the Z2 direction, thereby allowing the operator to feel, with the fingertip, that the end effector 104 has gripped the object W. The operator also can sense the hardness of the object W. These actions can easily be understood by referring to FIGS. 22 and 10, because the distal end working unit 12a, as shown in FIG. 10, is essentially equivalent to the distal end working unit 12d shown in FIG. 22, although the second end effector driving mechanism 320b is dispensed with.

As shown in FIG. 23, when the trigger lever 32 is fully pushed out by the hand, the drive coupling wire 322 is moved counterclockwise in FIG. 23, and the drive link 326b pulls the driven wire 252b in order to move the driven pulley 156b in the Z2 direction. The driven coupling wire 328 moves in a counterclockwise direction, and the rod 152 and the driven pulley 156a move in the Z1 direction toward the distal end, thereby opening the end effector 104.

Since the forces for pushing out the trigger lever 32 by hand are mechanically and directly transmitted to the end effector 104 by the second end effector driving mechanism 320b, the end effector 104 can be opened with a desired strong force, rather than given forces such as from an elastic body. Therefore, using an outer side surface of the end effector 104, the distal end working unit can appropriately be used to perform techniques for peeling off living tissue or for opening a hole.

When the object W is brought into contact with the outer side surface of the end effector 104, the driven wire 252b, the drive link 326b, and the trigger lever 32 are no longer moved further in the Z1 direction, thereby allowing the operator to feel, with the fingertip, that the outer side surface of the end effector 104 has contacted the object W. The operator also can sense the hardness of the object W.

The distal end working unit 12d can operate about the yaw axis and the roll axis, in the same manner as the distal end working unit 12a. Although not shown, when the distal end working unit 12d operates about the yaw axis, the composite mechanism 102 and the end effector 104, which are closer to the distal end than the shafts (see FIG. 24) of the guide pulleys 142a and 42b, swing in yawing directions about the shafts of the guide pulleys 142a and 42b. Since the distal end working unit 12d makes up a non-interference mechanism, similar to the distal end working unit 12a, when the distal end working unit 12d operates about the yaw axis, the degree at which the end effector 104 is opened remains unchanged. Conversely, when the degree of opening of the end effector 104 is changed, the yaw axis is not operated. The end effector 104 and the roll axis are related to each other in the same manner.

The distal end working unit 12d (as well as the distal end working unit 12e) does not require the spring 150. Depending on design conditions, the spring 150 may be provided to bias the rod 152 to move toward either the distal end or the proximal end. This arrangement makes it possible to hold the end effector open or closed when the trigger lever 32 is not operated. If sufficient space is not available in the distal end working unit 12d, then the spring 150 may also be disposed in the trigger lever 32.

As shown in FIG. 24, in the distal end working unit 12d, the idle pulleys 140a, 140b have respective outer first layer idle pulleys 232a, 232b, which are coaxial with each other, and respective inner second layer idle pulleys 234a, 234b, which also are coaxial with each other. The guide pulleys 142a, 142b have respective outer first layer guide pulleys 236a, 236b, which are coaxial with each other, and respective inner second layer guide pulleys 238a, 238b, which also are coaxial with each other. This structure is similar to the structure shown in FIG. 7, allowing the paired pulleys to rotate in opposite directions for enabling smooth operation.

Figure 25:
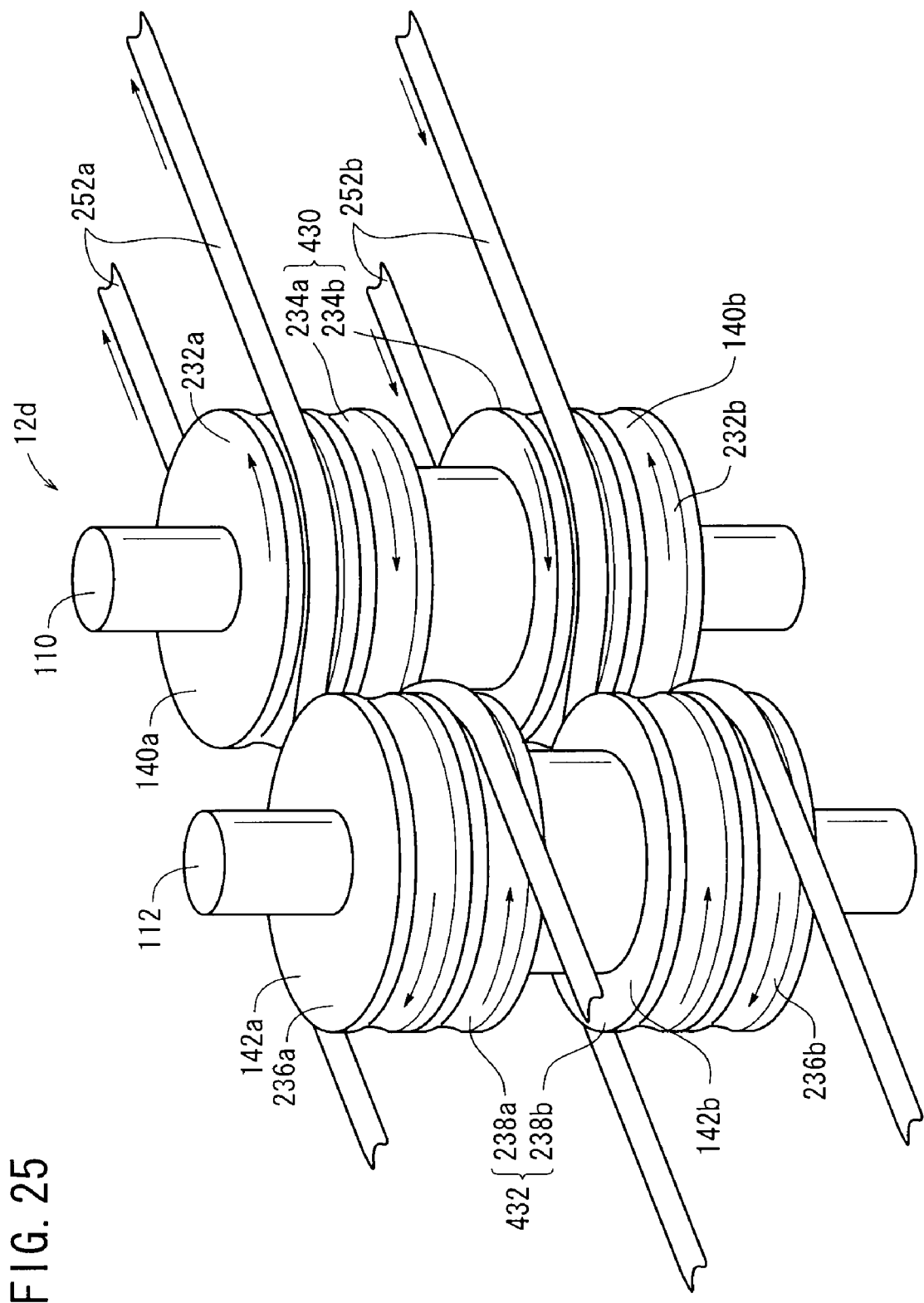
FIG. 25 is an enlarged perspective view of an idle pulley and a guide pulley of the distal end working unit according to the fourth embodiment.

As shown in FIG. 25, the inner two second layer idle pulleys 234a, 234b may be formed integrally with each other, jointly making up a central common idle pulley 430. The inner two second layer guide pulleys 238a, 238b may be formed integrally with each other, jointly making up a central common guide pulley 432.

Specifically, since the drive links 326a and 326b (see FIG. 23) move the same distance in opposite directions, the wires move as indicated by the arrows in FIG. 25, thereby rotating the second layer idle pulley 234a and the second layer idle pulley 234b through the same angle and in the same direction (clockwise in FIG. 25), while also rotating the second layer guide pulley 238a and the second layer guide pulley 238b through the same angle and in the same direction (counterclockwise in FIG. 25). Therefore, such members do not need to be disposed separately, but may make up an integral central common idle pulley 430 and an integral central common guide pulley 432, which are of a simple structure. In FIG. 25, the second layer guide pulley 238a and the second layer guide pulley 238b are shown as being slightly spaced from each other, whereas the second layer idle pulley 234a and the second layer idle pulley 234b also are shown as being slightly spaced from each other, for facilitating understanding. However, the distance between them may essentially be nil.

Drive member advancing and retracting mechanisms 440a through 440d, according to first through fourth examples, for moving the first end effector driving mechanism 320a and the second end effector driving mechanism 320b over substantially the same distance and in opposite directions, shall be described below with reference to FIGS. 26 to 29.

Figure 26:
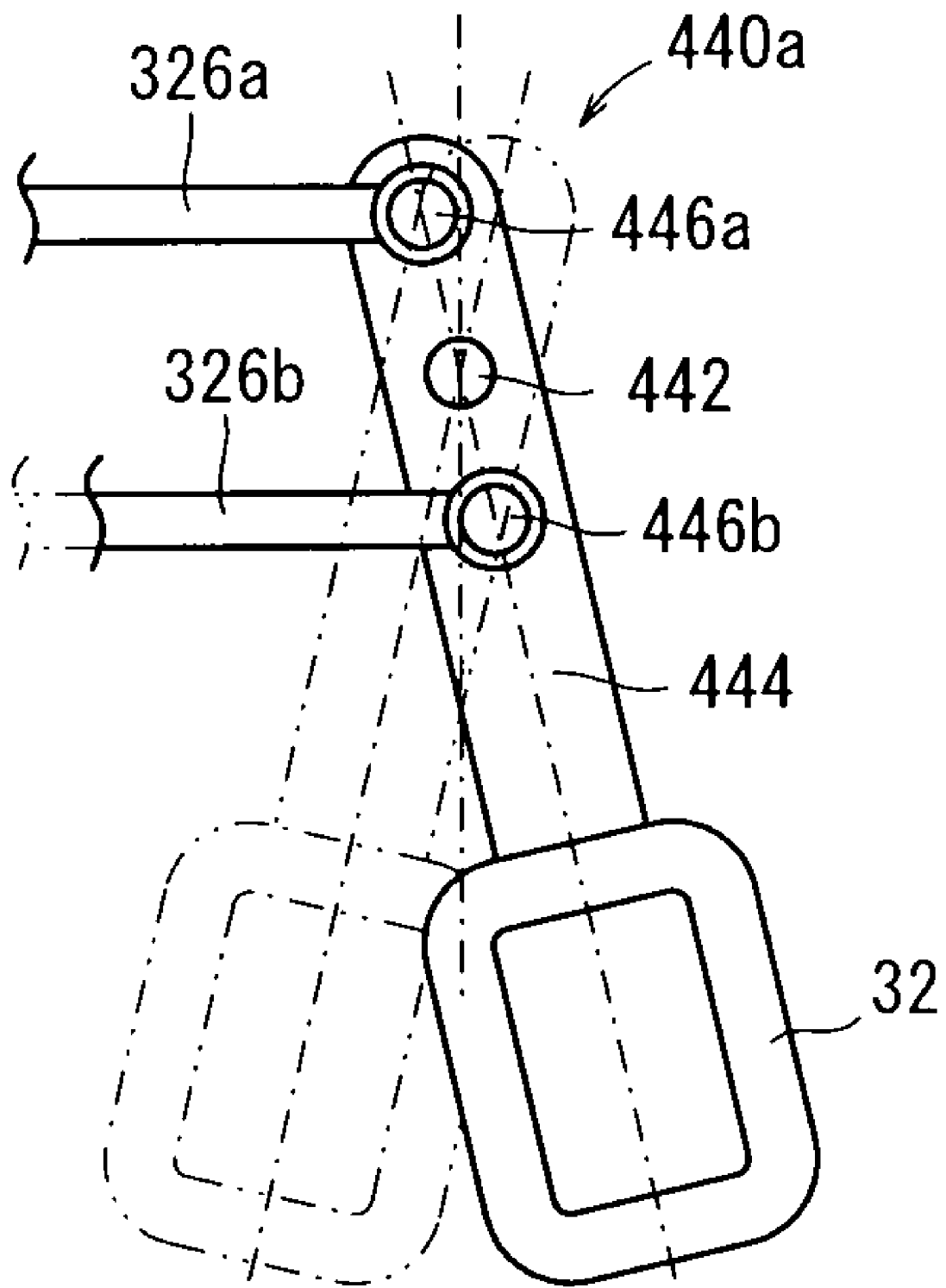
FIG. 26 is a schematic view of a drive member advancing and retracting mechanism according to a first example.

As shown in FIG. 26, the drive member advancing and retracting mechanism 440a according to the first example comprises an arm 444 rotatable about a pivot 442, a rotational engaging member 446a, which is slightly spaced from the pivot 442 in the Y1 direction, and a rotational engaging member 446b, which is slightly spaced from the pivot 442 in the Y2 direction. The distances from the pivot 442 to the two rotational engaging members 446a, 446b are substantially equal to each other. The drive link 326a has a proximal end thereof that rotatably engages with the rotational engaging member 446a. The drive link 326b has a proximal end thereof that rotatably engages with the rotational engaging member 446b.

The arm 444 corresponds to the first link 64 described above. The trigger lever 32 is mounted on the lower end of the arm 444.

Figure 27:
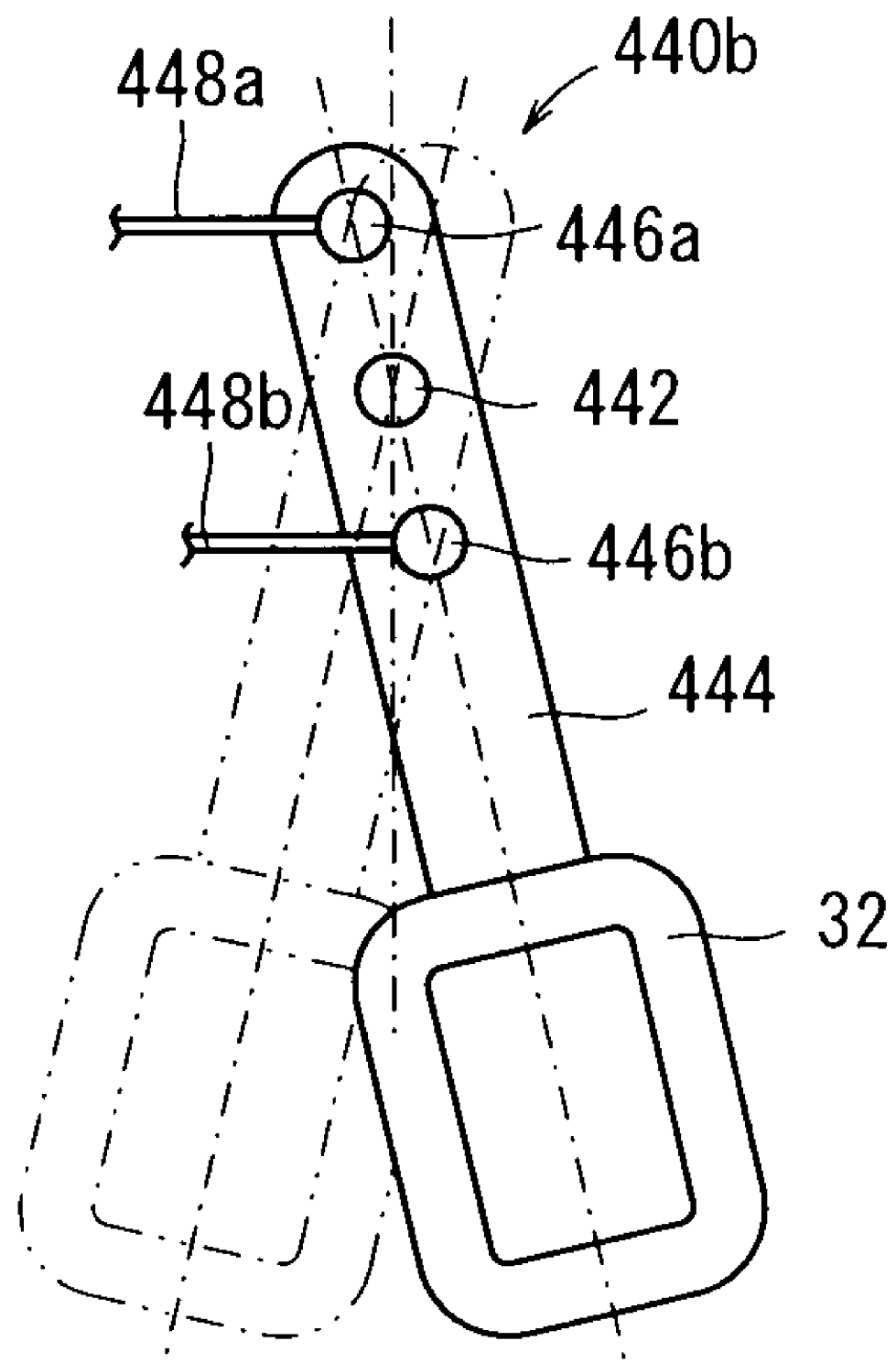
FIG. 27 is a schematic view of a drive member advancing and retracting mechanism according to a second example.

As shown in FIG. 27, as with the drive member advancing and retracting mechanism 440a, the drive member advancing and retracting mechanism 440b according to the second example comprises the arm 444, the pivot 442, and the rotational engaging members 446a, 446b. A wire 448a is connected to the rotational engaging member 446a, and a wire 448b is connected to the rotational engaging member 446b. The other end of the wire 448a is connected to the driven wire 252a (see FIG. 22) by the terminal 250a, whereas the other end of the wire 448b is connected to the driven wire 252b (see FIG. 22) by the terminal 250b.

Figure 28:
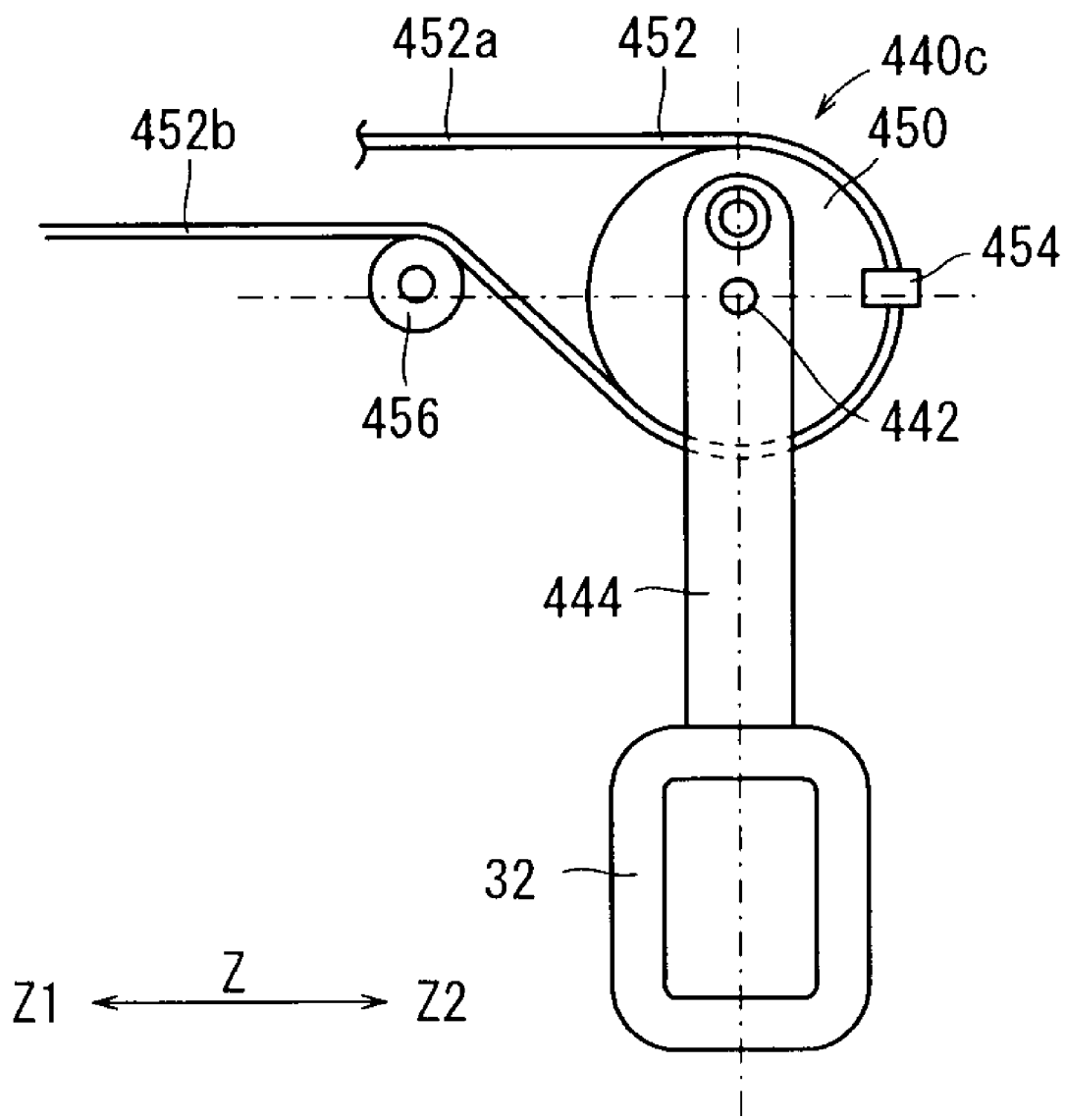
FIG. 28 is a schematic view of a drive member advancing and retracting mechanism according to a third example.

As shown in FIG. 28, the drive member advancing and retracting mechanism 440c according to the third example comprises the arm 444, a rotary operating member 450 fixed to the arm 444, a wire 452 wound around the rotary operating member 450, a securing member 454 securing a portion of the wire 452 to the rotary operating member 450, and an idler 456 that is held against a portion of the wire 452 near to the rotary operating member 450. The rotary operating member 450 is in the form of a thin cylindrical body and operates as a pulley. Specifically, the wire 452 has a portion 452a thereof that is held in contact with an upper portion of the rotary operating member 450, and another portion 452b thereof held in contact with a portion of the rotary operating member 450, which faces in the Y2 direction.

The rotary operating member 450 rotates in unison with the arm 444 about the pivot 442. The portion 452a of the wire 452 from the securing member 454 is connected to the driven wire 252a (see FIG. 22) by the terminal 250a. The other portion 452b of the wire 452 is connected to the driven wire 252b (see FIG. 22) by the terminal 250b.

The rotary operating member 450 has an appropriate large diameter, so as to be capable of fully pulling the driven wire 252a and the driven wire 252b. The securing member 454 is disposed in a position such that it does not prevent the wire 452 from being drawn in and fed out.

The idler 456 is held against the wire 452, thereby defining the layout and path of the wire 452 through the hollow region 48a in the connector shaft 48 to hold the portions 452a, 452b of the wire 452 closely to each other. The idler 456 may double as a tensioner for the wire 452.

Figure 29:
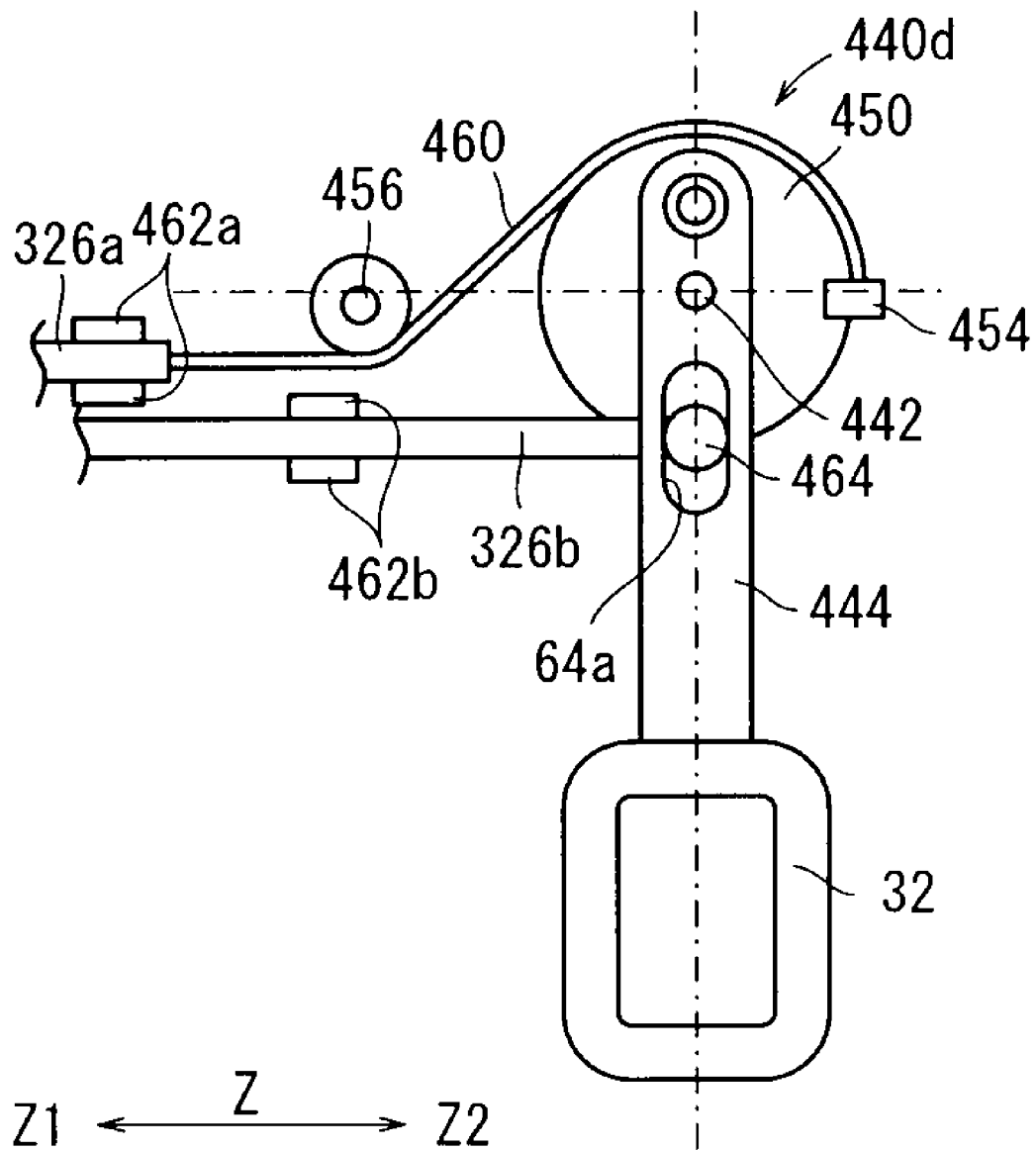
FIG. 29 is a schematic view of a drive member advancing and retracting mechanism according to a fourth example.
Figure 30:
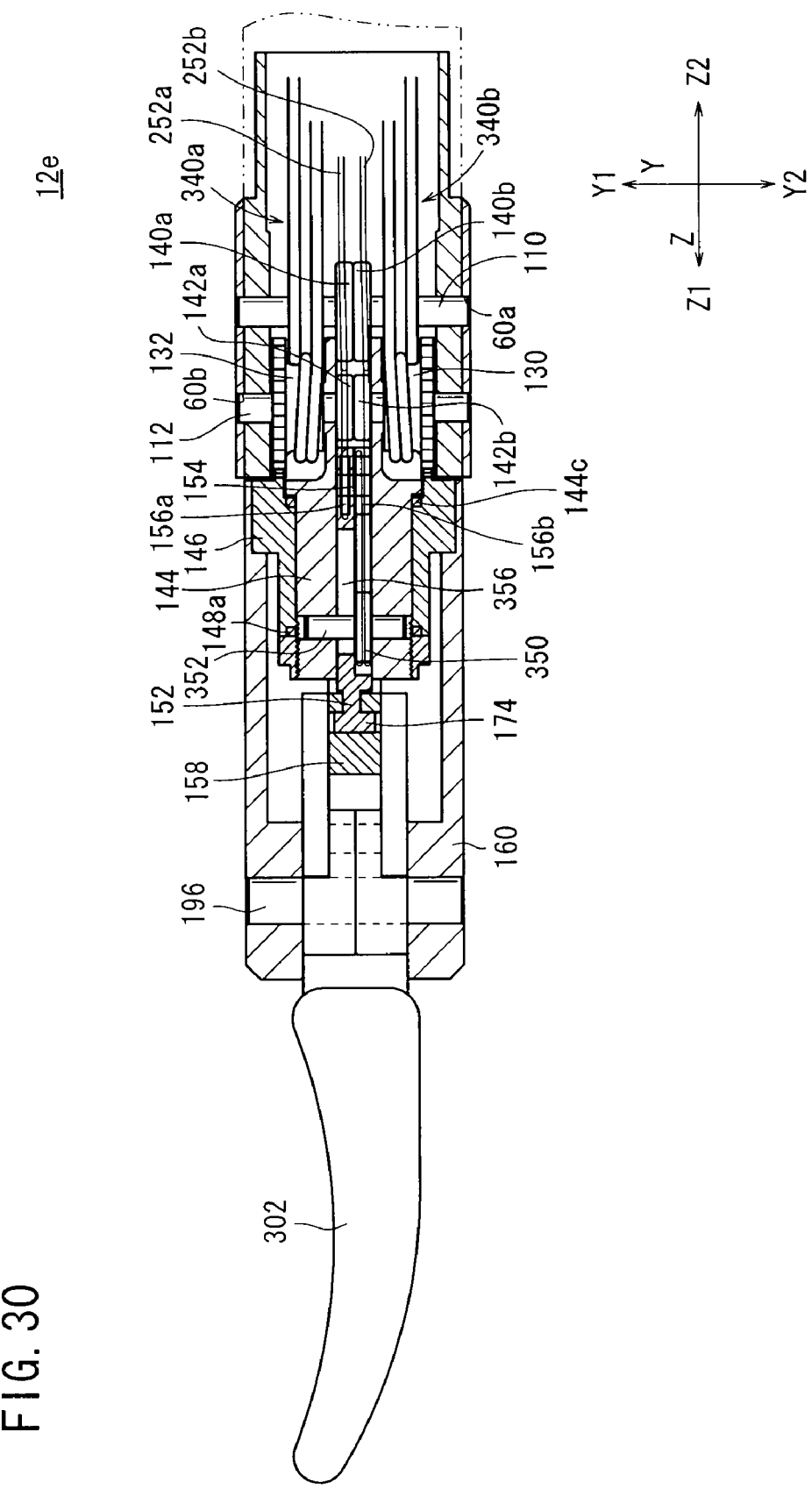
FIG. 30 is a sectional side elevational view of a distal end working unit according to a fifth embodiment.
Figure 31:
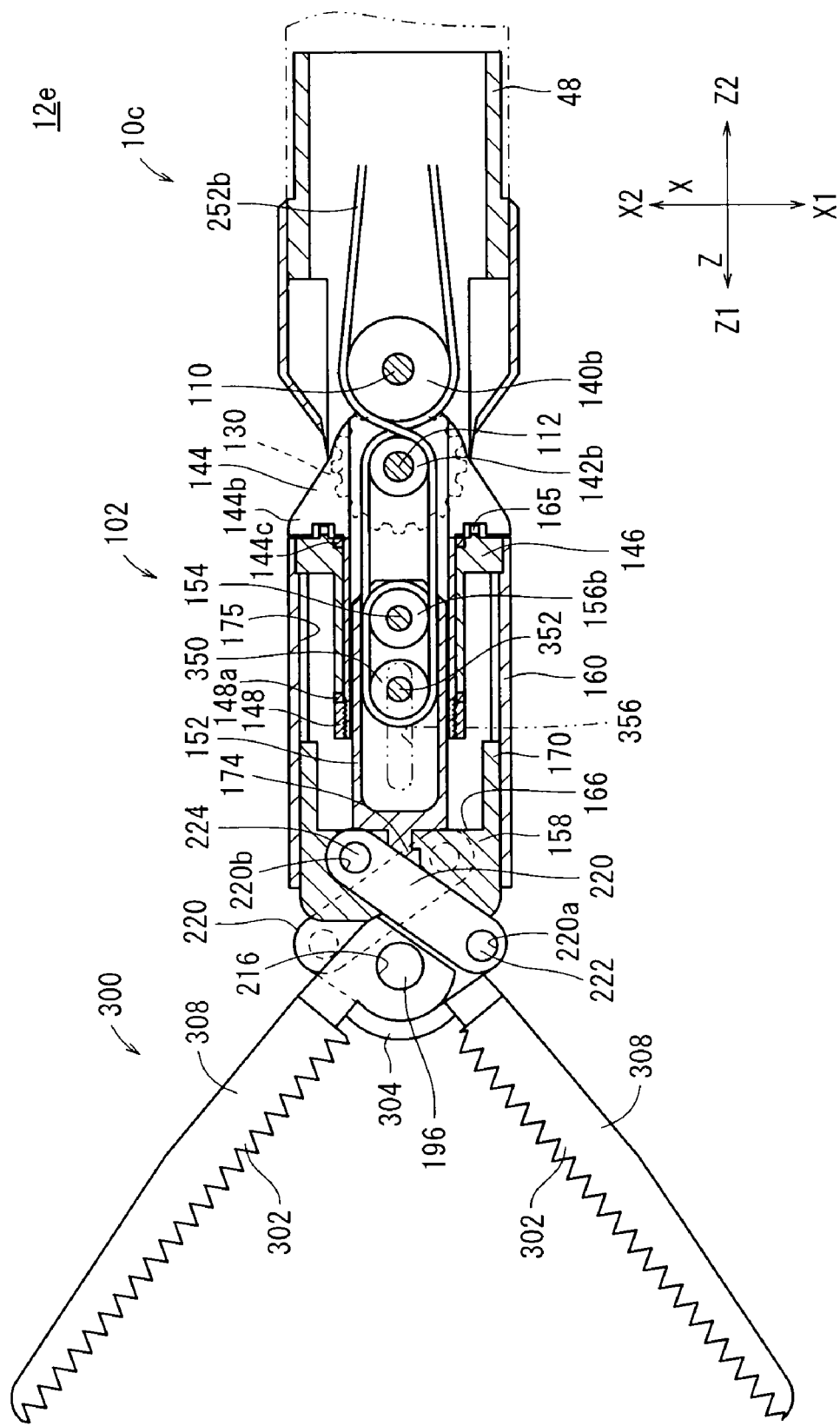
FIG. 31 is a sectional plan view of the distal end working unit according to the fifth embodiment.
Figure 32:
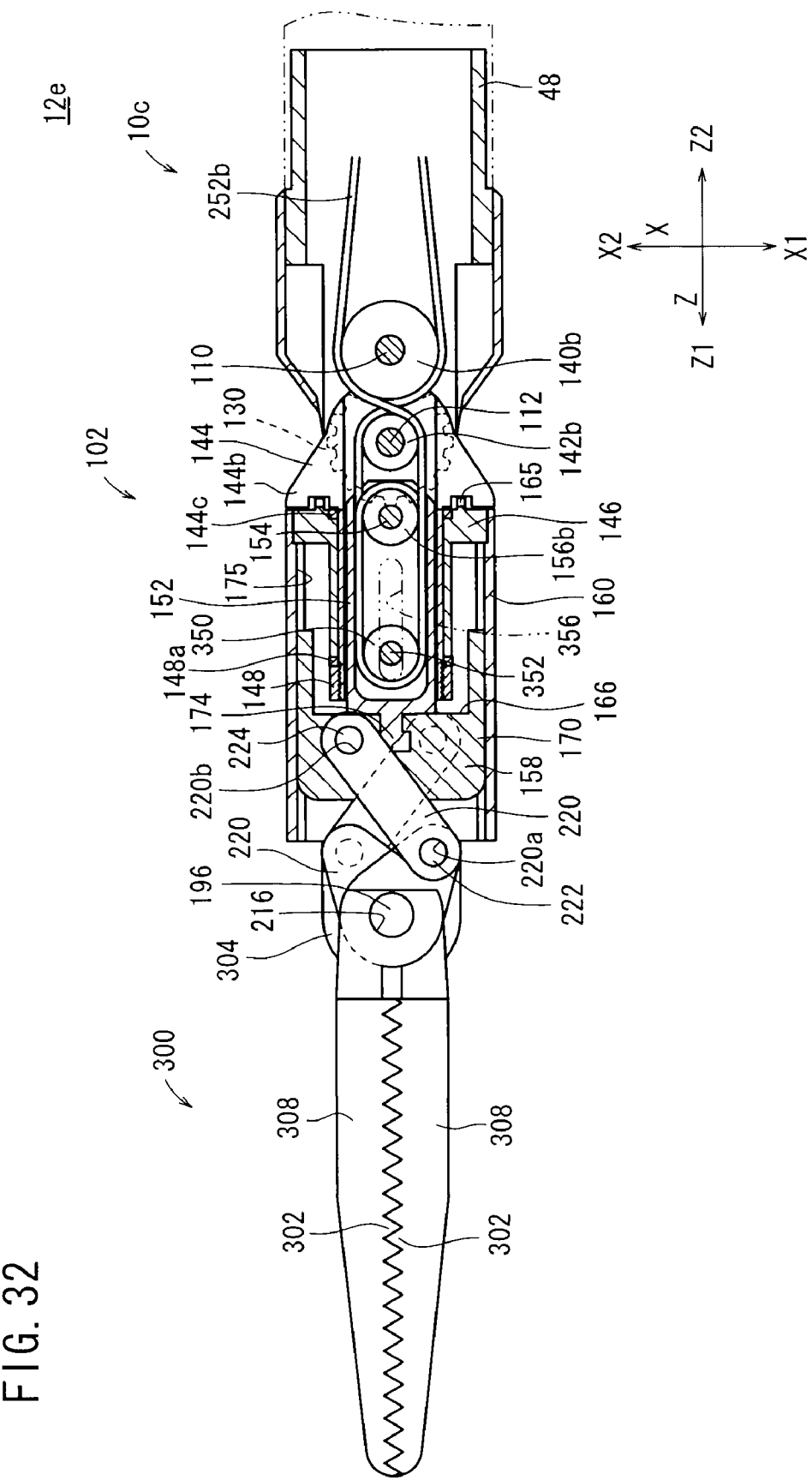
FIG. 32 is a sectional plan view of the distal end working unit according to the fifth embodiment, with a gripper being closed.
Figure 33:
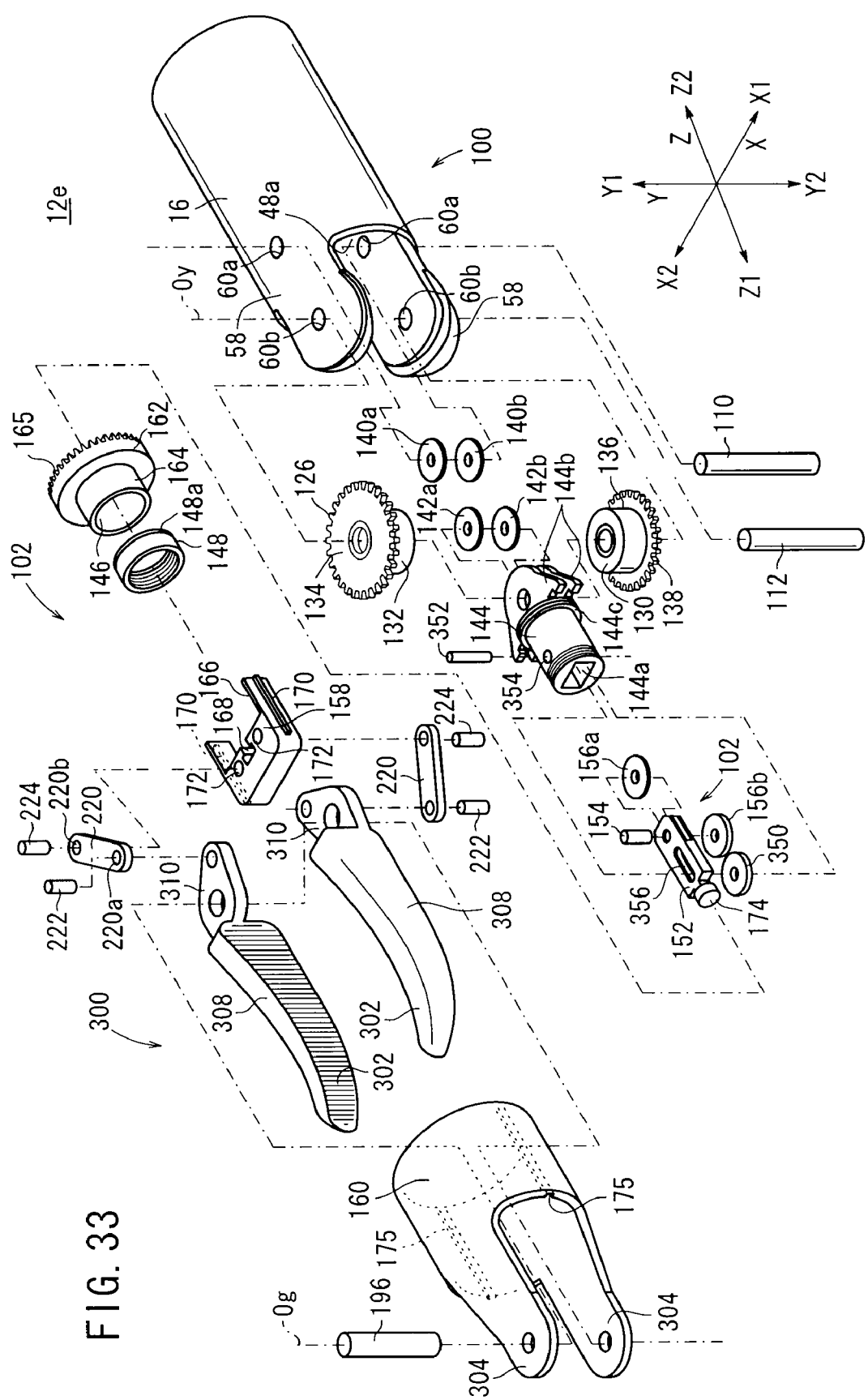
FIG. 33 is an exploded perspective view of the distal end working unit according to the fifth embodiment.

As shown in FIG. 29, the drive member advancing and retracting mechanism 440d according to the fourth example comprises the arm 444, the rotary operating member 450, a wire 460, the securing member 454, and the idler 456. The wire 460 has a distal end thereof connected to the proximal end of the drive link 326a, and a proximal end portion wound around the upper portion of the rotary operating member 450. The proximal end is fixed to the rotary operating member 450 by the securing member 454. The idler 456 is disposed in engagement with the wire 460, for defining the layout and path of the wire 460 and the drive link 326a.

The proximal end of the drive link 326b is rotatably supported on a lower engaging member 464 of the rotary operating member 450. The arm 444 has an oblong hole 64a formed therein for guiding the lower engaging member 464. The drive link 326a and the drive link 326b are supported for back and forth movement in the Z direction by means of guides 462a, 462b.

The drive member advancing and retracting mechanisms 440a through 440d make it possible to move the first end effector driving mechanism 320a and the second end effector driving mechanism 320b over substantially the same distance in opposite directions. The drive member advancing and retracting mechanisms 440a through 440d may also be applied to the distal end working unit 12e, as shall be described below.

The distal end working unit 12e according to the fifth embodiment will be described below. The distal end working unit 12e includes a first end effector driving mechanism 340a and a second end effector driving mechanism 340b.

As shown in FIGS. 30, 31, 32 and 33, the first end effector driving mechanism 340a is essentially the same as the above-described first end effector driving mechanism 320a (see FIG. 22). The second end effector driving mechanism 340b differs from the second end effector driving mechanism 320b (see FIG. 22) described above, in that a return pulley (a return cylindrical member) 350 is added thereto, and the driven coupling wire 328 and the driven coupling pulley 330 are dispensed with. The driven pulley 156a and the driven pulley 156b are disposed coaxially.

The main shaft 144 has a diametrical hole 354 formed therein, with a pin 352 inserted and fixed therein. The hole 354 extends through the sleeve of the main shaft 144 across the hole 144a.

The rod 152 has an oblong hole 356 formed therein, which extends axially and has a width large enough to allow the pin 352 to be inserted therethrough. The rod 152 is disposed at a position that is slightly offset from the axis of the working unit 16 in the Y1 direction. The knob 174 on the distal end is disposed on the axis (see FIG. 8). However, the rod 152 may also be positioned centrally.

As with the driven pulley 156 (see FIG. 6), the driven pulley 156a is rotatably supported by the pin 154 on the end of the rod 152, in the Z2 direction. The pin 154 extends through the rod 152 and projects in the Y2 direction, with the driven pulley 156b being supported on the projecting end thereof. The driven pulley 156b has a width large enough to support two turns of the driven wire 252b. The hole 144a has a height large enough so that the driven pulleys 156a, 156b and the rod 152 may be inserted therein. The driven pulleys 156a, 156b are coaxially supported by the pin 154 in the hole 144a for independent rotation.

Within the hole 144a, the pin 352 is inserted into the oblong hole 356 and the central hole in the return pulley 350 from the Y1 direction and toward the Y2 direction, thus allowing the rod 152 and the driven pulleys 156a, 156b to move axially back and forth. The return pulley 350 is supported rotatably by the pin 352, is fixed in position, and has a width large enough to support two turns of the driven wire 252b. If the return pulley 350 is of a two-layer structure, then the return pulley 350 can be rotated in opposite directions when the end effector is opened and closed, thereby reducing friction between the wire and the pulley.

Figure 34:
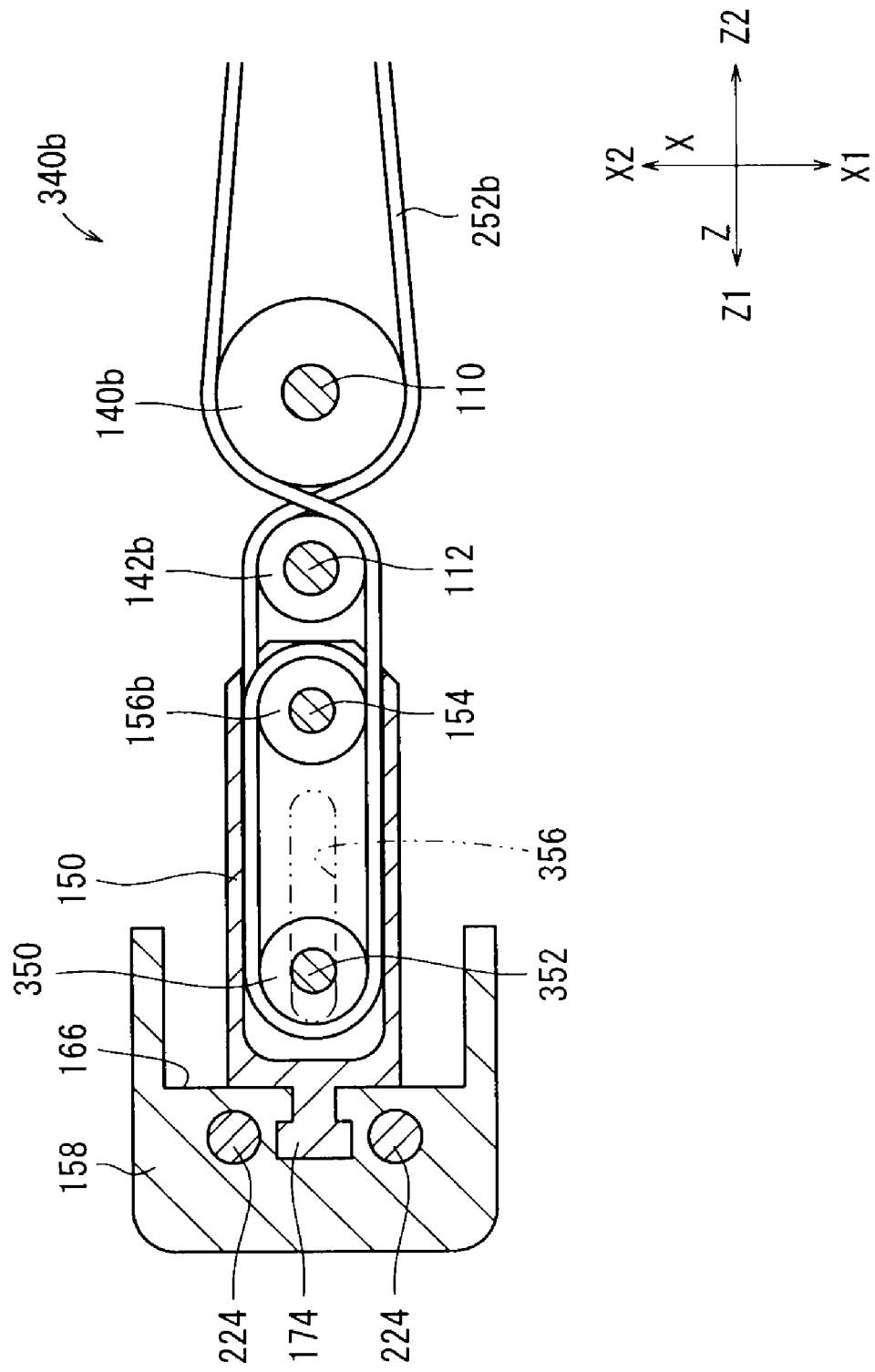
FIG. 34 is a plan view, partly in cross section, of a second end effector drive mechanism with a trigger lever being pushed out.
Figure 35:
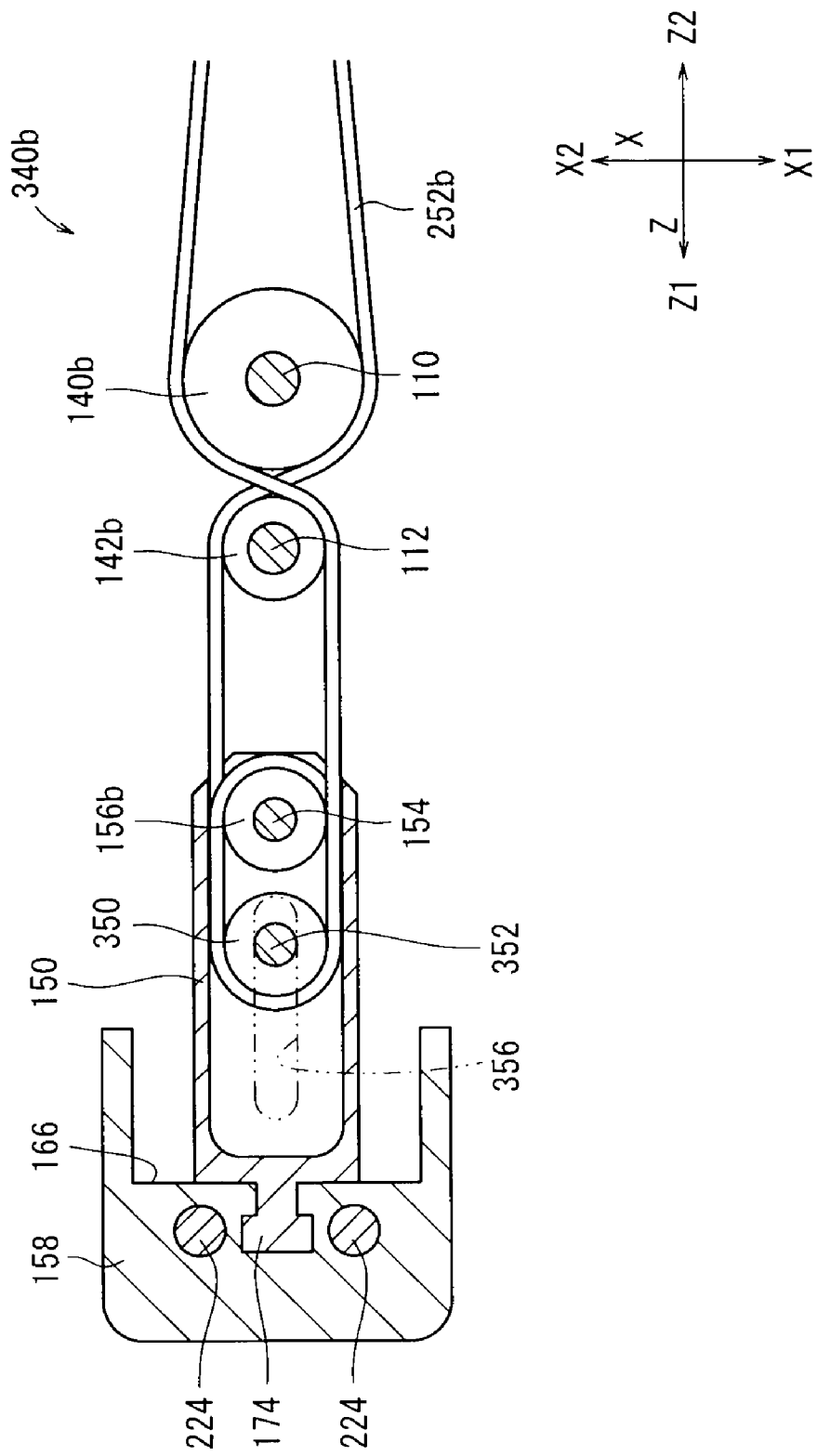
FIG. 35 is a plan view, partly in cross section, of the second end effector drive mechanism with the trigger lever being fully pulled.
Figure 36:
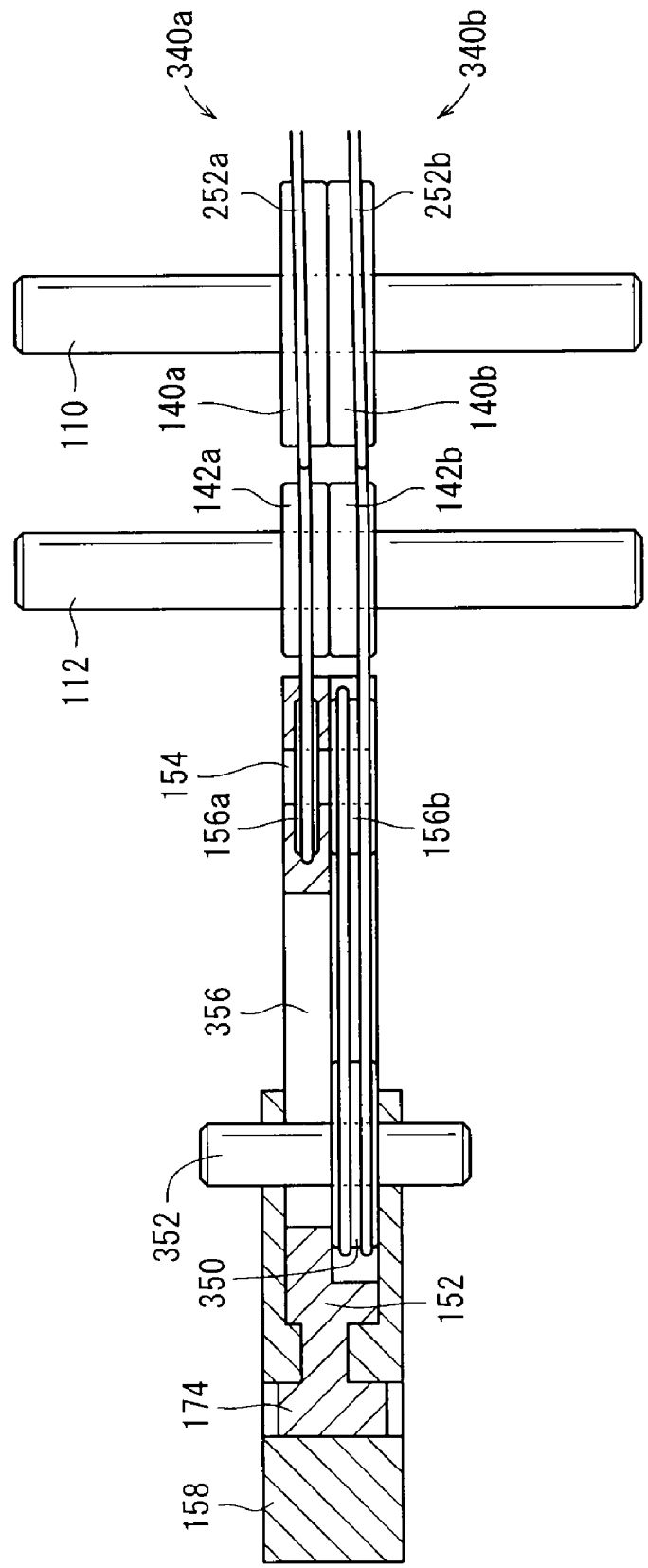
FIG. 36 is a side elevational view, partly in cross section, of the second end effector drive mechanism with the trigger lever being pushed out.

As shown in FIGS. 34, 35, and 36, in the second end effector driving mechanism 340b, the return pulley 350 is disposed more closely to the distal end than the driven pulley 156b, and the driven wire 252b is wound around the driven pulley 156b and the return pulley 350. In other words, the driven wire 252b passes from the terminal 250b of the drive link 326b of the drive member, through the side of the idle pulley 140b that faces in the X1 direction, and then extends in the X2 direction, passing through the side of the guide pulley 142b that faces in the X2 direction, and extends to the surface of the driven pulley 156b, which faces in the X2 direction. The driven wire 252b extends in the Z1 direction to the surface of the return pulley 350 that faces the X2 direction, is wound in a half turn around the surface of the return pulley 350 that faces the X1 direction, and then returns in the Z2 direction.

The driven wire 252b is wound in a half turn around the surface of the driven pulley 156b, which faces the Z2 direction. The driven wire 252b passes through the side thereof, which faces in the X2 direction, and extends again toward the return pulley 350. The driven wire 252b is wound in a half turn around the surface of the return pulley 350, which faces the Z1 direction, and returns toward the X2 direction. Thereafter, the driven wire 252b extends from the side of the guide pulley 142b, which faces in the X1 direction, to the side of the idle pulley 140b, which faces in the X2 direction, and is connected to the terminal 250b of the drive link 326b. The terminal 250 and the driven wire 252b are mechanically connected to the trigger lever 32 by the drive link 326b.

The idle pulley 140b is greater in diameter than the guide pulley 142b in FIGS. 34, 35, and 36, for preventing the gears 134, 138 (see FIG. 6) disposed adjacent to the guide pulley 142b from interfering with the shaft 110, and for holding the idle pulley 140b and the guide pulley 142b close to each other.

Figure 37:
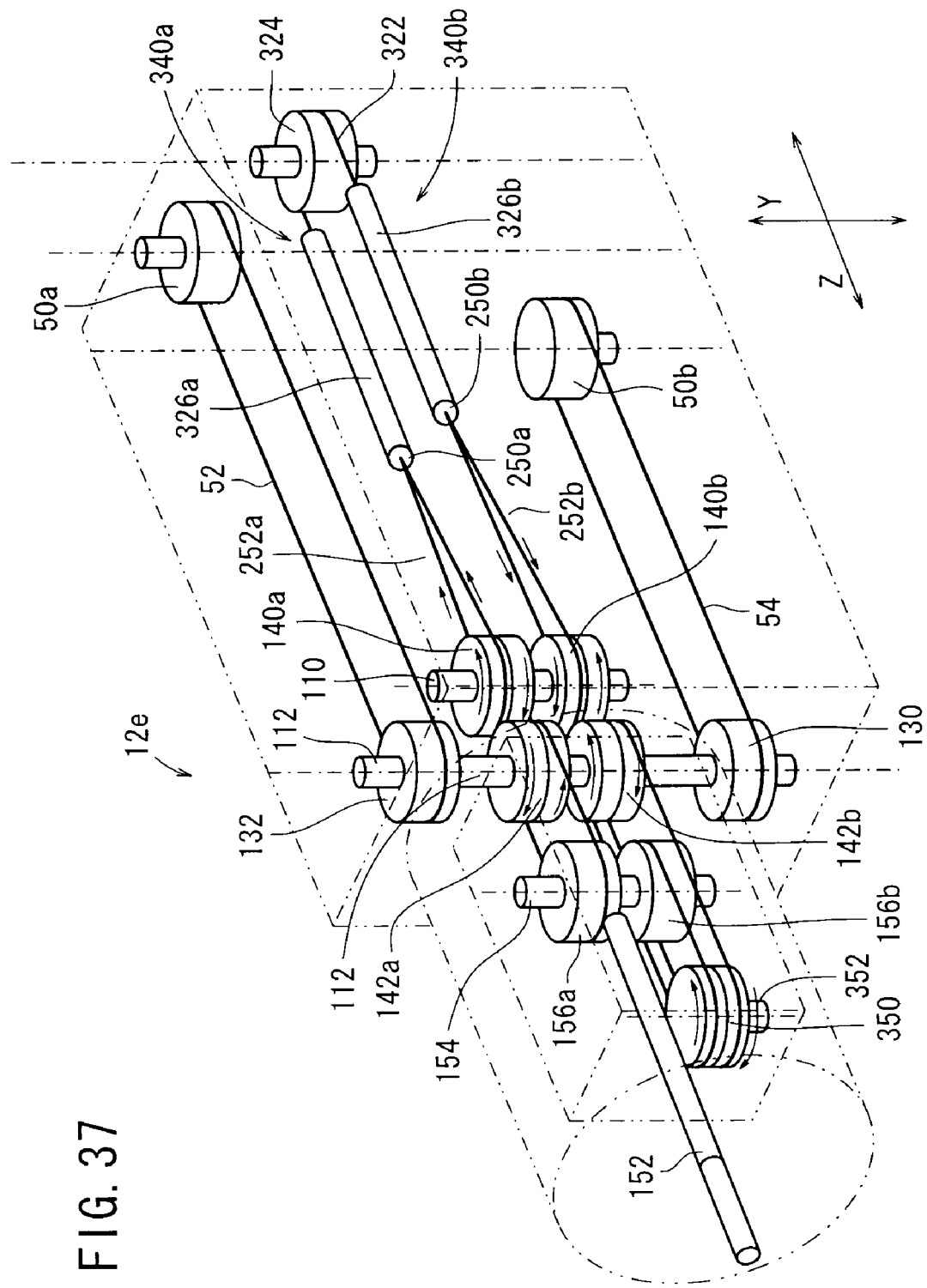
FIG. 37 is a schematic structural view of the distal end working unit according to the fifth embodiment.

FIG. 37 schematically shows the distal end working unit 12e, for facilitating understanding of the structure thereof.

Figure 38:
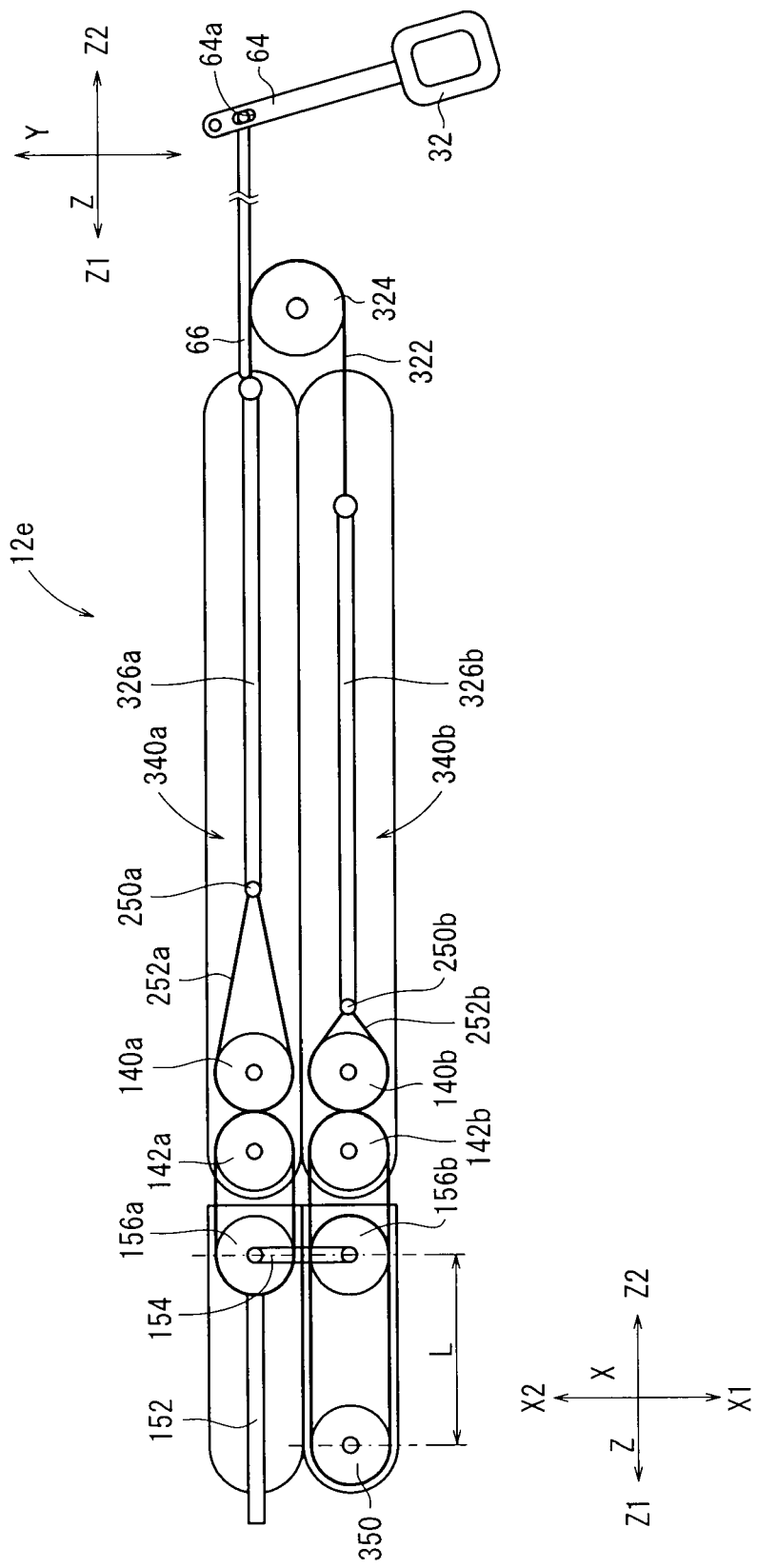
FIG. 38 is a schematic side elevational view of the distal end working unit according to the fifth embodiment, with the trigger lever being fully pulled.

As shown in FIG. 38, when the trigger lever 32 is fully pulled by the hand, the rod 152 moves in the Z2 direction to close the end effector 300. At this time, the operations and advantages of the distal end working unit 12e are the same as those of the distal end working units shown in FIGS. 9 and 22, and such features will not be described in detail below.

Since the driven pulley 156b is arranged coaxially with the driven pulley 156a, the driven pulley 156b is displaced in unison with the driven pulley 156a in the Z2 direction. Since the drive link 326b is displaced and pushed out, the driven wire 252b and the drive coupling wire 322 do not sag. The distance between the driven pulley 156b and the return pulley 350 is represented by L.

Figure 39:
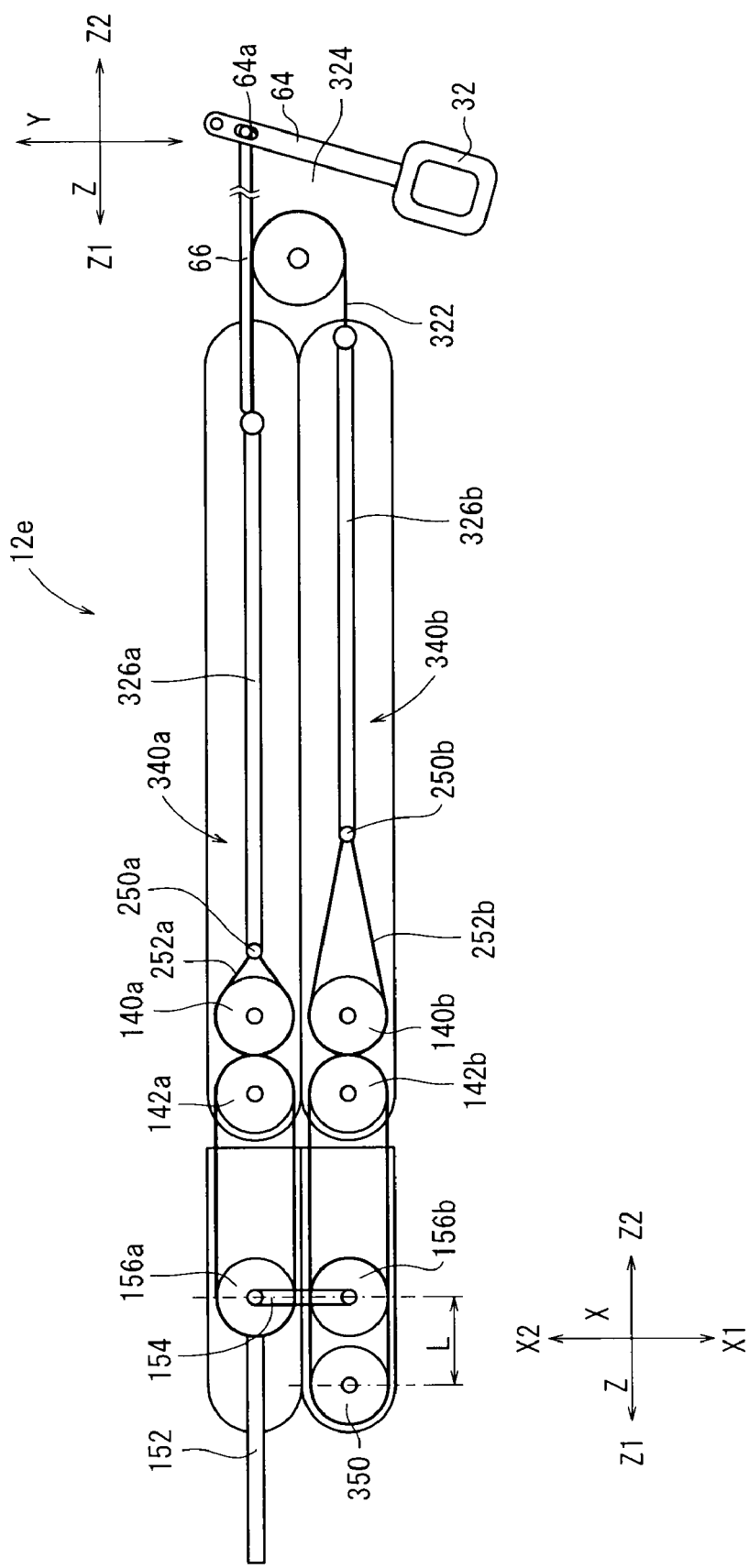
FIG. 39 is a schematic side elevational view of the distal end working unit according to the fifth embodiment, with the trigger lever being pushed out.

As shown in FIG. 39, when the trigger lever 32 is fully pushed out by hand, the drive coupling wire 322 moves counterclockwise in FIG. 39, and the drive link 326b acts to pull the driven wire 252b. Since the distal end portion of the driven wire 252a is wound around the return pulley 350, which is fixed in position, the driven wire 252a does not move in its entirety, and the driven pulley 156b moves in the Z1 direction depending on the distance that the drive link 326b moves, thereby reducing the distance L. Since the distance L is reduced, the driven wire 252a is fed out accordingly toward the drive link 326b, which is allowed to move. The driven pulley 156b thus acts as a movable pulley, whereas the return pulley 350 acts as a fixed pulley.

Since the driven pulley 156a is coaxial with the driven pulley 156b, the driven pulley 156a is displaced in unison with the driven pulley 156b in the Z1 direction, thereby pushing the rod 152 in the Z1 direction to open the end effector 300.

Since the forces for pushing out the trigger lever 32 by hand are transmitted directly and mechanically to the end effector 300 by the second end effector driving mechanism 320b, the end effector 300 can be opened with a desired strong force, rather than by given forces such as from an elastic body. Therefore, the distal end working unit can appropriately be used to perform techniques for peeling off living tissue or for opening a hole using an outer side surface of the end effector 300.

When the object W is brought into contact with the outer side surface of the end effector 300, the driven wire 252b, the drive link 326b, and the trigger lever 32 are no longer moved further in the Z1 direction, thus allowing the operator to feel, with the fingertip, that the outer side surface of the end effector 300 has contacted the object W. The operator also can feel the hardness of the object W.

The distal end working units 12d, 12e can operate about the yaw axis and the roll axis in the same manner as the distal end working unit 12a. Although not shown, when the distal end working unit 12e operates about the yaw axis, the composite mechanism 102 and the end effector 300, which are positioned more closely to the distal end than the shafts (see FIG. 37) of the guide pulley 142a and the guide pulley 42b, swing in the yawing direction about the shafts of the guide pulley 142a and the guide pulley 42b. Since the distal end working unit 12e is a non-interference mechanism, as with the distal end working unit 12a, when the distal end working unit 12e operates about the yaw axis, the degree at which the end effector 300 is opened remains unchanged. Conversely, when the degree of opening of the end effector 300 is changed, the yaw axis is not operated. The end effector 300 and the roll axis are related to each other in the same manner.

Since the driven pulleys 156a, 156b slide over the same distance and in the same direction, they can be disposed coaxially with each other, such that the distal end working unit 12e enables increased housing and space efficiency. Further, the distal end working unit 12e is made up of a reduced number of parts, and can easily be assembled and serviced for maintenance. Since the driven pulleys 156a, 156b slide in unison with each other, only one sliding movement assembly is sufficient. With the distal end working unit 12d, however, since the driven pulleys 156a, 156b slide in opposite directions, two sliding movement assemblies are required.

All the pulleys of the distal end working unit 12e, i.e., the idle pulleys 140a, 140b, the guide pulleys 142a, 142b, the driven pulleys 156a, 156b, and the return pulley 350, have their rotational shafts positioned parallel to each other (in the Y directions), and the pulleys are laid out efficiently without dead spaces. The driven coupling pulley 330 of the distal end working unit 12d, however, has an axis that extends perpendicularly to the other pulleys.

The distal end working unit 12e does not require the driven coupling wire 328 or the wire fastening means thereof, which are provided in the distal end working unit 12d. The distal end working unit 12e is simpler in structure, since it does not require the driven coupling pulley 330 in the distal end working unit 12d.

The wire drive ratio of the distal end working unit 12e at the time the end effector 300 is operated to grip and open is 1:1, as with the distal end working unit 12d, and is well balanced.

Figure 40:
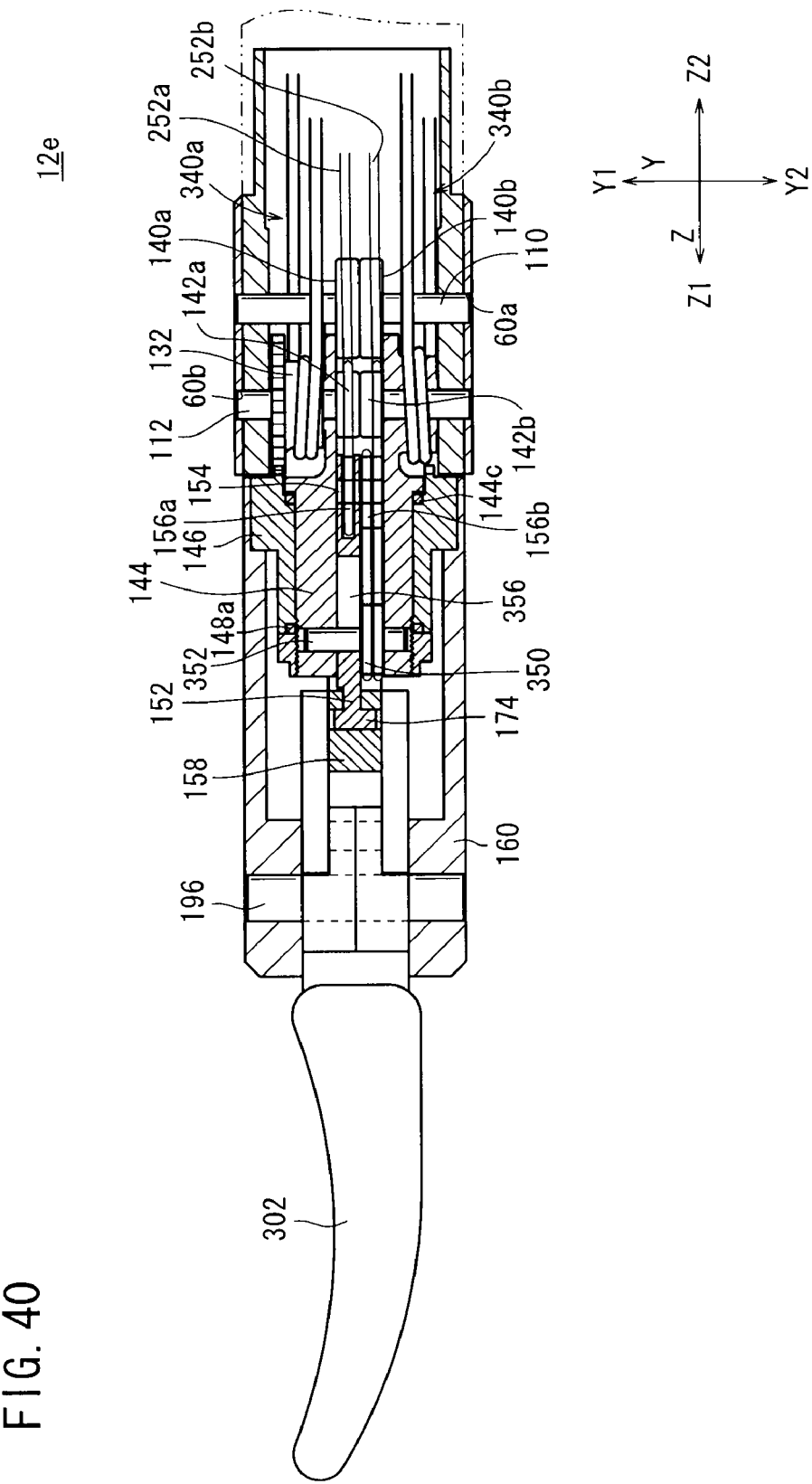
FIG. 40 is a sectional side elevational view of a distal end working unit according to a first modification of the fifth embodiment.

In the distal end working unit 12e, the face gear 165 together with the gears 134, 138 make up a differential gear. According to a first modification, as shown in FIG. 40, the face gear 165 is held in mesh with the gear 134 only, and portions thereof corresponding to the main shaft 144 and the gear body 130 (see FIG. 6) may be of an integral structure. The distal end working unit thus operates about the roll axis based on the action of the wire 52 via the gear 134, and operates about the yaw axis by swinging the main shaft 144, based on a coordinated operation of the wires 52, 54.

Figure 41:
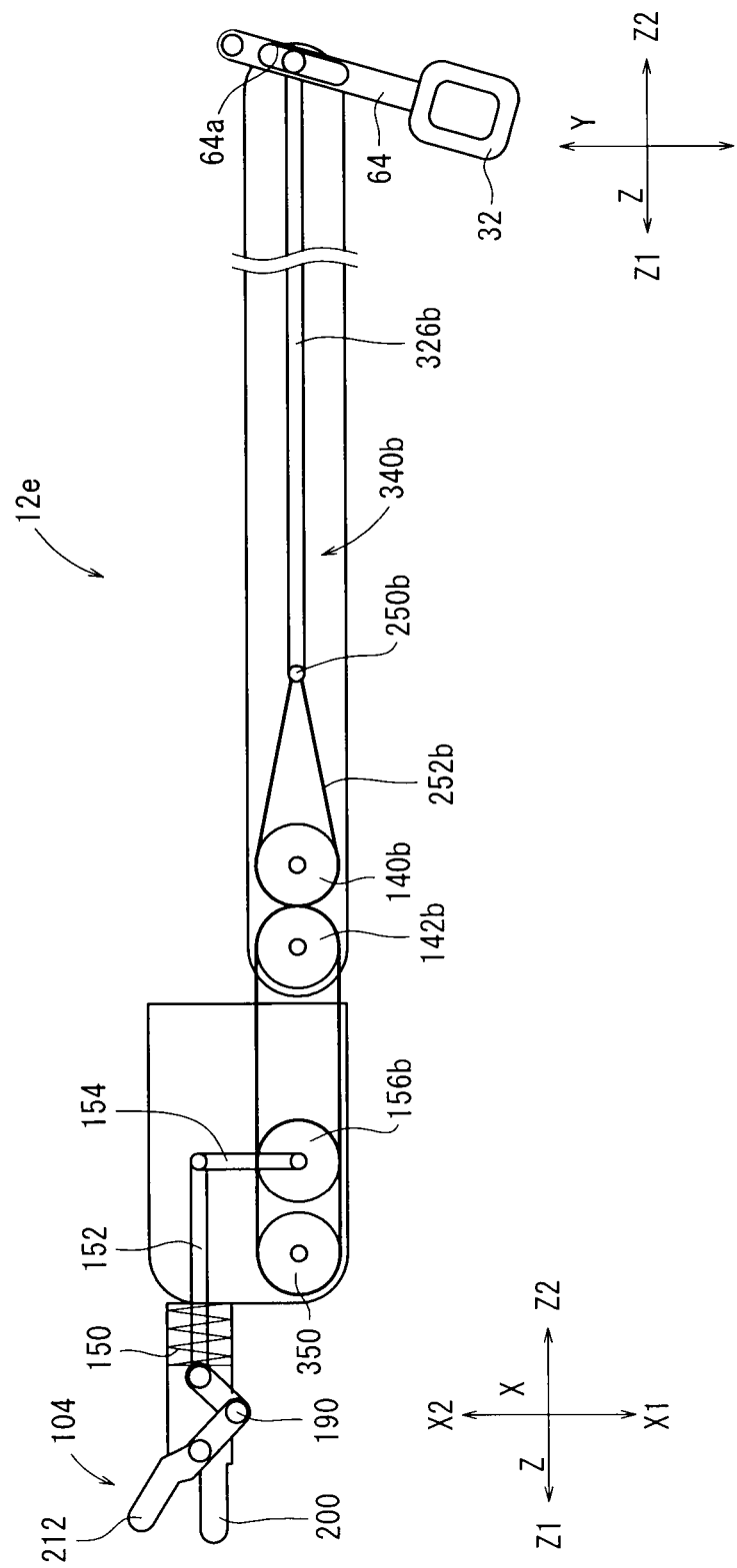
FIG. 41 is a sectional side elevational view of a distal end working unit according to a second modification of the fifth embodiment.

As shown in FIG. 41, according to a second modification of the distal end working unit 12e, the second end effector driving mechanism 340b having the return pulley 350 is employed, and the first end effector driving mechanism 340a is dispensed with. According to this modification, the spring 150 may be provided to make up for the action of the first end effector driving mechanism 340a, which is dispensed with. While the spring 150 is a compression spring in the distal end working unit 12a (see FIG. 8) according to the first embodiment, according to the second modification, the spring 150 comprises a tension spring for resiliently biasing the end effector to close itself. The trigger lever 32 is connected to the drive link 326a. According to the modification shown in FIG. 41, the idle pulley 140b may be dispensed with. As with the distal end working unit 12b (see FIG. 18), according to the second embodiment, the driven wire 252 may be wound in one turn or more around the guide pulley 142b from at least one direction. If two distal end working units 12e according to the second embodiment shown in FIG. 41 are combined in parallel with each other, then manual forces work actively when the trigger lever 32 is pulled and returned, and forces are produced in both directions. Hence, the spring 150 for producing forces may be dispensed with. The distal end working unit may be used as a gripping forceps as well as a peeling forceps.

Although the distal end working unit 12e comprises a double-sided-open-type of end effector 300, the distal end working unit 12e may also incorporate a single-sided-open-type of end effector 104 (see FIG. 5), or another type of end effector.

The distal end working units 12a through 12e are not limited to the above structures, but may consist of various other structures as well.

Figure 42A:
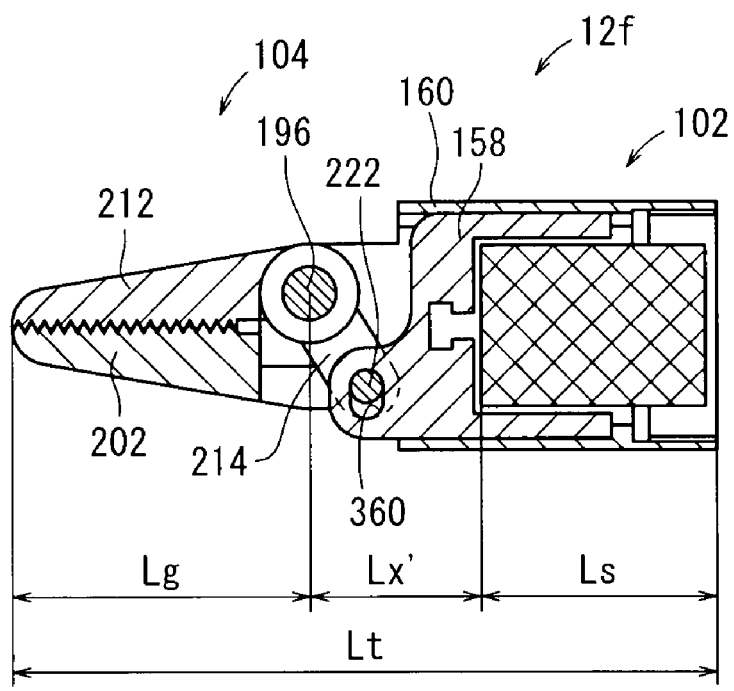
FIG. 42A is a schematic sectional side elevational view of a distal end working unit, with a gripper link portion thereof being omitted from illustration.
Figure 42B:
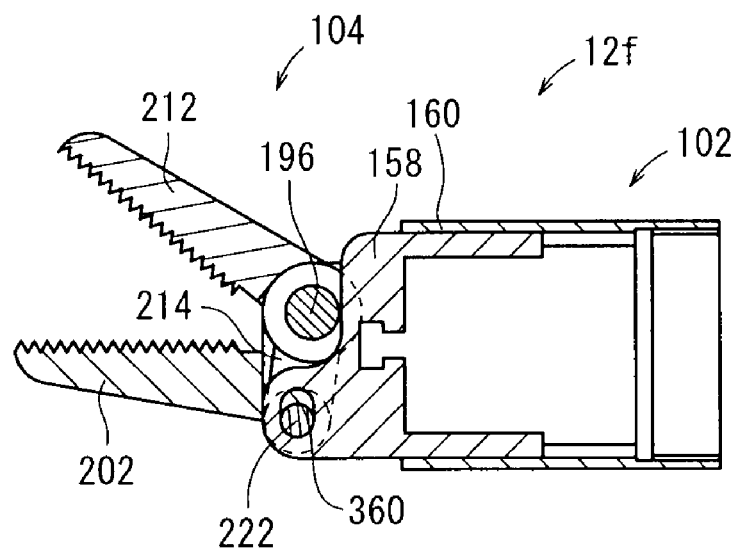
FIG. 42B is a schematic sectional side elevational view of the distal end working unit, with the gripper link portion thereof being omitted from illustration, and with a gripper being opened.

For example, as shown in FIG. 42A, a distal end working unit 12f according to a modification does not include the gripper links 220 (see FIG. 5), but rather, the driven plate 158 and the lever 214 are connected to each other by the pin 222 and an oblong hole 360. The pin 222 is fixed to the lever 214. According to this modification, with the distal end working unit 12f, when the pin 222 slides inside the oblong hole 360, the second gripper 212 is turned so as to open and close the end effector (see FIG. 42B). The distal end working unit 12f can be made up of a reduced number of parts, since the gripper link 220 and the pin 224 (see FIG. 5) are dispensed with.

The distal end working unit 12f includes a wire-and-pulley non-interference mechanism (i.e., composite mechanism 102), which is basically of the same structure as the distal end working unit 12f, and has the same length Ls. The length Lg from the pin 196 forming the gripper axis to the distal end can be of the same dimension as the distal end working unit 12a shown in FIG. 5. The connector length Lx' from the front surface of the driven plate 158 to the pin 196 can be considerably smaller than the connector length Lx (see FIG. 5) of the distal end working unit 12a, thus resulting in a reduction in the overall length Lt of the distal end working unit 12f. Accordingly, the distal end working unit 12f can easily be operated by bending the yaw-axis joint in the body cavity 22, even if the body cavity 22 is small, and makes it possible to perform operations in deeper and smaller spaces. The distal end working unit 12f may be applied to a structure in which two grippers, such as gripping forceps, are opened and closed. Furthermore, linear motion of the rod 152 may be converted into rotary motion by gears for gripping objects. The end effector is not limited to being a gripper type, but may comprise rotary electrodes or the like having scissors, or an opening and closing unit.

The wire-and-pulley non-interference mechanism according to the present embodiment has a wider operable range (e.g., of ±90°) and a more compact structure than the conventional type (e.g., a soft mirror type) including a curved portion corresponding to the connector shaft 48 and other non-interference mechanisms. Therefore, the distance from the curved or bent portion, corresponding to a joint, to the distal end may be reduced, thereby allowing the end effector to approach the living body freely and without limitations, and to operate in small spaces.

As described above, the end effector driving mechanisms 260, 320a, 320b, 340a and 340b of the manipulator 10 according to the present embodiment have structures that are kept out of interference with the other operating axes, thereby making it possible to easily construct the distal end working unit with high degrees of freedom, and to realize strong gripping forces (or peeling forces). The drive members (the wire 56, etc.), which are mechanically connected to the manually operated input unit, allow the operator to feel the external forces that are applied to the distal end working unit 12 reliably and easily. Moreover, the end effector driving mechanisms 260, 320a, 320b, 340a, 340b are made up of a simple structure that is free of gears.

Figure 43:
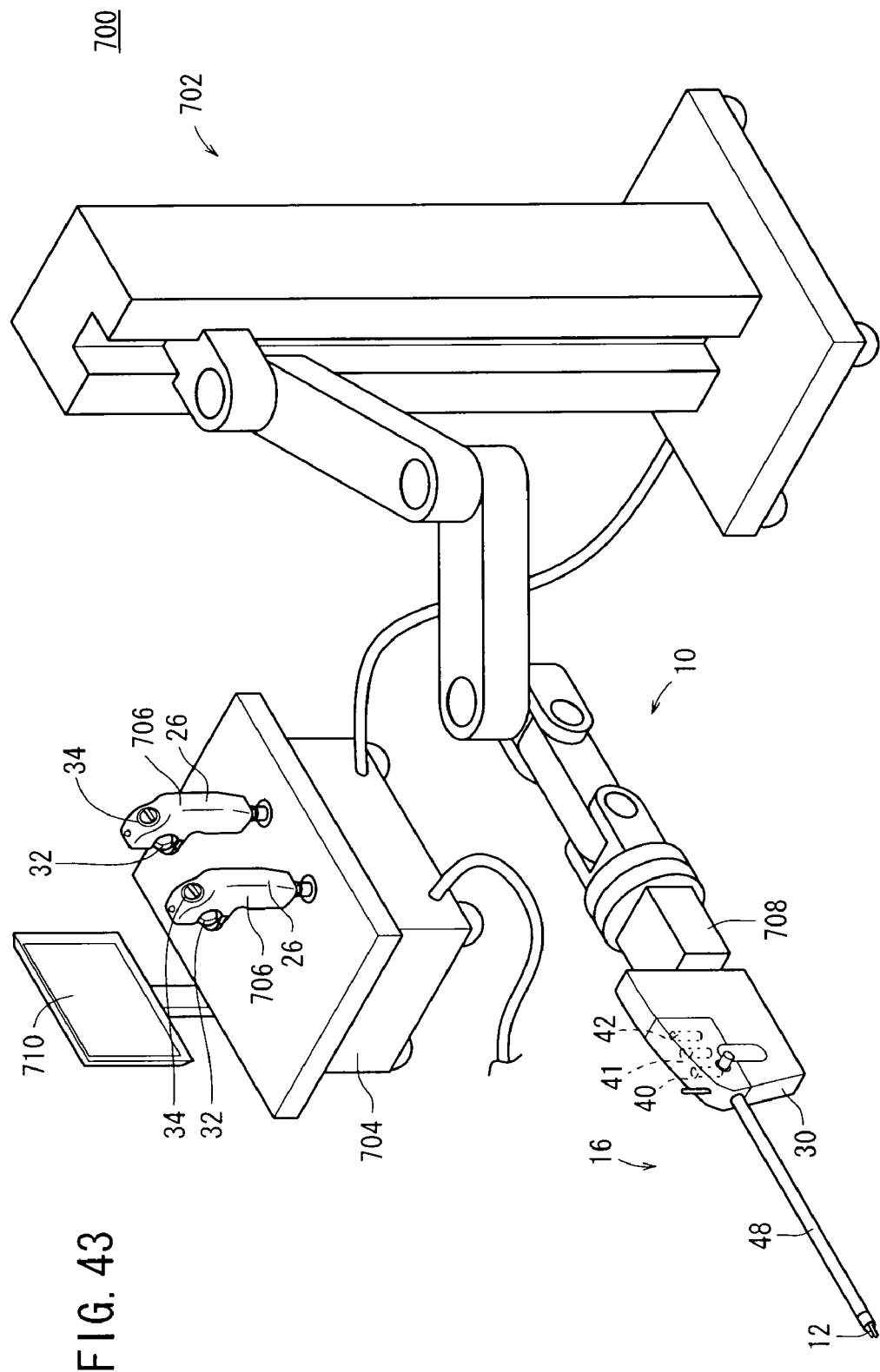
FIG. 43 is a schematic perspective view of a surgical robot system with a working unit connected to the distal end of a robot arm.

The above embodiment may be applied to the surgical robot system 700 shown in FIG. 43, for example.

The surgical robot system 700 includes an articulated robot arm 702, and a console 704 with the working unit 16 connected to the distal end of the robot arm 702. The distal end of the robot arm 702 incorporates therein a mechanism, which operates the same as the manipulator 10. The robot arm 702 may be any means for moving the working unit 16, and is not limited to an installed type, but may also be of an autonomous movable type. The console 704 may be of a table type, a control panel type, or the like.

The robot arm 702 preferably has six or more independent joints (rotary shafts, slide shafts, etc.) for setting the position and orientation of the working unit 16 as desired. The manipulator 10 is integrally combined with a distal end 708 of the robot arm 702. The manipulator 10 includes a motor 42 (an actuator ganged with the manually operable input unit) instead of the trigger lever 32 (see FIG. 8). The motor 42 actuates the wire 56 (see FIG. 8) or the drive coupling pulley 324 (see FIG. 22).

The robot arm 702 operates under control of the console 704, and may be automatically actuatable according to a program, or actuated by joysticks 706 mounted on the console 704, or by a combination of the program and the joysticks 706. The console 704 includes functions of the controller 45. The working unit 16 includes the distal end working unit 12 (12a through 12f).

The console 704 includes the two joysticks 706 serving as an operation commander, and a monitor 710. Although not shown, the two joysticks 706 are capable of individually operating two robot arms 702. The two joysticks 706 are disposed in respective positions where they can easily be operated by both hands of the operator. The monitor 710 displays information such as an image produced by a soft mirror.

The joysticks 706 can be moved vertically and horizontally, twisted, and tilted. The robot arm 702 can be moved depending on movements of the joysticks 706. The joysticks 706 may be master arms. A communication means between the robot arm 702 and the console includes a wired system, a wireless system, a network system, and a combination thereof.

The joysticks 706 have respective trigger levers 32, which can be operated to energize the motor 42.

The manipulator 10 and the distal end working units 12, 12a to 12f have been illustrated as being used in the medical application. However, they can also be used in industrial applications other than the medical application. For example, the manipulator according to the present invention is applicable to robots, manipulators, and distal end working units for performing repairing and maintenance operations in need of grip feelings and strong gripping forces in narrow regions within energy-related devices, energy-related facilities and regions that cannot directly be accessed by human operators.

The manipulator according to the present invention is not limited to the above-described embodiments, but may include any of various additional and/or modified structures without departing from the gist of the present invention.

What is claimed is:

1. A manipulator having a distal end side and a proximal end side thereof comprising:
    a drive member disposed on the proximal end side and being movable back and forth;
    a ring-like flexible member, part of which is connected to the drive member;
    an idle cylindrical member disposed closer to the distal end side than the drive member;
    a driven cylindrical member disposed closer to the distal end side than the idle cylindrical member, and being movable back and forth;
    a guide cylindrical member disposed between the idle cylindrical member and the driven cylindrical member; and
    an end effector being coupled to the driven cylindrical member, wherein the flexible member passes along both sides of the idle cylindrical member and is wound around the driven cylindrical member, and the flexible member crosses between the idle cylindrical member and the guide cylindrical member; and
    a return cylindrical member disposed closer to the distal end side than the driven cylindrical member,
    wherein the flexible member is wound around the driven cylindrical member and the return cylindrical member.

2. A manipulator having a distal end side and a proximal end side thereof comprising:
    a drive member disposed on the proximal end side and being movable back and forth;
    a ring-like flexible member, part of which is connected to the drive member;
    an idle cylindrical member disposed closer to the distal end side than the drive member;
    a driven cylindrical member disposed closer to the distal end side than the idle cylindrical member, and being movable back and forth;
    a guide cylindrical member disposed between the idle cylindrical member and the driven cylindrical member;
    an end effector being coupled to the driven cylindrical member, wherein the flexible member passes along both sides of the idle cylindrical member and is wound around the driven cylindrical member, and the flexible member crosses between the idle cylindrical member and the guide cylindrical member;
    a drive member advancing and retracting mechanism;
    two mechanisms of a first end effector driving mechanism and a second end effector driving mechanism, wherein each of the first end effector driving mechanism and the second end effector driving mechanism comprises the drive member, the ring-like flexible member, the idle cylindrical member, the driven cylindrical member, and the guide cylindrical member, wherein the drive member advancing and retracting mechanism moves the drive member of the first end effector driving mechanism and the drive member of the second end effector driving mechanism, in opposite directions; and
    a return cylindrical member disposed closer to the distal end side than the driven cylindrical member in one of the first end effector driving mechanism and the second end effector driving mechanism,
    wherein the flexible member is wound around the driven cylindrical member and the return cylindrical member.

3. A manipulator according to claim 2, wherein the driven cylindrical member of the first end effector driving mechanism and the driven cylindrical member of the second end effector driving mechanism are disposed coaxially with each other.

4. A manipulator having a distal end side and a proximal end side thereof comprising:
    a drive member disposed on the proximal end side and being movable back and forth;
    a ring-like flexible member, part of which is connected to the drive member;
    an idle cylindrical member disposed closer to the distal end side than the drive member;
    a driven cylindrical member disposed closer to the distal end side than the idle cylindrical member, and being movable back and forth;
    a guide cylindrical member disposed between the idle cylindrical member and the driven cylindrical member;
    an end effector being coupled to the driven cylindrical member, wherein the flexible member passes along both sides of the idle cylindrical member and is wound around the driven cylindrical member, and the flexible member crosses between the idle cylindrical member and the guide cylindrical member;
    a drive member advancing and retracting mechanism; and
    two mechanisms of a first end effector driving mechanism and a second end effector driving mechanism, wherein each of the first end effector driving mechanism and the second end effector driving mechanism comprises the drive member, the ring-like flexible member, the idle cylindrical member, the driven cylindrical member, and the guide cylindrical member, wherein the drive member advancing and retracting mechanism moves the drive member of the first end effector driving mechanism and the drive member of the second end effector driving mechanism, in opposite directions,
    wherein the guide cylindrical member of the first end effector driving mechanism and the guide cylindrical member of the second end effector driving mechanism are disposed coaxially with each other,
    wherein the two guide cylindrical members comprise respective outer first layer guide cylindrical members which are coaxial with each other, and respective inner second layer guide cylindrical members which also are coaxial with each other, and wherein the inner two second layer guide cylindrical members are formed integrally with each other.

5. A manipulator having a distal end side and a proximal end side thereof comprising:
    a drive member disposed on the proximal end side and being movable back and forth;
    a ring-like flexible member, part of which is connected to the drive member;
    an idle cylindrical member disposed closer to the distal end side than the drive member;
    a driven cylindrical member disposed closer to the distal end side than the idle cylindrical member, and being movable back and forth;
    a guide cylindrical member disposed between the idle cylindrical member and the driven cylindrical member;
    an end effector being coupled to the driven cylindrical member, wherein the flexible member passes along both sides of the idle cylindrical member and is wound around the driven cylindrical member, and the flexible member crosses between the idle cylindrical member and the guide cylindrical member;
    a drive member advancing and retracting mechanism; and two mechanisms of a first end effector driving mechanism and a second end effector driving mechanism, wherein each of the first end effector driving mechanism and the second end effector driving mechanism comprises the drive member, the ring-like flexible member, the idle cylindrical member, the driven cylindrical member, and the guide cylindrical member, wherein the drive member advancing and retracting mechanism moves the drive member of the first end effector driving mechanism and the drive member of the second end effector driving mechanism, in opposite directions, wherein the drive member advancing and retracting mechanism has a rotary operating member that rotates about a pivot thereof, wherein the drive member of the first end effector driving mechanism is connected to one portion of the rotary operating member with respect to the pivot, the drive member of the second end effector driving mechanism is connected to another portion of the rotary operating member with respect to the pivot, wherein the two drive members are connected by a drive coupling flexible member, and wherein the rotary operating member is in a form of a cylindrical body, around which the drive coupling flexible member is wound.

6. A manipulator according to claim 5, further comprising an idler being held against the drive coupling flexible member, for defining a layout and a path of the drive coupling flexible member.

7. A manipulator having a distal end side and a proximal end side thereof comprising:
   a drive member disposed on the proximal end side and being movable back and forth;
   a ring-like flexible member, part of which is connected to the drive member;
   an idle cylindrical member disposed closer to the distal end side than the drive member;
   a driven cylindrical member disposed closer to the distal end side than the idle cylindrical member, and being movable back and forth;
   a guide cylindrical member disposed between the idle cylindrical member and the driven cylindrical member;
   an end effector being coupled to the driven cylindrical member, wherein the flexible member passes along both sides of the idle cylindrical member and is wound around the driven cylindrical member, and the flexible member crosses between the idle cylindrical member and the guide cylindrical member;
   a drive member advancing and retracting mechanism;
   two mechanisms of a first end effector driving mechanism and a second end effector driving mechanism, wherein each of the first end effector driving mechanism and the second end effector driving mechanism comprises the drive member, the ring-like flexible member, the idle cylindrical member, the driven cylindrical member, and the guide cylindrical member, wherein the drive member advancing and retracting mechanism moves the drive member of the first end effector driving mechanism and the drive member of the second end effector driving mechanism, in opposite directions;
   a driven coupling flexible member having one end connected to the driven cylindrical member of the first end effector driving mechanism and another end connected to the driven cylindrical member of the second end effector driving mechanism; and
   a driven coupling cylindrical member around which the driven coupling flexible member is wound.

* * * * *